United States Patent
Roberts

(12) 
(10) Patent No.: US 6,221,597 B1
(45) Date of Patent: Apr. 24, 2001

(54) ESSENTIAL GENES OF YEAST AS TARGETS FOR ANTIFUNGAL AGENTS, HERBICIDES, INSECTICIDES AND ANTI-PROLIFERATIVE DRUGS

(75) Inventor: Christopher J. Roberts, Seattle, WA (US)

(73) Assignee: Rosetta Inpharmatics, Inc., Kirkland, WA (US)

( * ) Notice: Subject to any disclaimer, the term of this patent is extended or adjusted under 35 U.S.C. 154(b) by 0 days.

(21) Appl. No.: 09/315,793

(22) Filed: May 21, 1999

(51) Int. Cl.$^7$ .............................. C12Q 1/68; C12N 15/00; C12N 1/15; C12N 15/11; C07H 21/04

(52) U.S. Cl. ......................... 435/6; 435/69.1; 435/91.1; 435/254.1; 435/254.11; 435/254.2; 435/254.21; 536/23.1; 536/23.7; 536/23.74; 536/24.3

(58) Field of Search .......................... 435/6, 69.1, 91.1, 435/254.1, 254.11, 254.2, 254.21; 536/23.1, 23.7, 23.74, 24.3

(56) References Cited

U.S. PATENT DOCUMENTS

| | | |
|---|---|---|
| 4,816,567 | 3/1989 | Cabilly et al. . |
| 5,091,513 | 2/1992 | Huston et al. . |
| 5,223,408 | 6/1993 | Goeddel et al. . |
| 5,225,538 | 7/1993 | Capon et al. . |
| 5,359,046 | 10/1994 | Capon et al. . |
| 5,569,588 | 10/1996 | Ashby et al. . |
| 5,587,458 | 12/1996 | King et al. . |
| 5,608,039 | 3/1997 | Pastan et al. . |
| 5,668,255 | 9/1997 | Murphy . |
| 5,777,085 | 7/1998 | Co et al. . |
| 5,777,888 | 7/1998 | Rine et al. . |
| 5,783,398 | 7/1998 | Marcy et al. . |
| 5,789,554 | 8/1998 | Leung et al. . |
| 5,821,047 | 10/1998 | Garrard et al. . |

FOREIGN PATENT DOCUMENTS

| | | |
|---|---|---|
| WO 97/10365 | 3/1997 | (WO) . |
| WO 98/38329 | 9/1998 | (WO) . |

OTHER PUBLICATIONS

Agrawal and Iyer, 1997, "Perspectives in Antisense Therapeutics", Pharmacol. Ther. 76:151–160.
Altschul et al., 1997, "Gapped BLAST and PSI–BLAST: A New Generation of Protein Database Search Programs", Nucl. Acids Res. 25:3389–3402.
Atkins et al., 1994, "Antisense Gene Expression in Yeast", Biol. Chem. Hoppe–Seyler 375:721–729.
Brachmann et al., 1998, "Designer Deletion Strains Derived from Saccharomyces cerevisiae S288C: A Useful Set of Strains and Plasmids for PCR–Mediated Gene Disruption and Other Applications", Yeast 14:115–132.
Burbaum and Sigal, 1997, "New Technologies for High–Throughput Screening", Curr. Opin. Chem. Biol. 1:72–78.
Castanotto et al., 1998, "Structural Similarities Between Hammerhead Ribozymes and the Spliceosomal RNAs Could Be Responsible for Lack of Ribozyme Cleavage in Yeast", Antisense & Nucl. Acid Drug Devel. 8:1–13.
Chien et al., 1991, "The Two–Hybrid System: A Method to Identify and Clone Genes for Proteins that Interact with a Protein of Interest", Proc. Natl. Acad. Sci. USA 88:9578–9582.
Clackson, 1998, "Redesigning Small Molecule–Protein Interfaces", Curr. Opin. Structural Biol. 8:451–458.
Crooke, 1998, "Antisense Therapeutics", Biotechnol. & Genetic Engineering Rev. 15:121–157.
Cunningham and Wells, 1997, "Minimized Proteins", Curr. Opin. Structural Biol. 7:457–462.
Eckstein, 1997, "Exogenous Application of Ribozymes for Inhibiting Gene Expression", in: Oligonucleotides as Therapeutic Agents, Ciba Foundation Symposium 209, John Wiley & Sons, Chichester, England, pp. 207–217.
Garfinkel et al., 1998, "Ty Mutagenesis", Meth. Microbiol. 26:101–117.
Godowski et al., 1988, "Signal Transduction and Transcriptional Regulation by Glucocorticoid Receptor–LexA Fusion Proteins", Science 241:812–816.
Goffeau et al., 1996, "Life with 6000 Genes", Science 274:546–567.
Hubbard, 1997, "Can Drugs be Designed?", Curr. Opin. Biotechnol. 8:696–700.
Huse et al., 1989, "Generation of a Large Combinatorial Library of the Immunoglobulin Repertoire in Phage Lambda", Science 246:1275–1281.
Ito et al., 1983, "Transformation of Intact Yeast Cells Treated with Alkali Cations", J. Bacteriol. 153:163–168.
Johnson et al., 1992, "Ubiquitin as a Degradation Signal", EMBO J. 11:497–505.
Kanehisa, 1984, "Use of Statistical Criteria for Screening Potential Homologies in Nucleic Acid Sequences", Nucl. Acids Res. 12:203–213.
Kleinberg and Wanke, 1995, "New Approaches and Technologies in Drug Design and Discovery", Am. J. Health Syst. Pharm. 52:1323–1336.

(List continued on next page.)

Primary Examiner—Remy Yucel
Assistant Examiner—Mark L. Shibuya
(74) Attorney, Agent, or Firm—Pennie & Edmonds LLP

(57) ABSTRACT

The present invention relates to genes in Saccharomyces cerevisiae which are essential for germination and proliferation of S. cerevisiae and using the identified genes or their encoded proteins as targets for highly specific antifungal agents, insecticides, herbicides and anti-proliferation drugs. The present invention provides antisense molecules and ribozymes comprising sequences complementary to the sequences of mRNAs of essential genes that function to inhibit the essential genes. The present invention also provides neutralizing antibodies to proteins encoded by essential genes that bind to and inactivate the essential gene products. The present invention further provides pharmaceutical compositions for treating fungal and proliferative diseases, as well as methods of treatment of fungal and proliferative diseases.

15 Claims, 39 Drawing Sheets

OTHER PUBLICATIONS

Figure 1:
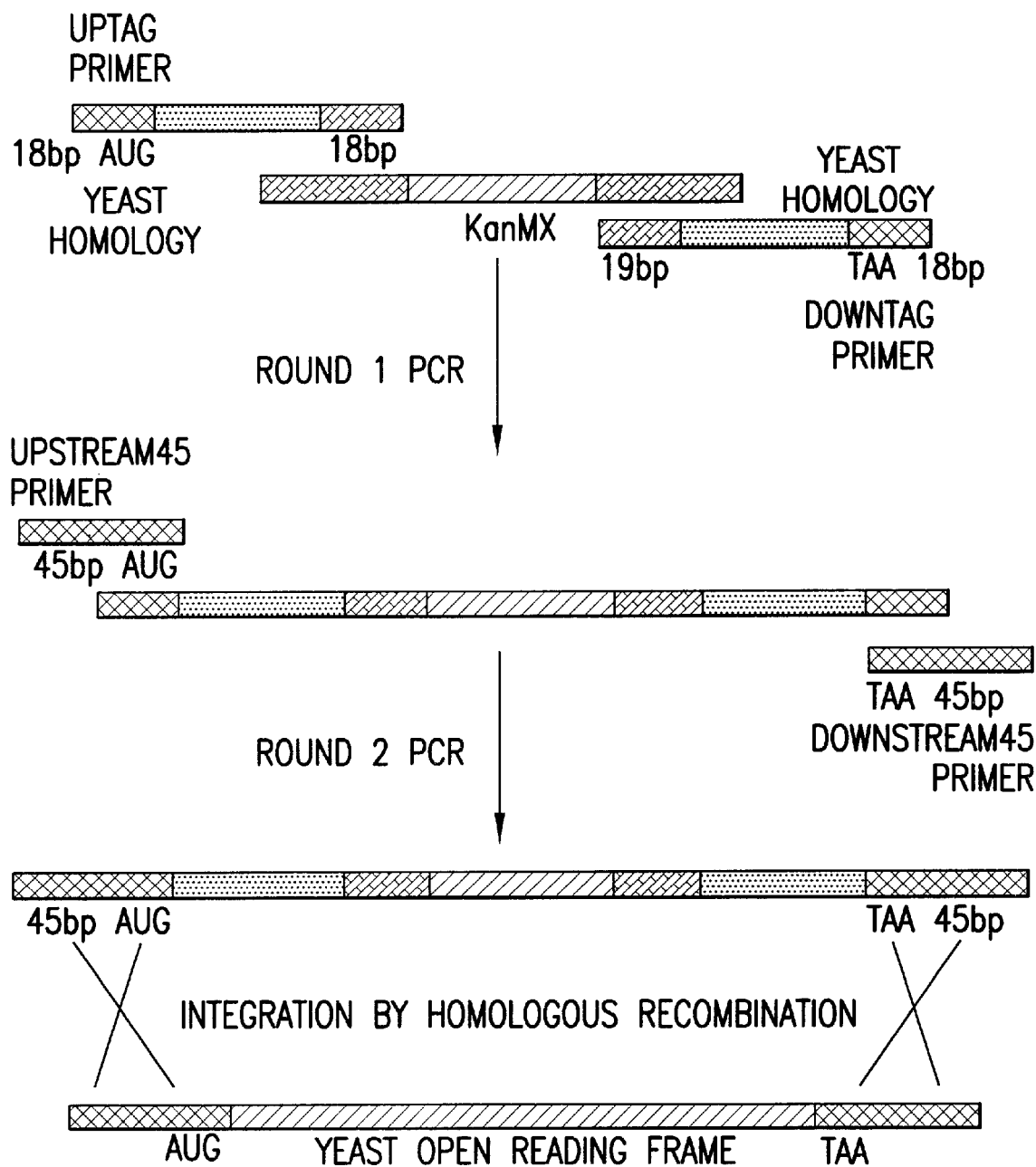

Kubinyi, 1995, "Strategies and Recent Technologies in Drug Discovery", Pharmazie 50:647–662.

Lavrovsky et al., 1997, "Therapeutic Potential and Mechanism of Action of Oligonucleotides and Ribozymes", Biochem. & Mol. Med. 62:11–22.

Mattos and Ringe, 1996, "Locating and Characterizing Binding Sites on Proteins", Nature Biotechnol. 14:595–599.

Merrifield and Stewart, 1965, "Automated Peptide Synthesis", Nature 207:522–523.

Mewes et al., 1997, "Overview of the Yeast Genome", Nature 387(Supp.):7–65.

Nasr et al., 1995, "Artificial Antisense RNA Regulation of YBR1012(YBR136w), an Essential Gene from *Saccharomyces cerevisiae* which Is Important for Progression through G1/S", Mol. Gen. Genet. 249:51–57.

Olsson et al., 1997, "Silencing M1G1 in *Saccharomyces cerevisiae*: Effects of Antisense M1G1 Expression and M1G1 Gene Disruption", Appl. Environ. Microbiol. 63:2366–2371.

Pearson, 1990, "Rapid and Sensitive Sequence Comparison with FASTP and FASTA", Meth. Enzymol. 183:63–98.

Pearson, 1994, "Using the FASTA Program to Search Protein and DNA Sequence Databases", Meth. Mol. Biol. 24:307–331.

Rothstein, 1991, "Targeting, Disruption, Replacement, and Allele Rescue: Integrative DNA Transformation in Yeast", Meth. Enzymol. 194:281–301.

Schiesti and Gietz, 1989, "High Efficiency Transformation and Intact Yeast Cells Using Single Stranded Nucleic Acids as a Carrier", Curr. Genet. 16:339–346.

Schullek et al., 1997, "A High–Density Screening Format for Encoded Combinatorial Libraries: Assay Miniaturization and Its Application to Enzymatic Reactions", Anal. Biochem. 246:20–29.

Sherman, 1991, "Getting Started with Yeast", Meth. Enzymol. 194:3–21.

Sherman and Wakem, 1991, "Mapping Yeast Genes", Meth. Enzymol. 194:38–57.

Stark, 1998, "Studying Essential Genes: Generating and Using Promoter Fusions and Conditional Alleles", Meth. Microbiol. 26:83–99.

Vaughan et al., 1996, "Human Antibodies with Sub–Nanomolar Affinities Isolated from a Large Non–Immunized Phage Display Library", Nature Biotechnol. 14:309–314.

Wach et al., 1994, "New Heterologous Modules for Classical or PCR–Based Gene Disruptions in *Saccharomyces cerevisiae*", Yeast 10:1793–1808.

Ward et al., 1989, "Binding Activities of a Repertoire of Single Immunoglobulin Variable Domains Secreted from *Escherichia coli*", Nature 341:544–546.

Zhao and Lemke, 1998, "Rules for Ribozymes", Mol. Cell. Neurosci. 11:92–97.

Oliver et al., Genbank, Accession No. Z48179 Z71256, Aug. 11, 1997.*

Oliver et al., Genbank, Accession No. Z50111 Z71256, Aug. 11, 1997.*

Habbig et al., Genbank, Accession No. Z74764 Y13140, Aug. 5, 1997.*

Habbig et al., Genbank, Accession No. Z74768 Y13140, Aug. 5, 1997.*

Habbig et al., Genbank, Accession No. Z74776 Y13140, Aug. 11, 1997.*

Alexandraki et al., Genbank, Accession No. Z74819 Y13140, Aug. 5, 1997.*

* cited by examiner

YDR141C / DOP1 on chromosome IV from coordinates 739990 to 734894.

UPTAG primer:
GAGGATCGACAAAAAATGGATGTCCACGAGGTCTCTGATACCCGCACATTTGTTTCCGTACGCTGCAGGTCGAC DOWNTAG primer:
AATTCATAGCTATGCTCACGGTGTCGGTCTCGTAGGATAGGTCCCTCAGACGACTATCGATGAATTCGAGCTCG Upstream45 primer:
AAAAGCCGACAGAGCAGCTTTTTCTGAGAGGATCGACAAAAAATG Downstream45 primer:
ATAACTATATTTCGGTTTATAAAGAAAAATTCATAGCTATGCTCA A primer:    GGAATATTTAGAGTCCGATTACCGT B primer:    AATGTGACCTAACAGACATAGAGGC C primer:    CATATTTGTTGCACTTTTCCTCTTT D primer:    ATGGCGATTACTGATAAACTGCTAC KanB1 primer:    TGTACGGGCGACAGTCACAT KanC3 primer:    CCTCGACATCATCTGCCCAGAT

FIG.3 ydr141c

```
   1 ATGTCCTTAC CACTAAAGCC CCTTACAATT GACTCAAATA ATAAACAACT
  51 AGACTCCAAA CAGAAGAAGT TTCGTGCTAA TGTCGAGCGA GCATTAGAAA
 101 GATTTGACTC TGTAACAGAA TGGGCGGACT ATATTGCTAG TTTGGGAACA
 151 CTATTAAAGG CGTTGCAAAG CTGGTCACCT AAATTTCAGA ATGTAAGGTA
 201 CTATGTTCCT TCTCCATATC AAGTAAGTCG AAGATTGACA TCCTCATTAT
 251 CGCCGGCGTT ACCAGCAGGT GTTCATCAGA AAACTTTAGA AGTATATACG
 301 TATATCTTTG AACATATTGG CCTTGAAACT CTGGCTACAG AATGTAACAT
 351 TTGGATCCCG GGAATTTTAC CTTTGATGAC TTATGCCTCT ATGTCTGTTA
 401 GGTCACATTT GATAGAGCTT TACGATAACT ATATCCTTCT GTTGCCTCAA
 451 ACAACGTTAA GACTGCTCAT CAGACCTTTG ATTTCTAGTT TATTGCCAGG
 501 AATTGATGAT GAAAGCAACG ATTTTTTACC TTTAACTTTA AAACTCATTG
 551 AGACTCTGCA GGAGAACTTG GATGATGATT CCTTATTTTG GCAAACGTTG
 601 TTTCTAGTCA TGACTGCAAA TAAAGGCAGA AGACTGGGCG GACTCACGTG
 651 GTTGACTAGA AAGTTTCCGT CGTTAATGC TGTACCTCAT CTAGTAAATA
 701 AAATAAAAAT GGAAGCGGAA GAGAACCCAA GTGAAACTGA AACCAACGAT
 751 TCTCATCTAG ACAGGAAAAA AAGAAAAGAA GAAGCTTTCA AGGTCTTATT
 801 GCCTGCTGCC AAAGATTTAG TAACCCCTGA ACCAGGTCTA CTTATCCGAT
 851 GCCTTGTCGG TTGTTTAGAA GATGAAAATG ATATTCTTAT TAAAAGGAGC
 901 GTTTTGGACC TTTTATTACA GAGGTTGAGG CTAGACTCTC CCGTTTTGAA
 951 TGTTCTTATT ACTTCTGAGG ATAAAAAGTT ATTGATAATG AGTTGTTGTA
1001 GAACTACTTT GAGCAAGGAT ATGTCTTTGA ACAGAAGAAT ATGGAACTGG
1051 CTTCTCGGTC CTACTGCTGG GGGCATGCTA ACAATAACG GCGGGAACTC
1101 CATGGAATAT ACTACCTCGG TTAAGTCAGC AAACGAGGAA AGTAATGTAT
1151 ATTTTACAAA ATATGGATTA AGCGCCCTTT TAGAAGGTTT AAGCGACCTT
1201 CTTTCAGAAG AAGAATCCGT GTTAACTGCA TTCAGGATAA GTATGGCAGT
1251 AATGGATAGA TGGGAAATTG GCTCACTTGT AATTCCTGAA TTGTTCATCC
1301 CACTTCTCTA TTCCTCGGAA AAATTTAAAC AAAACGAACA AATAATGAAA
1351 ACGGCACGTA CTTTCTTTGA CAATACTGAA ACAAATATTA TATGGGGAAA
1401 GCTATTTCAA GAACTTGAAG ACATCAAAAA CCTAAAAATT TTGGATTTCG
1451 TATTAACAAA TTTTAATATT GGAAACGACG AAGAGATTAT CGTACGCCAC
1501 CTTCCTTTGA TATTATTAAC TTTACTGGCC CTTCCATCTA ATGATAAAGA
1551 TTTCGACAAT ATTTATAAGC TCCAAAAATT TTCTTTGTAC AACAAATTGT
1601 TAAACTATAT CCCCGAGAGA GCCCTTCTCC CTCTCAGTCA CTCAAAACTA
1651 AAGCACGATG ATGAAGTAAG CTGCGAAGAA CTTTTGGCCA AATACGTGG
1701 GTTTTATACC AATGTTTCTA ATCCATCTAG CATTTTAGAG AAAGAAAATA
1751 TAGCTGAGCG TTTGCCACCC TTTACAACAG AAGATCTAAC TTTTTTAATA
1801 GCAGACCTGA TTCAGAAGAA GCTTCTTTCA AGTTTATGGG ACTTGGAAAA
1851 TATCAATGAA AGCTCCAAAT TATTTATAGC TATTTTCGAA AAGATACCTG
1901 AGTCTGAAGA ACTTAAGGA CGATCTCACA TAAGCTGGTC GGATAAAAAA
1951 ATAACTCAGA GCATATTTGA GGCTATTCCC AGGCTTTGTG AATCTAATAA
2001 TGATGCAAAA TCAGAAGAAA TCGTTGGAAT TGTGGAAATT TTTGGTAACT
2051 ACTTATATTC ACGCATGGAA TTCATTGAAT CGATGAAATT ATTGAAAGTA
2101 GTCATGATGG CCGTATGGAA ATCTTTAAAA GATCCACGCC ATCAAATACT
2151 AGGTGTCAAG AACTTAAAGA CTTTAAACAG ATTTATTCCA TCCAAATTTA
```

FIG.4A

```
2201 TTGAAAGTGC GTTAGTGTAT ACTTTTGTGG AAGAGGAAGA TATATCCGAG
2251 AGATTAAGCG TGTTAGATCT GTTATGGACA CAATTAGACT CAGATTCAAA
2301 CTTGATTAGG CGCCCTCTTG AATTAATTTT GGGCGAACTT TTTGATGACC
2351 AGAATCCTTT TTATTTAACC GTTTCAAAGT GGATTTTATC GATATTAAAC
2401 TCGGGATCTG CTTCAAGATT ATTTTACATT TTGACTGATA ATATTTTAAA
2451 GGTTAATCGT CTCGAAAAAG AAAGATTAGA CGAAAGGGAT GATCTTGATA
2501 TGCTCACATA TGAGTTCCAA ATGCTTGCTT ATGTTTTGAA AACAAACAAT
2551 GGACGCACTA GGAAAGTTTT TTCCACTGAG CTTACCTCAA TAAAATCTTC
2601 GACCATATGG AAGAATGAAG ACGTTTCCAC ATATAAAAGT TTGCTGTTGG
2651 TTACATTGAT GAGATTTCTA AATATAAAGA GCAATACACA TGCGAAAAGT
2701 ATCAGGAGTG CTCTGATTCT TTTGGATATC TTACTCGATG GAACTGAGCA
2751 AAATTTCAAG GACATTGTCA TATTTTTGCT GCAAATGTCG TCTAAATATA
2801 TTGCAGAAGA AGGAATTGAG CCCGAGTTAA TAGCAGTTTC CTTGTTAGAT
2851 ATTGTATCGA AGGTTCTCAG ACTATCACAC GATAATGGTA TTAAACTAGA
2901 CATTTTTGAT GACAATGCTG CCCATTTAAA ATATATCGAT TTCCTTGTTA
2951 CCAGCGTTTC AAATATGAAA AGCCCTCTTA TTGTAACGGC CTATGTGAAG
3001 CTTCTTTCCG AAAGCATTGT TTATTTTGAG AATTCTATAT TTCGAATGAT
3051 TTTACCATTG TCTGCATCTC TTGTACAGTG TGTTCAGAGA TTGTTTTTGC
3101 TAGAAAAGAG AGAAGGTGGT TATTACCAAC CAATAGCTTT GCTTCTGGGT
3151 GGTCTGGAAG AGCTATTAGA GATTTCACAT GGTTACCTTG TCACCGAGGA
3201 AAGGGAAGGA TACTTTTCTG GGTCTAATCT AAAGGGTGAT TTTATTCAAT
3251 CCGTTGTTTC AAACGTTTTT TCGTCAGATT CTTCCAATGA AGAAAGTAAG
3301 ATTCAGGGGG AAAGAGACGT AATACTACAA TCTTTCAGAC AGGTGATTTC
3351 ATGCTGTTTA GATATCTGGT ATTGGGCCCA TAACATTTCG TGTAAATCTA
3401 ACGATGATTC TAGCCTGGAC GCCACTAATC ATAACTCATA CAAGTTCAAA
3451 TTTAGGTCGA AGAAACTGTT GGAAACCTTA TTTCTACTAG AACCTTTGGA
3501 ACTTCTGGAA AATTTGATCA GCATTAGATC AGACAATACT ACAGTCACAC
3551 TAGTACATGT GCTCGACGGC AATAAACCCG CCATTACAAT ACCACATTTA
3601 TTGTATGGTG TAATTATCAG ATACAACAGA ACGGCATCTG TCAAGTTTTC
3651 TAATCGTGAC GGAAGTAGGT CAAGCACAAC TAAATTAACT AAAGGGGAGC
3701 CTTCCATGTT AAAAAGATTA AGCGGGGAAT CGATTATTGC ATTTTTGTTT
3751 AACTACGTGG ATTCTGTAGA AAACTCTGCA ATGGAGGAGT TTTATGGGGA
3801 TTTCCTGCTA TTTTTCAGAG AAGTAGCAAC CAATTATAAC CTTTATTCTG
3851 ATGTTTCGTT GTCTATATTA AAACTTGTTG CCCTTATTTC TGGAAAAGTA
3901 AGTAAAACGC AGTTTGGAGA ACAAAAACGA GTTAGGAGGG AGATATCTGA
3951 TGTGTTTTTC AAATACCTAC CTAATGCATT TATAAACTTT ACGAACTTAT
4001 ATCGTGGCCA CCCTGATTCA TTTAAAGATT TAGAATTTGT AGTATGGCGT
4051 GTTCAATATA TCGTCAACGA TCAAATTGGA GGAGACAAGT TTAATACAAC
4101 GTTAGCGACA ATTGTAAATC AATGCCTAAC CCCTTATATC AAACCCAAAA
4151 GTGAAAAAAC TATTCCAGGT TATGTCTTAG AATTGGCCGC GGTCGTATCC
4201 CATTTAGGTT CAAAAGTTAA AAGTTGGAGG CTTTTAATTG CGGAATTGTT
4251 CCAAAATGAC AAAAAACTTT CGGTAATTGG CAGCGATCAA ACTTGGGAAA
4301 AGATTATTTA CGAATGGTCC ATTTATCCAG AAAATAAGTC AAAAATCTTG
4351 AACGATTTAC TATTAGAAAT TGGCTCCAAG CGTTCAAGTG TGACTCCGAC
4401 TTTAATCACG TTTAACTTAG GAAGCGATTC TGAAGTCGAG TACAAGTGCC
4451 AAAACCTTTT GAAAATATCG TACTTGTTGA TGGTATCGCC AAATGACGCA
4501 TATTTGTTGC ACTTTCCTC TTTAATAAGT TGCATTTTCC ACTATTTGGT
```

FIG.4B

```
4551 GTCCAAAGAT ATCAAGCTCA AGGGAAGCTG CTGGATCTTA CTAAGGGTTT
4601 TACTTTTAAG ATTTTCAGAG TCCCATTTCA ATGACTATTG GTCTATGATC
4651 AGTTACTGTT TACAAACTAA TTTGCAAGAA TTTTATGAAT CACTTCAAAT
4701 ACAGTCAGAA GTCGATCCAC AAACAATATT GCAAGTATGT AAAACTTTGG
4751 ATTTGCTACT CTTACTCAAC ATGGAAGGCT TCACCTCTAC GAATGAGTGG
4801 ATCTTTGTTA TTGATACAAT AAATTGCGTA TATAAAACGA ACTCATTCGT
4851 CGCGCTGGTA GATGAAATCG CAGAATTCAA AGATTACGAA ATAACCAAAA
4901 CTGATGATCT TGAATTACCG ACAACTTTAA AAGATGGTCT CCCATTATTA
4951 CGAGGCATTC ACAAAATCGA GAGACACACG CAACTAAGAA GCTTCTTCCA
5001 GAATTTGAGT TATCTACATT ATGAGAAAGT TTACGGACTA GGGTCAGTTG
5051 ATTTATATGG TTGTGGTGAA GATCTCAAAA AAGATATTCT GTCATGA
```

FIG.4C ydr141cp

```
   1 MSLPLKPLTI DSNNKQLDSK QKKFRANVER ALERFDSVTE WADYIASLGT
  51 LLKALQSWSP KFQNVRYYVP SPYQVSRRLT SSLSPALPAG VHQKTLEVYT
 101 YIFEHIGLET LATECNIWIP GILPLMTYAS MSVRSHLIEL YDNYILLLPQ
 151 TTLRLLIRPL ISSLLPGIDD ESNDFLPLTL KLIETLQENL DDDSLFWQTL
 201 FLVMTANKGR RLGGLTWLTR KFPSLNAVPH LVNKIKMEAE ENPSETETND
 251 SHLDRKKRKE EAFKVLLPAA KDLVTPEPGL LIRCLVGCLE DENDILIKRS
 301 VLDLLLQRLR LDSPVLNVLI TSEDKKLLIM SCCRTTLSKD MSLNRRIWNW
 351 LLGPTAGGML NNNGGNSMEY TTSVKSANEE SNVYFTKYGL SALLEGLSDL
 401 LSEEESVLTA FRISMAVMDR WEIGSLVIPE LFIPLLYSSE KFKQNEQIMK
 451 TARTFFDNTE TNIIWGKLFQ ELEDIKNLKI LDFVLTNFNI GNDEEIIVRH
 501 LPLILLTLLA LPSNDKDFDN IYKLQKFSLY NKLLNYIPER ALLPLSHSKL
 551 KHDDEVSCEE LLAKIRGFYT NVSNPSSILE KENIAERLPP FTTEDLTFLI
 601 ADLIQKKLLS SLWDLENINE SSKLFIAIFE KIPESEELKG RSHISWSDKK
 651 ITQSIFEAIP RLCESNNDAK SEEIVGIVEI FGNYLYSRME FIESMKLLKV
 701 VMMAVWKSLK DPRHQILGVK NLKTLNRFIP SKFIESALVY TFVEEEDISE
 751 RLSVLDLLWT QLDSDSNLIR RPLELILGEL FDDQNPFYLT VSKWILSILN
 801 SGSASRLFYI LTDNILKVNR LEKERLDERD DLDMLTYEFQ MLAYVLKTNN
 851 GRTRKVFSTE LTSIKSSTIW KNEDVSTYKS LLLVTLMRFL NIKSNTHAKS
 901 IRSALILLDI LLDGTEQNFK DIVIFLLQMS SKYIAEEGIE PELIAVSLLD
 951 IVSKVLRLSH DNGIKLDIFD DNAAHLKYID FLVTSVSNMK SPLIVTAYVK
1001 LLSESIVYFE NSIFRMILPL SASLVQCVQR LFLLEKREGG YYQPIALLLG
1051 GLEELLEISH GYLVTEEREG YFSGSNLKGD FIQSVVSNVF SSDSSNEESK
1101 IQGERDVILQ SFRQVISCCL DIWYWAHNIS CKSNDDSSLD ATNHNSYKFK
1151 FRSKKLLETL FLLEPLELLE NLISIRSDNT TVTLVHVLDG NKPAITIPHL
1201 LYGVIIRYNR TASVKFSNRD GSRSSTTKLT KGEPSMLKRL SGESIIAFLF
1251 NYVDSVENSA MEEFYGDFLL FFREVATNYN LYSDVSLSIL KLVALISGKV
1301 SKTQFGEQKR VRREISDVFF KYLPNAFINF TNLYRGHPDS FKDLEFVVWR
1351 VQYIVNDQIG GDKFNTTLAT IVNQCLTPYI KPKSEKTIPG YVLELAAVVS
1401 HLGSKVKSWR LLIAELFQND KKLSVIGSDQ TWEKIIYEWS IYPENKSKIL
1451 NDLLLEIGSK RSSVTPTLIT FNLGSDSEVE YKCQNLLKIS YLLMVSPNDA
1501 YLLHFSSLIS CIFHYLVSKD IKLKGSCWIL LRVLLLRFSE SHFNDYWSMI
1551 SYCLQTNLQE FYESLQIQSE VDPQTILQVC KTLDLLLLLN MEGFTSTNEW
1601 IFVIDTINCV YKTNSFVALV DEIAEFKDYE ITKTDDLELP TTLKDGLPLL
1651 RGIHKIERHT QLRSFFQNLS YLHYEKVYGL GSVDLYGCGE DLKKDILS
```

FIG.5 ydr141cp
blastp nr
Sequences producing significant alignments:

```
                                                                    Score    E
                                                                   (bits)  Value pir||S51869  probable membrane protein YDR141c - yeast (Saccharo...  3077   0.0
emb|CAA22324| (AL034393) cDNA EST yk422d8.5 comes from this gen...    101   3e-20
emb|CAB39005.1| (AL034558) predicted using hexExon; MAL3P2.18 (...     59   2e-07
dbj|BAA76777.1| (AB023150) KIAA0933 protein [Homo sapiens]             45   0.006
```

FIG.6

Sequences producing significant alignments:

```
                                                                    Score    E
                                                                   (bits)  Value sp|P10614|CP51_YEAST   CYTOCHROME P450 LI (14DM) (LANOSTEROL 14-A...  1095   0.0
sp|P50859|CP51_CANGA   CYTOCHROME P450 LI (14DM) (LANOSTEROL 14-A...   929   0.0
sp|P14263|CP51_CANTR   CYTOCHROME P450 LI (P450-L1A1) (LANOSTEROL...   707   0.0
sp|P10613|CP51_CANAL   CYTOCHROME P450 LI (P450-L1A1) (LANOSTEROL...   707   0.0
sp|Q02315|CP51_ISSOR   CYTOCHROME P450 LI (P450-L1A1) (LANOSTEROL...   553   e-157
sp|Q09736|CP51_SCHPO   PUTATIVE CYTOCHROME P450 LI (LANOSTEROL 14     491   e-138
sp|P49602|CP51_USTMA   CYTOCHROME P450 LI (14DM) (LANOSTEROL 14-A...   469   e-132
sp|Q12664|CP51_PENIT   CYTOCHROME P450 LI (P450-L1A1) (EBURICOL 1...   464   e-130
sp|Q16850|CP51_HUMAN   CYTOCHROME P450 LI (LANOSTEROL 14-ALPHA DE...   318   2e-86
sp|Q64654|CP51_RAT     CYTOCHROME P450 LI (LANOSTEROL 14-ALPHA DEME...  315   1e-85
sp|P22680|CP70_HUMAN   CYTOCHROME P450 VII (CHOLESTEROL 7-ALPHA-M...    98   4e-20
sp|P29980|CPXN_ANASP   PROBABLE CYTOCHROME P450 (ORF3)                  95   3e-19
```

FIG.7 ydr141c/DOP1

Oligonucleotides for disruption of YDR091C on chromosome IV from coordinates 628527 to 626701.

UPTAG primer:
ACACGACAGACCATAATGGATGTCCACGAGGTCTCTGAGATTTACTAACCCTCTGCCGTA
CGCTGCAGGTCGAC DOWNTAG primer:
CGAATCCCAAGATGCTTACGGTGTCGGTCTCGTAGGAGGGTTCTCCACTTCACTGATCGA
TGAATTCGAGCTCG Upstream45 primer:
TAGCCTTCTGCAAAAGTTCTTAAGAAAACACGACAGACCATAATG Downstream45 primer:
AATAAAACAATCGTCCTCTTGGTTCTCCGAATCCCAAGATGCTTA A primer:     TCAGTCACCTGTTCATAAGCAAATA B primer:     TATAGCCTTGATATCATCTTCCAGC C primer:     GTTTCAGACTGATGTCGTTAAACCT D primer:     ATGAAATAAACTGGAGTACGGATCA KanB1 primer:    TGTACGGGCGACAGTCACAT KanC3 primer:    CCTCGACATCATCTGCCCAGAT

FIG.9

YDR091C DNA Sequence

```
   1 ATGAGTGATA AAAACAGTCG TATCGCTATC GTTAGCGCTG ATAAATGTAA
  51 ACCAAAAAAG TGTCGTCAAG AGTGTAAACG TTCGTGTCCC GTTGTGAAAA
 101 CTGGTAAATT ATGTATTGAA GTCACTCCAA CTTCAAAAAT CGCATTCATT
 151 TCCGAAATCT TGTGTATTGG TTGTGGTATT TGCGTTAAGA AATGTCCATT
 201 TGATGCTATT CAAATTATCA ATTTGCCAAC TAATTTAGAA GCCCATGTAA
 251 CTCACCGTTA CTCTGCCAAT AGTTTCAAAC TGCACAGATT GCCAACACCA
 301 AGACCGGGTC AAGTCCTTGG TTTAGTCGGT ACCAACGGTA TTGGTAAGTC
 351 TACCGCCTTG AAAATCTTAG CCGGTAAACA AAAACCTAAT TTAGGTCGTT
 401 TTGATGATCC TCCTGAATGG CAGGAAATTA TTAAATATTT CCGTGGTTCT
 451 GAATTACAAA ATTACTTCAC CAAGATGCTG GAAGATGATA TCAAGGCTAT
 501 AATCAAACCT CAATATGTTG ATAACATTCC TCGTGCTATT AAAGGTCCGG
 551 TTCAAAAAGT TGGCGAACTT TTGAAATTGA GAATGGAAAA AAGTCCTGAA
 601 GATGTGAAAC GCTACATCAA AATTTTACAG TTGGAAAACG TTTTGAAAAG
 651 AGATATTGAA AAGTTATCTG GTGGTGAACT GCAAAGATTT GCCATTGGTA
 701 TGTCATGTGT TCAAGAGGCT GATGTTTATA TGTTCGATGA ACCTTCATCT
 751 TATTTGGATG TTAAGCAACG TTTGAATGCC GCTCAAATTA TTAGATCTTT
 801 ACTAGCTCCA ACTAAATACG TTATTTGTGT TGAGCACGAT TTGTCAGTTT
 851 TGGATTATCT TTCCGATTTC GTTTGTATCA TATATGGTGT TCCATCTGTT
 901 TACGGTGTTG TTACATTACC AGCCTCTGTC AGAGAAGGTA TCAACATATT
 951 CTTGGACGGT CATATTCCTG CTGAAAACCT GAGATTCAGA ACTGAAGCTT
1001 TACAATTTAG AATAGCTGAT GCTACCGAAG ACTTGCAGAA TGACTCTGCT
1051 AGTCGCGCCT TCTCTTACCC AAGTTTGAAG AAAACTCAAG GTGATTTTGT
1101 TTTGAATGTT GAAGAAGGTG AATTCTCCGA TTCCGAAATC CTTGTTATGA
1151 TGGGTGAAAA CGGTACCGGT AAGACCACTT TGATCAAATT ACTAGCTGGT
1201 GCTTTGAAGC CAGATGAAGG ACAAGATATT CCAAAATTGA ATGTTTCTAT
1251 GAAACCACAA AAAATTGCAC CAAAGTTCCC AGGTACTGTC AGACAATTGT
1301 TTTTCAAGAA AATTAGAGGA CAATTCCTAA ATCCACAGTT TCAGACTGAT
1351 GTCGTTAAAC CTTTAAGGAT TGACGATATT ATTGATCAAG AAGTCCAACA
1401 TTTGTCTGGT GGTGAATTAC AAAGAGTCGC CATCGTCTTG GCATTGGGTA
1451 TCCCAGCAGA CATATACTTG ATTGATGAGC CATCTGCCTA CTTAGATTCC
1501 GAACAACGTA TTATCTGTTC TAAAGTTATC AGAAGATTCA TCTTACATAA
1551 TAAGAAAACT GCGTTTATTG TCGAGCACGA TTTCATCATG GCTACTTATC
1601 TTGCTGATAA GGTCATTGTT TTTGAAGGTA TTCCTTCCAA GAATGCTCAC
1651 GCAAGAGCCC CTGAATCTTT GTTGACTGGT TGTAACAGAT TTTTGAAGAA
1701 TTTGAATGTC ACCTTCAGAA GGGATCCAAA CTCCTTCAGA CCAAGAATTA
1751 ATAAGCTAGA TTCCCAAATG GATAAAGAAC AAAAATCATC AGGAAACTAC
1801 TTTTTCTTGG ATAACACCGG TATTTAA
```

FIG.10

YDR091Cp

```
1   MSDKNSRIAI VSADKCKPKK CRQECKRSCP VVKTGKLCIE VTPTSKIAFI
51  SEILCIGCGI CVKKCPFDAI QIINLPTNLE AHVTHRYSAN SFKLHRLPTP
101 RPGQVLGLVG TNGIGKSTAL KILAGKQKPN LGRFDDPPEW QEIIKYFRGS
151 ELQNYFTKML EDDIKAIIKP QYVDNIPRAI KGPVQKVGEL LKLRMEKSPE
201 DVKRYIKILQ LENVLKRDIE KLSGGELQRF AIGMSCVQEA DVYMFDEPSS
251 YLDVKQRLNA AQIIRSLLAP TKYVICVEHD LSVLDYLSDF VCIIYGVPSV
301 YGVVTLPASV REGINIFLDG HIPAENLRFR TEALQFRIAD ATEDLQNDSA
351 SRAFSYPSLK KTQGDFVLNV EEGEFSDSEI LVMMGENGTG KTTLIKLLAG
401 ALKPDEGQDI PKLNVSMKPQ KIAPKFPGTV RQLFFKKIRG QFLNPQFQTD
451 VVKPLRIDDI IDQEVQHLSG GELQRVAIVL ALGIPADIYL IDEPSAYLDS
501 EQRIICSKVI RRFILHNKKT AFIVEHDFIM ATYLADKVIV FEGIPSKNAH
551 ARAPESLLTG CNRFLKNLNV TFRRDPNSFR PRINKLDSQM DKEQKSSGNY
601 FFLDNTGI
```

FIG.11 ydr091c blastp nr

|  | Score (bits) | E Value |
|---|---|---|
| Sequences producing significant alignments: | | |
| pir\|\|S58091 probable membrane protein YDR091c - yeast (Saccharo... | 1224 | 0.0 |
| emb\|CAA19324\| (AL023780) ABC transporter [Schizosaccharomyces p... | 875 | 0.0 |
| pir\|\|S63672 RNase L inhibitor (clone 8) - human >gi\|1587696\|prf... | 863 | 0.0 |
| gi\|3273417 (U90446) RNAse L inhibitor [Mus musculus] | 859 | 0.0 |
| ref\|NP_002931.1\|PRNASELI\| ribonuclease L (2',5'-oligoisoadenyla... | 849 | 0.0 |
| emb\|CAA16710.1\| (AL021687) RNase L inhibitor [Arabidopsis thali... | 842 | 0.0 |
| dbj\|BAA29953\| (AP000003) 590aa long hypothetical transport prot... | 561 | e-159 |
| sp\|Q58129\|Y719_METJA HYPOTHETICAL ABC TRANSPORTER ATP-BINDING P... | 559 | e-158 |
| emb\|CAA52920\| (X74987) 2'-5' oligoadenylate binding protein [Ho... | 545 | e-154 |
| gi\|2622826 (AE000927) RNase L inhibitor [Methanobacterium therm... | 527 | e-149 |
| gi\|2650646 (AE001106) RNase L inhibitor [Archaeoglobus fulgidus] | 504 | e-142 |
| emb\|CAA16709.1\| (AL021687) putative protein [Arabidopsis thaliana] | 110 | 3e-23 |
| dbj\|BAA17810\| (D90909) ABC transporter [Synechocystis sp.] | 93 | 4e-18 |
| emb\|CAA91229\| (Z56283) orf1 [Lactobacillus helveticus] | 89 | 9e-17 |
| gi\|149795 (M96826) iron sulfur protein [Methanothermus fervidus] | 88 | 1e-16 |
| sp\|Q57242\|UUP1_HAEIN ABC TRANSPORTER ATP-BINDING PROTEIN UUP-1 ... | 85 | 2e-15 |
| gb\|AAD07317.1\| (AE000544) oligopeptide ABC transporter, ATP-bin... | 85 | 2e-15 |
| sp\|O05519\|YDIF_BACSU HYPOTHETICAL ABC TRANSPORTER ATP-BINDING P... | 82 | 1e-14 |
| gi\|4154751 (AE001461) ABC transporter, ATP-binding protein [Hel... | 80 | 3e-14 |
| sp\|Q57855\|Y412_METJA HYPOTHETICAL ABC TRANSPORTER ATP-BINDING P... | 80 | 4e-14 |
| gi\|2983231 (AE000698) ABC transporter [Aquifex aeolicus] | 80 | 6e-14 |
| gi\|2621521 (AE000829) methyl coenzyme M reductase system, compo... | 79 | 7e-14 |
| gi\|2649976 (AE001060) nitrate ABC transporter, ATP-binding prot... | 79 | 7e-14 |
| emb\|CAB15245\| (Z99120) similar to multiple sugar ABC transporte... | 79 | 7e-14 |
| dbj\|BAA29226.1\| (AP000001) 345aa long hypothetical transport-AT... | 79 | 7e-14 |
| dbj\|BAA29090.1\| (AP000001) 373aa long hypothetical sugar-bindin... | 79 | 7e-14 |
| sp\|Q01937\|LACK_AGRRD LACTOSE TRANSPORT ATP-BINDING PROTEIN LACK... | 78 | 2e-13 |
| pir\|\|A64455 methyl coenzyme M reductase system, component A2 - ... | 78 | 2e-13 |
| sp\|P10091\|CYSA_MARPO PROBABLE SULFATE TRANSPORT ATP-BINDING PRO... | 78 | 2e-13 |
| dbj\|BAA29847\| (AP000003) 357aa long hypothetical sugar transpor... | 77 | 3e-13 |
| sp\|Q57554\|Y089_METJA HYPOTHETICAL ABC TRANSPORTER ATP-BINDING P... | 77 | 3e-13 |
| gi\|2648707 (AE000976) cobalt transport ATP-binding protein (cbi... | 77 | 4e-13 |
| pir\|\|F64470 sulfate permease (cysA) - Methanococcus jannaschii ... | 77 | 4e-13 |
| dbj\|BAA30335\| (AP000005) 250aa long hypothetical ferrichrome tr... | 76 | 6e-13 |
| emb\|CAB15283\| (Z99120) similar to iron(III) dicitrate transport... | 76 | 6e-13 |
| gi\|2649574 (AE001033) ABC transporter, ATP-binding protein [Arc... | 76 | 8e-13 |
| sp\|P45535\|YHES_ECOLI HYPOTHETICAL ABC TRANSPORTER ATP-BINDING P... | 75 | 1e-12 |
| gi\|2650201 (AE001075) iron (III) ABC transporter, ATP-binding p... | 75 | 1e-12 |
| emb\|CAA15894\| (AL021006) sugC [Mycobacterium tuberculosis] | 74 | 2e-12 |

FIG. 12A

```
pir||C64496    ABC transporter ATP-binding protein - Methanococcus...    74    3e-12
sp|P74548|CYSA_SYNY3  SULFATE TRANSPORT ATP-BINDING PROTEIN CYSA...       74    3e-12
emb|CAA67569|  (X99127) ATP binding protein [Staphylococcus epid...       74    3e-12
sp|P40735|YBXA_BACSU  HYPOTHETICAL ABC TRANSPORTER ATP-BINDING P...        73    4e-12
pir||D64507    methyl coenzyme M reductase system, component A2 ho...     73    4e-12
dbj|BAA22247|  (AB000617) YcdI [Bacillus subtilis] >gi|2632572|e...       73    4e-12
sp|P48334|YCXD_CYAPA  PROBABLE ABC TRANSPORTER ATP-BINDING PROTE...        73    4e-12
gi|2826445    (U67606) methyl coenzyme M reductase system, compone...      73    4e-12
sp|Q57213|YE74_HAEIN  HYPOTHETICAL ABC TRANSPORTER ATP-BINDING P...        73    4e-12
sp|Q47087|CBRD_ERWCH  IRON(III) CHLORIDE/DICITRATE TRANSPORT ATP...        73    4e-12
dbj|BAA29263.1|  (AP000001) 375aa long hypothetical multiple sug...       73    4e-12
sp|P56344|CYSA_CHLVU  PROBABLE SULFATE TRANSPORT ATP-BINDING PRO...        73    6e-12
pir||S25202    srmB protein - Streptomyces ambofaciens >gi|581584|...     73    6e-12
dbj|BAA30456|  (AP000006) 330aa long hypothetical ATP-binding tr...       73    7e-12
dbj|BAA22320|  (D86417) YfmF [Bacillus subtilis] >gi|2633073|emb...       73    7e-12
emb|CAA70125|  (Y08921) msiK [Streptomyces reticuli]                      73    7e-12
```

FIG.12B

```
pir||S63672 RNase L inhibitor (clone 8) - human >gi|1587696|prf||2207222A RNase
         L inhibitor [Homo sapiens]
         Length = 599

Score =  863 bits (2206), Expect = 0.0
 Identities = 414/605 (68%), Positives = 503/605 (82%), Gaps = 6/605 (0%)

Query: 1    MSDKNSRIAIVSADKCKPKKCRQECKRSCPVVKTGKLCIEVTPTSKIAFISEILCIGCGI 60
            M+DK +RIAIV+ DKCKPKKCRQECK+SCPVV+ GKLCIEVTP SKIA+ISE LCIGCGI
Sbjct: 1    MADKLTRIAIVNHDKCKPKKCRQECKKSCPVVRMGKLCIEVTPQSKIAWISETLCIGCGI 60

Query: 61   CVKKCPFDAIQIINLPTNLEAHVTHRYSANSFKLHRLPTPRPGQVLGLVGTNGIGKSTAL 120
            C+KKCPF A+ I+NLP+NLE   THRY AN+FKLHRLP PRPG+VLGLVGTNGIGKSTAL
Sbjct: 61   CIKKCPFGALSIVNLPSNLEKETTHRYCANAFKLHRLPIPRPGEVLGLVGTNGIGKSTAL 120

Query: 121  KILAGKQKPNLGRFDDPPEWQEIIKYFRGSELQNYFTKMLEDDIKAIIKPQYVDNIPRAI 180
            KILAGKQKPNLG++DDPP+WQEI+ YFRGSELQNYFTK+LEDD+KAIIKPQYVD IP+A
Sbjct: 121  KILAGKQKPNLGKYDDPPDWQEILTYFRGSELQNYFTKILEDDLKAIIKPQYVDQIPKAA 180

Query: 181  KGPVQKVGELLKLRMEKSPEDVKRYIKILQLENVLKRDIEKLSGGELQRFAIGMSCVQEA 240
            KG V   G +L + E  + +      + L L ++ +R++E LSGGELQRFA  + C+Q+A
Sbjct: 181  KGTV---GSILDRKDETKTQAI--VCQQLDLTHLKERNVEDLSGGELQRFACAVVCIQKA 235

Query: 241  DVYMFDEPSSYLDVKQRLNAAQIIRSLLAPTKYVICVEHDLSVLDYLSDFVCIIYGVPSV 300
            D++MFDEPSSYLDVKQRL AA   IRSL+ P +Y+I VEHDLSVLDYLSDF+C +YGVPS
Sbjct: 236  DIFMFDEPSSYLDVKQRLKAAITIRSLINPDRYIIVVEHDLSVLDYLSDFICCLYGVPSA 295

Query: 301  YGVVTLPASVREGINIFLDGHIPAENLRFRTEALQFRIADATEDLQNDSASRAFSYPSLK 360
            YGVVT+P SVREGINIFLDG++P ENLRFR +L F++A+   +        + YP +K
Sbjct: 296  YGVVTMPFSVREGINIFLDGYVPTENLRFRDASLVFKVAETANE-EEVKKMCMYKYPGMK 354

Query: 361  KTQGDFVLNVEEGEFSDSEILVMMGENGTGKTTLIKLLAGALKPDEGQDIPKLNVSMKPQ 420
            K  G+F L + GEF+DSEI+VM+GENGTGKTT I+++AG LKPDEG ++P LNVS KPQ
Sbjct: 355  KKMGEFELAIVAGEFTDSEIMVMLGENGTGKTTFIRMLAGRLKPDEGGEVPVLNVSYKPQ 414

Query: 421  KIAPKFPGTVRQLFFKKIRGQFLNPQFQTDVVKPLRIDDIIDQEVQHLSGGELQRVAIVL 480
            KI+PK  G+VRQL  +KIR  + +PQF TDV+KPL+I+++IDQEVQ LSGGELQRVA+ L
Sbjct: 415  KISPKSTGSVRQLLHEKIRDAYTHPQFVTDVMKPLQIENIIDQEVQTLSGGELQRVALAL 474

Query: 481  ALGIPADIYLIDEPSAYLDSEQRIICSKVIRRFILHNKKTAFIVEHDFIMATYLADKVIV 540
             LG PAD+YLIDEPSAYLDSEQR++ ++V++RFILH KKTAF+VEHDFIMATYLAD+VIV
Sbjct: 475  CLGKPADVYLIDEPSAYLDSEQRLMAARVVKRFILHAKKTAFVVEHDFIMATYLADRVIV 534

Query: 541  FEGIPSKNAHARAPESLLTGCNRFLKNLNVTFRRDPNSFRPRINKLDSQMDKEQKSSGNY 600
            F+G+PSKN A +P++LL G N+FL L +TFRRDPN++RPRINKL+S  D EQK SGNY
Sbjct: 535  FDGVPSKNTVANSPQTLLAGMNKFLSQLEITFRRDPNNYRPRINKLNSIKDVEQKKSGNY 594

Query: 601  FFLDN 605
            FFLD+
Sbjct: 595  FFLDD 599
```

FIG.13

```
emb|CAA52920| (X74987) 2'-5' oligoadenylate binding protein [Homo sapiens]
            Length = 402

Score =  545 bits (1388), Expect = e-154
 Identities = 261/397 (65%), Positives = 326/397 (81%), Gaps = 1/397 (0%)

Query: 209 LQLENVLKRDIEKLSGGELQRFAIGMSCVQEADVYMFDEPSSYLDVKQRLNAAQIIRSLL 268
           L L ++ +R++E LSGGELQRFA  + C+Q+AD++MFDEPSSYLDVKQRL AA  IRSL+
Sbjct:   7 LDLTHLKERNVEDLSGGELQRFACAVVCIQKADIFMFDEPSSYLDVKQRLKAAITIRSLI 66

Query: 269 APTKYVICVEHDLSVLDYLSDFVCIIYGVPSVYGVVTLPASVREGINIFLDGHIPAENLR 328
             P +Y+I VEHDLSVLDYLSDF+C  +YGVPS YGVVT+P SVREGINIFLDG++P ENLR
Sbjct:  67 NPDRYIIVVEHDLSVLDYLSDFICCLYGVPSAYGVVTMPFSVREGINIFLDGYVPTENLR 126

Query: 329 FRTEALQFRIADATEDLQNDSASRAFSYPSLKKTQGDFVLNVEEGEFSDSEILVMMGENG 388
           FR +L F++A+    + +        + YP +KK  G+F L +  GEF+DSEI+VM+GENG
Sbjct: 127 FRDASLVFKVAETANE-EEVKKMCMYKYPGMKKKMGEFELAIVAGEFTDSEIMVMLGENG 185

Query: 389 TGKTTLIKLLAGALKPDEGQDIPKLNVSMKPQKIAPKFPGTVRQLFFKKIRGQFLNPQFQ 448
           TGKTT I++LAG LKPDEG ++P LNVS KPQKI+PK   G+VRQL  +KIR + +PQF
Sbjct: 186 TGKTTFIRMLAGRLKPDEGGEVPVLNVSYKPQKISPKSTGSVRQLLHEKIRDAYTHPQFV 245

Query: 449 TDVVKPLRIDDIIDQEVQHLSGGELQRVAIVLALGIPADIYLIDEPSAYLDSEQRIICSK 508
           TDV+KPL+I++IIDQEVQ LSGGELQRV + L LG PAD+YLIDEPSAYLDSEQR++ ++
Sbjct: 246 TDVMKPLQIENIIDQEVQTLSGGELQRVRLRLCLGKPADVYLIDEPSAYLDSEQRLMAAR 305

Query: 509 VIRRFILHNKKTAFIVEHDFIMATYLADKVIVFEGIPSKNAHARAPESLLTGCNRFLKNL 568
           V++RFILH KKTAF+VEHDFIMATYLAD+VIVF+G+PSKN  A +P++LL G N+FL  L
Sbjct: 306 VVVKRFILHAKKTAFVVEHDFIMATYLADRVIVFDGVPSKNTVANSPQTLLAGMNKFLSQL 365

Query: 569 NVTFRRDPNSFRPRINKLDSQMDKEQKSSGNYFFLDN 605
            +TFRRDPN++RPRINKL+S  D EQK SGNYFFLD+
Sbjct: 366 EITFRRDPNNYRPRINKLNSIKDVEQKKSGNYFFLDD 402
```

FIG.14

YOL022C on chromosome XV from coordinates 281498 to 280272.

UPTAG primer:
ATTATCCACTATCTCATGGATGTCCACGAGGTCTCTGGAGACTCTTGCACATTATGCGTA
CGCTGCAGGTCGAC DOWNTAG primer:
CAAATTACCCACTATTCACGGTGTCGGTCTCGTAGCAGGACGCTGCATGTTTATGATCGA
TGAATTCGAGCTCG Upstream45 primer:
AAGAGGAAAAGTAGAAGCCAAGAGTCAATTATCCACTATCTCATG Downstream45 primer:
ATTTAATTATCAAAAATTCATGAAAGACAAATTACCCACTATTCA A primer:    ATTTCACCTGCAAGTTCATAAAAAG B primer:    CATATAATACTCTGTCATCCTGGGG C primer:    TCGGTTATGTAGAAGAATGTGTCAA D primer:    AATTCATTGGTGCAGGTAGTTAGAG KanB1 primer:    TGTACGGGCGACAGTCACAT KanC3 primer:    CCTCGACATCATCTGCCCAGAT

FIG.16 yol022c

```
   1  ATGTCCAAAA TAGAAGAGCT ACCACCATCA GATACTGATG ACCATTCGTA
  51  TTCTAGTAAA CCGGGAGATG TATTTTTAGC ATTTGTGGAC GCACCTGTTA
 101  AAGAGACTGA TGACATATTA GTTGAAGATA GCTTTATTGG CGGTGAACCT
 151  AAGTGGCTAC ATCCGGATTC CGAACCACCT GCTGAACTAT TGAAATGTGG
 201  TGCTTGTAAA TCAGCGGATA ATATGAAGCT GTTACTACAA GCTTTTTCGC
 251  CCTTAGATGA TGAGCAGATG AGTGCCATAC AACAACGTCT TGGTATCAAT
 301  AATATGAGCT ATATTAATCC CCAGGATGAC AGAGTATTAT ATGTCTTCCT
 351  GTGTACCGAA TGTCAAAGGA AGGGCAATTC TGTTCGCTGT ATCAGAGGAG
 401  TAAAGAAGAA TAAAAACGTT GATAGCCTTT CCGAAAAAAT GGCTTCAACT
 451  TCATTGGAAA AAGACTTCCA AATCAATCCC TTTGACTTGT CGAATAATTC
 501  AGATTCTAAA TGTAATGCTT TTTCAAGCAA CCCATTTGGC GGTGCAAATG
 551  CTAACCCTTT TGGAGCTGAT AGCATTAATT CCAATATATC ACAAAGCAAG
 601  GACGAAGGCA AAAAGAAGGA ATCTGCTACC GTTCTGCAA AGACGGCGAG
 651  AAAACTACAT GATTTACAAA AGGACAAAGA ATACGATGGC AATAAATGCT
 701  TTAAAAGTTG TTTGTTGTAC GTTGAAGAGG AAACCTTCAA AAATAAAAAG
 751  CCAGCTCATC TGCAGCTGCC AAAAAATTTA AAAATTGATA AGGAGGCACT
 801  AGATTTAACA GGAGATGAGG ATCTCGAAAA AGATCCGATC AAATTGGACC
 851  CGAGGACAGA AAAATTATCC AAGTTTCTTG ATGACGACAC ATTCCAAAAA
 901  TTCCAAGAAG TGGTTGGTTA CAACCCGCTT CAAGTATTAC GTTATGACTT
 951  AGGCGGAAAA CCTTTGCTAT ATGCCGAAAC AAAAGTCGAT ATTTTAAGCA
1001  CTGTGCCAAG ACCGGGCTAC AACCCATCGA GCCAAAGAAT CTTTGAAATG
1051  CAGTTAATGC CAAAGATGAT TTTTGATCTG GAAGAAGTAG TGTCTGTCGA
1101  TAACGGTATG GAATGGGGTA CCATTCTTGT TTTCACTGAT GTTGAAAATT
1151  ACATGCCTGA ATTTGATGAA CATGGTGTCG GTTATGTAGA AGAATGTGTC
1201  AAAGTTCAGT GGGAATCGAG AACGTGA
```

FIG. 17 yol022cp

```
1   MSKIEELPPS DTDDHSYSSK PGDVFLAFVD APVKETDDIL VEDSFIGGEP
51  KWLHPDSEPP AELLKCGACK SADNMKLLLQ AFSPLDDEQM SAIQQRLGIN
101 NMSYINPQDD RVLYVFLCTE CQRKGNSVRC IRGVKKNKNV DSLSEKMAST
151 SLEKDFQINP FDLSNNSDSK CNAFSSNPFG GANANPFGAD SINSNISQSK
201 DEGKKKESAT VSAKTARKLH DLQKDKEYDG NKCFKSCLLY VEEETFKNKK
251 PAHLQLPKNL KIDKEALDLT GDEDLEKDPI KLDPRTEKLS KFLDDDTFQK
301 FQEVVGYNPL QVLRYDLGGK PLLYAETKVD ILSTVPRPGY NPSSQRIFEM
351 QLMPKMIFDL EEVVSVDNGM EWGTILVFTD VENYMPEFDE HGVGYVEECV
401 KVQWESRT
```

FIG.18 yol022c blastp nr

| Sequences producing significant alignments: | Score (bits) | E Value |
|---|---|---|
| sp\|P25040\|YOC2_YEAST  HYPOTHETICAL 46.0 KD PROTEIN IN IFM1-DIS3 ... | 841 | 0.0 |
| emb\|CAA41269\|  (X58379) orf [Saccharomyces cerevisiae] | 263 | 2e-69 |
| sp\|P87156\|YB0F_SCHPO  HYPOTHETICAL 44.3 KD PROTEIN C25H2.15 IN C... | 127 | 1e-28 |
| gi\|3377805  (AF075597) contains similarity to several apoptosis ... | 58 | 1e-07 |
| pir\|\|S43602  apoptosis protein RP-8 homolog R07E5.10 - Caenorhab... | 54 | 2e-06 |
| sp\|P47816\|RP8_RAT  ZINC FINGER PROTEIN RP-8 >gi\|111391\|pir\|\|A412... | 54 | 2e-06 |
| emb\|CAA83630\|  (Z32683) similar to Apoptosis protein RP-8; cDNA ... | 54 | 2e-06 |
| sp\|P46718\|RP8_MOUSE  ZINC FINGER PROTEIN RP-8 >gi\|2137868\|pir\|\|I... | 53 | 3e-06 |
| emb\|CAA20285\|  (AL031259) PDCD2 (PROGRAMMED CELL DEATH-2/RP8 HOM... | 48 | 1e-04 |
| ref\|NP_002589.1\|PPDCD2\|  programmed cell death 2 >gi\|2135977\|pir... | 46 | 3e-04 |

FIG.19

YOL026C on chromosome XV from coordinates 274353 to 274012.

UPTAG primer:
CCACAAGACAGAAATATGGATGTCCACGAGGTCTCTCATGGATAGTGACCTAGTTGCGTA
CGCTGCAGGTCGAC DOWNTAG primer:
TGCTTTGGTGATCGTTTACGGTGTCGGTCTCGTAGTGCCAGTCTGCATGTCGTTGATCGA
TGAATTCGAGCTCG Upstream45 primer:
AACATCACCCCCCTTCTTACGAAACTGCCACAAGACAGAAATATG Downstream45 primer:
TGTGTATTTATTTATGTAGGTTGCTAATGCTTTGGTGATCGTTTA A primer:     CCAAATATGTCTGCAACGTGTACTA B primer:     GGTACACCTTATACCCCTTGTTTCT C primer:     AACCATAGAAACAAGGGGTATAAGG D primer:     TGATGCGAAATTCAACATCTTAGTA KanB1 primer: TGTACGGGCGACAGTCACAT KanC3 primer: CCTCGACATCATCTGCCCAGAT

FIG. 21 yol026c

```
1    ATGACAGAGG TTGTGGGATT CTGGGAGAGC GTGTCAGATG ACGAATCAGA
51   AGACAAAGAC TGTATGGAGG TGCAGAACAC AGTGAGTGCC GACGAGAGCC
101  CACTTGTGCA GAGCCTTGTA TCCTTTGTAG GCTCGTGCTC CATCAACCTA
151  CTTTTGCCCT TCCTCAACGG CATGATGCTC GGCTTCGGCG AGCTATTTGC
201  TCACGAGCTC TGCTGGAGAT TCAATTGGTT TAACCATAGA AACAAGGGGT
251  ATAAGGTGTA CCCAGAGTCG CGCAAAATAG CAGCATTGAA AGAGATTTCA
301  AGCCCTGGCA CCCGTGGGAG GGTTGCGTCC AAGTTCCTTT AA
```

FIG.22 yol026c

```
1    MTEVVGFWES VSDDESEDKD CMEVQNTVSA DESPLVQSLV SFVGSCSINL
51   LLPFLNGMML GFGELFAHEL CWRFNWFNHR NKGYKVYPES RKIAALKEIS
101  SPGTRGRVAS KFL
```

FIG.23 yol026c blastp nr results

| Sequences producing significant alignments: | Score (bits) | E Value |
|---|---|---|
| pir||S66709  probable membrane protein YOL026c-yeast (Saccharo... | 215 | 8e-56 | pir||S66709 probable membrane protein YOL026c-yeast (Saccharomyces
    cerevisiae) >gi|1419811|emb|CAA99026| (Z74768) ORF
    YOL026c [Saccharomyces cerevisiae]
    Length = 113

Score = 215 bits (542), Expect = 8e-56
Identities = 103/113 (91%), Positives = 103/113 (91%)

```
Query:  1   MTEVVGFWXXXXXXXXXXXXKDCMEVQNTVSADESPLVQSLVSFVGSCSINLLLPFLNGMML 60
            MTEVVGFW            KDCMEVQNTVSADESPLVQSLVSFVGSCSINLLLPFLNGMML
Sbjct:  1   MTEVVGFWESVSDDESEDKDCMEVQNTVSADESPLVQSLVSFVGSCSINLLLPFLNGMML 60

Query: 61   GFGELFAHELCWRFNWFNHRNKGYKVYPESRKIAALKEISSPGTRGRVASKFL 113
            GFGELFAHELCWRFNWFNHRNKGYKVYPESRKIAALKEISSPGTRGRVASKFL
Sbjct: 61   GFGELFAHELCWRFNWFNHRNKGYKVYPESRKIAALKEISSPGTRGRVASKFL 113
```

FIG.24

YOL034W on chromosome XV from coordinates 259923 to 263204

UPTAG primer:
AGCTATATCCCTAGCATGGATGTCCACGAGGTCTCTCTCTATATTGGATGGAGCGTCGTACGCTGCAGGTCGAC DOWNTAG primer:
TGCAATAGTGAAAGATTACGGTGTCGGTCTCGTAGTACCTGCTGCTAGATGGCGTATCGATGAATTCGAGCTCG Upstream45 primer:
ATCAAATAAAAGGGCGTGGTACATAAAAGCTATATCCCTAGCATG Downstream45 primer:
TTACATCTATATGTGTATAATTAATTATGCAATAGTGAAAGATTA A primer:    GATTAACCTTTACAGAACCGCTACA B primer:    GTAACATTTGGTGAATTTTTCAAGG C primer:    GGACTATGCTGAATGGAAGATAGAA D primer:    GATTTCTTCAATGGTGAGAGACCTA KanB1 primer:    TGTACGGGCGACAGTCACAT KanC3 primer:    CCTCGACATCATCTGCCCAGAT

FIG. 26 yol034w

```
1     ATGACCAGTC TAATAGATTT GGGCAGATAT GTTGAAAGAA CGCATCATGG
51    AGAAGATACA GAGCCAAGAT CGAAAAGGGT AAAAATCGCA AAACCTGACT
101   TGTCTTCCTT CCAACCAGGC AGCATTATTA AGATCCGTTT ACAGGATTTT
151   GTTACTTACA CTTTAACCGA ATTCAATCTT TCACCGTCTT TAAATATGAT
201   CATTGGGCCA AACGGATCTG GAAAATCTAC TTTCGTATGC GCAGTGTGTT
251   TAGGATTGGC TGGTAAACCC GAGTATATTG GTAGGAGTAA AAAAGTGGAA
301   GATTTCATCA AAAATGGTCA AGATGTTTCA AAAATTGAAA TCACCTTGAA
351   AAATTCACCA AATGTTACTG ATATTGAATA CATAGACGCA CGTGATGAAA
401   CAATAAAGAT TACCAGGATT ATTACGAGAT CCAAGAGGAG ATCGGATTAT
451   CTAATAAATG ACTACCAGGT ATCTGAGAGT GTAGTTAAAA CTTTAGTTGC
501   TCAGCTGAAC ATTCAGTTGG ATAATCTTTG TCAATTTTTA TCTCAAGAGC
551   GTGTTGAGGA GTTTGCTCGC TTGAAGTCAG TTAAATTATT AGTAGAGACT
601   ATAAGGTCAA TCGATGCAAG CTTATTGGAT GTGTTGGATG AACTAAGGGA
651   ATTACAAGGA AATGAGCAAA GCTTGCAAAA AGATCTCGAT TTTAAAAAAG
701   CTAAAATTGT TCATTTGAGA CAAGAAAGTG ATAAACTACG TAAATCAGTT
751   GAATCTTTAC GAGATTTTCA AAATAAGAAG GGTGAAATCG AGTTACACTC
801   CCAACTATTA CCTTATGTGA AAGTAAAGGA CCATAAAGAA AAGCTAAACA
851   TATATAAAGA AGAATACGAA CGAGCGAAAG CGAACTTAAG GGCTATACTG
901   AAGGATAAAA AACCATTTGC AAATACTAAG AAGACTTTGG AAAATCAGGT
951   GGAAGAGTTA ACAGAGAAGT GTTCCCTAAA AACTGATGAG TTCCTGAAAG
1001  CAAAAGAAAA GATCAACGAA ATCTTCGAAA AATTAAATAC TATTAGGGAT
1051  GAGGTCATCA AAAAGAAAAA CCAGAACGAA TATTATAGAG GAAGAACCAA
1101  AAAACTACAG GCCACCATTA TTAGTACAAA GGAAGATTTT CTAAGGAGTC
1151  AGGAAATATT AGCACAAACA CATCTTCCTG AGAAAAGCGT ATTTGAAGAT
1201  ATAGACATTA AAAGAAAGGA AATTATTAAT AAAGAAGGCG AAATTAGGGA
1251  TCTTATTTCC GAAATTGATG CGAAGGCGAA CGCTATTAAT CATGAGATGA
1301  GAAGCATACA GAGACAAGCT GAAAGCAAGA CCAAATCCCT TACAACAACT
1351  GATAAAATCG GTATCTTAAA TCAGGACCAG GATTTAAAGG AGGTCCGTGA
1401  TGCTGTGTTG ATGGTTAGAG AGCATCCAGA AATGAAAGAT AAAATTCTAG
1451  AACCGCCAAT AATGACCGTG TCTGCCATTA ACGCTCAATT TGCTGCATAT
1501  TTAGCACAAT GTGTGGATTA TAATACGAGT AAAGCCTTGA CTGTTGTTGA
1551  TTCTGATTCT TACAAGCTAT TTGCAAATCC AATTCTTGAC AAATTCAAGG
1601  TTAATTTGAG AGAACTCTCC AGTGCAGACA CCACCCCTCC TGTACCAGCG
1651  GAAACGGTGA GGGACCTGGG ATTTGAGGGT TATCTATCCG ATTTTATTAC
1701  CGGTGATAAG AGGGTTATGA AAATGCTTTG TCAAACTAGC AAAATTCATA
1751  CTATACCGGT ATCAAGAAGG GAATTGACGC CTGCTCAGAT AAAGAAGTTG
1801  ATTACACCAA GACCGAATGG GAAAATTCTT TTTAAAAGGA TTATTCATGG
1851  GAATAGGTTA GTCGATATCA AGCAATCAGC ATATGGTAGT AAGCAGGTCT
1901  TTCCTACTGA CGTTAGTATT AAACAAACTA ATTTTTATCA GGGATCAATC
1951  ATGTCAAATG AGCAGAAAAT TAGAATTGAA AATGAAATTA TCAACTTAAA
2001  GAATGAATAC AACGATCGAA AATCTACGTT AGATGCATTG TCAAACCAGA
```

FIG.27A

```
2051 AAAGTGGTTA TAGGCACGAA TTATCTGAGT TGGCGTCAAA AAACGACGAT
2101 ATTAATAGGG AAGCTCATCA ATTAAATGAG ATTCGCAAGA AGTACACTAT
2151 GAGAAAAAGT ACAATAGAGA CTTTAAGAGA GAAATTAGAT CAACTGAAAC
2201 GTGAAGCTAG AAAGGACGTA TCTCAAAAGA TTAAAGATAT TGATGATCAG
2251 ATCCAACAAC TATTACTCAA GCAAAGACAT TTGCTGTCTA AAATGGCCTC
2301 TTCAATGAAG AGTTTAAAGA ATTGTCAGAA GGAGTTAATA AGTACTCAAA
2351 TCCTTCAATT TGAAGCCCAA AATATGGATG TTTCTATGAA TGACGTAATT
2401 GGTTTTTTCA ATGAGAGGGA AGCTGATTTG AAGAGCCAAT ATGAAGACAA
2451 GAAAAAGTTC GTAAAAGAAA TGAGAGACAC TCCTGAATTT CAATCATGGA
2501 TGAGAGAAAT CAGGTCTTAT GACCAAGACA CTAAGGAAAA ATTGAATAAA
2551 GTGGCAGAAA AATACGAGGA GGAAGGGAAT TTCAATCTGT CATTCGTTCA
2601 GGATGTTCTC GATAAATTAG AATCGGAGAT AGCTATGGTA AACCACGACG
2651 AGTCAGCCGT AACAATTTTG GATCAAGTCA CAGCCGAACT GAGAGAGTTG
2701 GAGCACACGG TTCCTCAGCA GTCGAAAGAC TTGGAGACCA TTAAAGCTAA
2751 ATTAAAAGAA GATCACGCAG TTTTGGAGCC CAAATTAGAT GATATTGTAT
2801 CAAAAATCTC TGCAAGATTT GCGCGCTTAT TCAACAATGT TGGGAGTGCT
2851 GGTGCGGTTC GTCTAGAAAA GCCGAAGGAC TATGCTGAAT GGAAGATAGA
2901 AATCATGGTA AAATTCAGAG ATAATGCACC TTTAAAAAAG TTAGATTCCC
2951 ACACGCAATC AGGTGGTGAA AGAGCTGTTT CTACAGTTCT TTACATGATT
3001 GCTTTGCAAG AGTTTACCTC TGCACCATTT AGAGTGGTTG ATGAAATCAA
3051 TCAAGGTATG GACTCTAGAA ATGAAAGGAT CGTTCATAAA GCTATGGTGG
3101 AGAACGCGTG TGCCGAAAAC ACTTCTCAAT ATTTTTTAAT CACTCCAAAA
3151 TTATTGACTG GCTTGCATTA TCATGAAAAG ATGAGAATAC ACTGTGTCAT
3201 GGCTGGTTCT TGGATTCCAA ACCCTTCTGA GGATCCGAAG ATGATACATT
3251 TCGGTGAAAC TTCTAACTAC TCATTCGATT AA
```

FIG.27B yo1034wp

```
   1  MTSLIDLGRY VERTHHGEDT EPRSKRVKIA KPDLSSFQPG SIIKIRLQDF
  51  VTYTLTEFNL SPSLNMIIGP NGSGKSTFVC AVCLGLAGKP EYIGRSKKVE
 101  DFIKNGQDVS KIEITLKNSP NVTDIEYIDA RDETIKITRI ITRSKRRSDY
 151  LINDYQVSES VVKTLVAQLN IQLDNLCQFL SQERVEEFAR LKSVKLLVET
 201  IRSIDASLLD VLDELRELQG NEQSLQKDLD FKKAKIVHLR QESDKLRKSV
 251  ESLRDFQNKK GEIELHSQLL PYVKVKDHKE KLNIYKEEYE RAKANLRAIL
 301  KDKKPFANTK KTLENQVEEL TEKCSLKTDE FLKAKFKINE IFEKLNTIRD
 351  EVIKKKNQNE YYRGRTKKLQ ATIISTKEDF LRSQEILAQT HLPEKSVFED
 401  IDIKRKEIIN KEGEIRDLIS EIDAKANAIN HEMRSIQRQA ESKTKSLTTT
 451  DKIGILNQDQ DLKEVRDAVL MVREHPEMKD KILEPPIMTV SAINAQFAAY
 501  LAQCVDYNTS KALTVVDSDS YKLFANPILD KFKVNLRELS SADTTPPVPA
 551  ETVRDLGFEG YLSDFITGDK RVMKMLCQTS KIHTIPVSRR ELTPAQIKKL
 601  ITPRPNGKIL FKRIIHGNRL VDIKQSAYGS KQVFPTDVSI KQTNFYQGSI
 651  MSNEQKIRIE NEIINLKNEY NDRKSTLDAL SNQKSGYRHE LSELASKNDD
 701  INREAHQLNE IRKKYTMRKS TIETLREKLD QLKREARKDV SQKIKDIDDQ
 751  IQQLLLKQRH LLSKMASSMK SLKNCQKELI STQILQFEAQ NMDVSMNDVI
 801  GFFNEREADL KSQYEDKKKF VKEMRDTPEF QSWMREIRSY DQDTKEKLNK
 851  VAEKYEEEGN FNLSFVQDVL DKLESEIAMV NHDESAVTIL DQVTAELREL
 901  EHTVPQQSKD LETIKAKLKE DHAVLEPKLD DIVSKISARF ARLFNNVGSA
 951  GAVRLEKPKD YAEWKIEIMV KFRDNAPLKK LDSHTQSGGE RAVSTVLYMI
1001  ALQEFTSAPF RVVDEINQGM DSRNERIVHK AMVENACAEN TSQYFLITPK
1051  LLTGLHYHEK MRIHCVMAGS WIPNPSEDPK MIHFGETSNY SFD
```

FIG.28 yol034wp blastp    nr

Sequences producing significant alignments:

| | Score (bits) | E Value |
|---|---|---|
| pir\|\|S66717  hypothetical protein YOL034w - yeast (Saccharomyces... | 2059 | 0.0 |
| emb\|CAB11195\|  (Z98596) SMC-family protein [Schizosaccharomyces ... | 364 | 2e-99 |
| sp\|O13710\|YDZ2_SCHPO  HYPOTHETICAL 123.7 KD PROTEIN C14C4.02 IN ... | 360 | 2e-98 |
| dbj\|BAA25520\|  (AB011166) KIAA0594 protein [Homo sapiens] | 229 | 1e-58 |
| gi\|1330388  (U58760) coded for by C. elegans cDNA yk34f2.3; code... | 213 | 5e-54 |
| gi\|2826443  (U67604) chromosome segretation protein (smc1) [Meth... | 105 | 2e-21 |
| pir\|\|A64505  P115 homolog - Methanococcus jannaschii | 102 | 9e-21 |
| pir\|\|JQ0894  P115 protein - Mycoplasma hyorhinis (SGC3) | 98 | 4e-19 |
| sp\|P41508\|P115_MYCHR  P115 PROTEIN >gi\|150165 (M34956) 115 kDa p... | 96 | 1e-18 |
| pir\|\|S65799  chromosome scaffold protein sudA - Emericella nidul... | 93 | 1e-17 |
| pir\|\|S30782  integrin homolog - yeast (Saccharomyces cerevisiae) | 92 | 1e-17 |
| gi\|677198  (L03188) putative [Saccharomyces cerevisiae] | 92 | 1e-17 |
| pir\|\|S67593  transport protein USO1 - yeast (Saccharomyces cerev... | 91 | 4e-17 |
| sp\|P25386\|USO1_YEAST  INTRACELLULAR PROTEIN TRANSPORT PROTEIN US... | 91 | 4e-17 |
| emb\|CAA98620\|  (Z74105) ORF YDL058w [Saccharomyces cerevisiae] | 91 | 4e-17 |
| emb\|CAB01681\|  (Z78416) predicted using Genefinder; Similarity t... | 90 | 9e-17 |
| dbj\|BAA30025\|  (AP000004) 879aa long hypothetical purine NTPase ... | 85 | 2e-15 |
| sp\|Q12749\|RH18_YEAST  DNA REPAIR PROTEIN RHC18 (RAD18 HOMOLOG) >... | 85 | 2e-15 |
| gi\|1850913  (L03534) myosin heavy chain [Entamoeba histolytica] | 84 | 4e-15 |
| emb\|CAB16920\|  (Z99771) cDNA EST EMBL:D33404 comes from this gen... | 84 | 5e-15 |
| gi\|2649004  (AE000995) chromosome segregation protein (smc1) [Ar... | 83 | 9e-15 |
| gi\|2983243  (AE000699) chromosome assembly protein homolog [Aqui... | 82 | 2e-14 |
| sp\|P41004\|CUT3_SCHPO  CHROMOSOME SEGREGATION PROTEIN CUT3 >gi\|10... | 80 | 6e-14 |
| emb\|CAA71688\|  (Y10687) purine NTPase [Sulfolobus acidocaldarius] | 80 | 6e-14 |
| pir\|\|A64465  hypothetical protein MJ1322 - Methanococcus jannasc... | 80 | 8e-14 |
| dbj\|BAA30917.1\|  (AP000007) 1179aa long hypothetical chromosome ... | 78 | 2e-13 |
| sp\|P53692\|RA18_SCHPO  DNA REPAIR PROTEIN RAD18 >gi\|1150622\|emb\|C... | 77 | 7e-13 |
| sp\|P38989\|SMC2_YEAST  CHROMOSOME SEGREGATION PROTEIN SMC2 (DA-BO... | 76 | 1e-12 |
| sp\|P47540\|P115_MYCGE  P115 PROTEIN HOMOLOG >gi\|1361771\|pir\|\|I642... | 75 | 3e-12 |
| sp\|P75361\|P115_MYCPN  P115 PROTEIN HOMOLOG >gi\|2146486\|pir\|\|S737... | 75 | 3e-12 |
| emb\|CAB13467\|  (Z99112) chromosome segregation SMC protein homol... | 75 | 3e-12 |
| ref\|NP_001804.1\|PCENPE\|  centromere protein E >gi\|399227\|sp\|Q022... | 74 | 4e-12 |
| sp\|P50533\|XCPE_XENLA  CHROMOSOME ASSEMBLY PROTEIN XCAP-E >gi\|107... | 73 | 8e-12 |

FIG.29

```
dbj|BAA25520| (AB011166) KIAA0594 protein [Homo sapiens]
           Length = 882, Score =  229 bits (577), Expect = 1e-58
 Identities = 220/917 (23%), Positives = 409/917 (43%), Gaps = 119/917 (12%)

Query: 222  EQSLQKDLDFKKAKIVHLRQESDKLRKSVESLRDFQNKKGEIELHSQLLPYVKVKDHKEK 281
            E+ L+       K   + + Q +++ ++ VE   + +    IE+     P+V+ ++ +++
Sbjct: 3    EKQLETSCKEKTEYLQKMVQRNERYKQDVERFYERKRHLDLIEMLEAKRPWVEYENVRQE 62

Query: 282  LNIYKEEYERAKANLRAILKDKKPFANTKKTLENQVEELTEKCSLKTDEFLKAKEKINEI 341
                K   +R K  +R + + + P    + +EN+   L  ·   K   +A +K  +
Sbjct: 63   YEEVKLVRDRVKEEVRKLKEGQIPITCRIEEMENERHNLEARIKEKATDIKEASQKCKQ- 121

Query: 342  FEKLNTIRDEVIKKKNQNEYYRGRTKKLQATIISTKEDFLRSQEILAQTHLPEKSVFEDI 401
                  + +VI++K+++       ++LQ  +I + + L  Q  +    + + ED+
Sbjct: 122  --------KQDVIERKDKH------IEELQQALIVKQNEELDRQRRIGNT----RKMIEDL 164

Query: 402  DIKRKEIINKEGEIRDLISEIDAKANAINH----------EMRSIQRQAESKTKSLTTTD 451
             + K   N E   +L  +IDA  N +              E+   +R+ E+   K   + D
Sbjct: 165  QNELKTTENCE----NLQPQIDAITNDLRRIQDEKALCEGEIIDKRRERETLEKEKKSVD 220

Query: 452  KI-----GILNQDQD-----LKEVRDAVLMVREHPE-MKDKILEPPIMTVSAINAQFAAY 500
                    ++NQ +D        ++  DAVL +R + +   K ++ EP ++T++  + + A Y
Sbjct: 221  DHIVRFDNLMNQKEDKLRQRFRDTYDAVLWLRNNRDKFKQRVCEPIMLTINMKDNKNAKY 280

Query: 501  LAQCVDYNTSKALTVVDSDSYKLFANPILDKFKVNLREL------SSADTTPPVPAETVRD 555
            +   +  N  +A      +   ++F    D K++  +         S AD   P         ++
Sbjct: 281  IENHIPSNDLRAFVFESQEDMEVFLKEVRDNKKLRVNAVIAPKSSYADKAPSRSLNELKQ 340

Query: 556  LGFEGYLSDFITGDKRVMKMLCQTSKIHTIPVSRRELTPAQIKKLITPRPNGKILFKRII 615
              GF  YL +       VM  LC     IH +PV      E T   +I+++I     +  K+I
Sbjct: 341  YGFFSYLRELFDAPDPVMSYLCCQYHIHEVPVGT-EKTRERIERVIQ-----ETRLKQIY 394

Query: 616  HGNRLVDIKQSAYGSKQVFPTDVSIKQTNFYQGSIMSNEQKIRIENEIINLKNEYNDRKS 675
                +K S Y +K V  ++ S+K  F   ++   EQ+ +E ++  +         S
Sbjct: 395  TAEEKYVVKTSFYSNK-VISSNTSLKVAQFLTVTV-DLEQRRHLEEQLKEIHRKLQAVDS 452

Query: 676  TLDALSNQKSGYRHELSELASKNDDINREAHQLNEIRKKYTMRKSTIETLREKLDQLKRE 735
             L AL         H+ +EL K ++     + ++ +K + +    +++ + +    L+ E
Sbjct: 453  GLIALRETSKHLEHKDNELRQKKKELLERKTKKRQLEQKISSKLGSLKLMEQDTCNLEEE 512

Query: 736  ARKDVSXXXXXXXXXXXXXXXXXRHXXXXXXXXXXXXXXNCQKELISTQILQF-------E 788
             RK                                      N QK  + T++
Sbjct: 513  ERK-------------------------------ASTKIKEINVQKAKLVTELTNLIKICTSLH 545
```

FIG.30A

```
Query:  789  AQNMDVSMND--VIGFFNEREADLKSQYEDKKKFVKEMRDTPEF-QSWMREIRSYDQDTK  845
             Q +D+ + +  VI    N+ E+D +      +    +   + E Q +++ +   + +
Sbjct:  546  IQKVDLILQNTTVISEKNKLESDYMAASSQLRLTEQHFIELDENRQRLLQKCKELMKRAR  605

Query:  846  EKLNKVAEK-----YEEE-------GNFNLSFV-QDVLDKLESEIAMVNHDESAVTILD-  891
             +  N  AE+     Y+ +        N +L V QD+ + L+   A++  + S    +
Sbjct:  606  QVCNLGAEQTLPQEYQTQVPTIPNGHNSSLPMVFQDLPNTLDEIDALLTEERSRASCFTG  665

Query:  892  ---QVTAELRELEHTVPQQSKDLETIKAKL----KEDHAVLEPK----LDDIVSKISARFA  941
                + E + E + Q +++L+  K +L   +E+ +  ++ +     L ++V KI+ +F+
Sbjct:  666  LNPTIVQEYTKREEEIEQLTEELKGKKVELDQYRENISQVKERWLNPLKELVEKINEKFS  725

Query:  942  RLFNNVGSAGAVRL--EKPKDYAEWKIEIMVKFRDNAPLKKLDSHTQSGGERAVSTVLYM  999
              F+++   AG V L  E  +DY ++  I I VKFR +  L +L H QSGGER+VST+LY+
Sbjct:  726  NFFSSMQCAGEVDLHTENEEDYDKYGIRIRVKFRSSTQLHELTPHHQSGGERSVSTMLYL  785

Query: 1000  IALQEFTSAPFRVVDEINQGMDSRNERIVHKAMVENACAENTSQYFLITPKLLTGLHYHE 1059
             +ALQE    PFRVVDEINQGMD  NER V + +V  AC ENTSQYF ITPKLL  L Y E
Sbjct:  786  MALQELNRCPFRVVDEINQGMDPINERRVFEMVVNTACKENTSQYFFITPKLLQNLPYSE  845

Query: 1060  KMRIHCVMAGSWIPNPS 1076
             KM +  V G + P+
Sbjct:  846  KMTVLFVYNGPHMLEPN 862
```

FIG.30B

YOL077C on chromosome XV from coordinates 186722 to 185847

UPTAG primer:
AGAGTTCAACCAAAGATGGATGTCCACGAGGTCTCTAGTGAGCGCCTCGCATCTATCGTACGCTGCAGGTCGAC DOWNTAG primer:
ATAGTATTATGCTTATTACGGTGTCGGTCTCGTAGAGGCCATGCTTCCATAGTATATCGATGAATTCGAGCTCG Upstream45 primer:
TTCTTTATACATTCGTCAGGTGTTGAAAGAGTTCAACCAAAGATG Downstream45 primer:
ATATACAATGTTATGTAAAACTCTCTGATAGTATTATGCTTATTA A primer:    AGTTTTGCATAGCATTGTTTGAAGT B primer:    CTACAATACTGAAGGACATGACGTG C primer:    AGATGATAAAATATGGGTGAGGACA D primer:    TTATTGGTTGTTCCAAATCCTTTTA KanB1 primer:    TGTACGGGCGACAGTCACAT KanC3 primer:    CCTCGACATCATCTGCCCAGAT

FIG.32 yol077c

```
1    ATGTCTTCTA TCTACAAAGC CCTCGCAGGA AAGAGCAAAG ATAATAAATC
51   TGAAAAGAAG CAAGGCAATG TCAAGCAATT TATGAACAAG CAAAGAACTC
101  TTCTGATTTC GAGTAGAGGT GTTAACTATA GACATCGTCA TTTAATTCAA
151  GACTTAAGCG GATTATTGCC TCATTCCAGA AAGGAGCCAA AATTGGATAC
201  TAAAAAGGAT CTTCAACAGT TGAACGAAAT CGCTGAGTTG TACAATTGTA
251  ATAATGTTCT ATTCTTTGAG GCCAGAAAAC ACCAAGATTT GTATCTATGG
301  TTATCCAAGC CGCCAAATGG GCCAACTATA AAATTTTACA TTCAAAACTT
351  GCATACTATG GATGAGTTGA ATTTTACAGG TAACTGTTTA AAGGGTTCTC
401  GTCCGGTATT GTCGTTTGAT CAACGTTTCG AATCCTCCCC ACACTACCAA
451  TTAATTAAGG AGTTGCTAGT GCATAATTTT TGTGTACCAC CAAATGCTAG
501  AAAATCTAAG CCATTTATTG ATCACGTCAT GTCCTTCAGT ATTGTAGATG
551  ATAAAATATG GGTGAGGACA TATGAGATCT CACACAGTAC TAAGAACAAA
601  GAAGAATATG AAGATGGCGA AGAAGACATA TCATTAGTGG AAATTGGCCC
651  TAGGTTTGTT ATGACTGTCA TTTTGATCCT AGAAGGTTCA TTTGGTGGTC
701  CAAAGATCTA TGAAAATAAA CAATATGTTT CGCCAAACGT CGTAAGAGCT
751  CAAATTAAAC AACAAGCTGC TGAGGAGGCA AAGTCTAGAG CTGAAGCTGC
801  TGTGGAAAGA AAAATTAAGA GAAGAGAGAA TGTTCTTGCC GCCGATCCTT
851  TATCAAACGA TGCCTTGTTT AAATAA
```

FIG.33 yol077cp

```
1    MSSIYKALAG KSKDNKSEKK QGNVKQFMNK QRTLLISSRG VNYRHRHLIQ
51   DLSGLLPHSR KEPKLDTKKD LQQLNEIAEL YNCNNVLFFE ARKHQDLYLW
101  LSKPPNGPTI KFYIQNLHTM DELNFTGNCL KGSRPVLSFD QRFESSPHYQ
151  LIKELLVHNF CVPPNARKSK PFIDHVMSFS IVDDKIWVRT YEISHSTKNK
201  EEYEDGEEDI SLVEIGPRFV MTVILILEGS FGGPKIYENK QYVSPNVVRA
251  QIKQQAAEEA KSRAEAAVER KIKRRENVLA ADPLSNDALF K
```

FIG.34 yol077c
blastp    nr    results

| Sequences producing significant alignments: | Score (bits) | E Value |
|---|---|---|
| pir\|\|S66770  probable membrane protein YOL077c - yeast (Saccharo... | 548 | e-155 |
| sp\|P34524\|YM63_CAEEL  HYPOTHETICAL 40.2 KD PROTEIN K12H4.3 IN CH... | 221 | 4e-57 |
| gi\|3695379  (AF096370) contains similarity to a C. elegans hypot... | 42 | 0.006 |
| emb\|CAB11643\|  (Z98974) hypothetical protein [Schizosaccharomyce... | 38 | 0.11 |
| emb\|CAA15609.1\|  (AL008970) predicted using hexExon; MAL3P4.19 (... | 37 | 0.15 |
| gb\|AAD16459\|  (AF102805) Peter Pan [Drosophila melanogaster] | 36 | 0.33 |
| emb\|CAA93858\|  (Z70034) similarity to 35.1KD hypothetical yeast ... | 35 | 0.75 |
| sp\|P47615\|SYT_MYCGE  THREONYL-TRNA SYNTHETASE (THREONINE--TRNA L... | 33 | 2.2 |
| sp\|O14180\|YDS4_SCHPO  HYPOTHETICAL 35.8 KD PROTEIN C4F8.04 IN CH... | 33 | 2.2 |
| emb\|CAB11063\|  (z98531) hypothetical protein [Schizosaccharomyce... | 33 | 2.2 |
| gi\|1098998  (U41510) coded for by C. elegans cDNA yk85d4.5; Sim... | 33 | 2.9 |
| sp\|O04904\|PYRC_ARATH DIHYDROOROTASE PRECURSOR (DHOASE) >gi\|2121... | 33 | 2.9 |
| emb\|CAB03164\|  (Z81096) cDNA EST EMBL:D27854 comes from this gen... | 32 | 3.8 |
| pir\|\|C45561  merozoite surface antigen (clone 9) - Babesia bigemina | 32 | 6.5 |
| gi\|2318123  (AF014486) rhoptry associated protein-1 (Babesia big... | 32 | 6.5 |
| pir\|\|B45561  merozoite surface antigen (clone 7) - Babesia bigemina | 32 | 6.5 |
| sp\|P53941\|YNH5_YEAST  HYPOTHETICAL 33.5 KD PROTEIN IN MKS1-MSK1 ... | 31 | 8.5 |

FIG.35

```
yol077cp
blastp       nr
                                                              Score      E
Sequences producing significant alignments:                   (bits)   Value pir||S66770    probable membrane protein YOL077c - yeast (Saccharo...   548   e-155
sp|P34524|YM63_CAEEL HYPOTHETICAL 40.2 KD PROTEIN K12H4.3 IN CH...       221   4e-57 sp|P34524|YM63_CAEEL HYPOTHETICAL 40.2 KD PROTEIN K12H4.3 IN CHROMOSOME III
          >gi|630687|pir||S44853 K12H4.3 protein - Caenorhabditis
          elegans >gi|289707 (L14331) coded for by C. elegans
          cDNAs GenBank:  CE5D1 (Z14791), CEL01F1 (M88817),
          CEL04B5(M88849), and CEL04C1(M75812); putative
          [Caenorhabditis elegans]
          Length = 352

Score =  221 bits (558), Expect = 4e-57
 Identities = 103/234 (44%), Positives = 155/234 (66%), Gaps = 13/234 (5%)

Query:  17  SEKKQGNVKQFMNKQRTLLISSRGVNYRHRHLIQDLSGLLPHSRKEPKLDTKKDLQQLNE  76
            +E+ +    + + N++R L++ SRG + R R+L++D+   LLPH++ + KLD +K L  LNE
Sbjct:  49  TEETRKRAELWTNRERVLVLCSRGADVRTRYLMKDIKDLLPHAKGDSKLDQQKSLNVLNE  108

Query:  77  IAELYNCNNVLFFEARKHQDLYLWLSKPPNGPTIKFYIQNLHTMDELNFTGNCLKGSRPV  136
            IAE+  NC  V++FE+RK +D YLW+S     GP+IKF + N+HTM EL  +GNCL+  SRPV
Sbjct: 109  IAEMKNCTKVMYFESRKRKDTYLWMSNVEKGPSIKFLVHNVHTMKELKMSGNCLRASRPV  168

Query: 137  LSFDQRFESSPHYQLIKELLVHNFCVPPNARKSKPFIDHVMSFSIVD-DKIWVRTYEISH  195
            LSFD  F+  P  +LIK +L+     P +  +S+PF+DHV +FS+   DKIW R ++I
Sbjct: 169  LSFDDAFDKKPQLKLIKAVLMQTLGTPHHHPRSQPFVDHVFNFSVGEGDKIWFRNFQIV-  227

Query: 196  STKNKEEYEDGEEDISLVEIGPRFVMTVILILEGSFGGPKIYENKQYVSPNVVR  249
                        +E + L E+GPRFV+ ++ +   GSF G  +Y+N   YVSPNV+R
Sbjct: 228  -----------DESLQLQEVGPRFVLEMVRLFAGSFEGAVLYDNPNYVSPNVIR  270
```

FIG. 36

Blast Results from Yeast Protein Database, Proteome, Inc.
Report generated 04 May 1999, 10:57 AM

BLAST Alignments for YOL077C vs C.albicans fragments        HITS
385015C06.y1.seq 385029E10.y1.seq 384192F11.s1.seq            3

Query Results for: YOL077c/01115 Protein with similarity to
C. elegans Kq2H4.3 protein (Length = 291)
Compared with C. albicans fragments protein sequences
(Documentation)

| Gene | Gene Bank | Synonyms/Description | Match Length | % Iden | % Sim | High Score | E Val |
|---|---|---|---|---|---|---|---|
| 385015C06.y1.seq | | 385015C06.y1.seq YOL77 | 143 | 73% | 83% | 576 | 3e-52 |
| 385029E10.y1.seq | | 385029E10.y1.seq No Description | 96 | 62% | 75% | 323 | 8e-26 |
| 384192F11.s1.seq | | 384192F11.s1.seq No Description | 79 | 62% | 75% | 254 | 2e-16 |

385015C06.y1.seq YOL77
Score = 576   Length = 209   Expect = 3e-52   Frame = +3
Identities = 104/143 (73%) Similarities = 119/143 (83%)
```
Query 1     MSSIYKALAGKSKDNKSEKKQGNVKQFMNKQRTLLISSRGVNYRHRHLIQDLSGLLPHSR   60
            MS+IYKAL  KS    SEK +      +N+QR L+ISSRG+ YRHRHLIQDL  LLPH+R
Sbjct 46    MSAIYKALQSKSSKETSEKTK-----HINRQRLLVISSRGITYRHRHLIQDLLALLPHAR  100

Query 61    KEPKLDTKKDLQQLNEIAELYNCNNVLFFEARKHQDLYLWLSKPPNGPTIKFYIQNLHTM  120
            KEPK D+KK+L QLNE+AELYNCNN+ FFE RKHQDLYLW+SKPPNGPT KF+IQNLHT+
Sbjct 101   KEPKFDSKKNLHQLNEVAELYNCNNIFFFECRKHQDLYLWISKPPNGPTXKFMIQNLHTL  160

Query 121   DELNFTGNCLKGSRPVLSFDQRF  143
            DELNFTGNCLKGSRP LSFD+ F
Sbjct 161   DELNFTGNCLKGSRPNLSFDKSF  183
```

385029E10.y1.seq No Description
Score = 323   Length = 177   Expect = 8e-26   Frame = +3
Identities = 60/96 (63%) Similarities = 72/96 (75%)
```
Query 1     MSSIYKALAGKSKDNKSEKKQGNVKQFMNKQRTLLISSRGVNYRHRHLIQDLSGLLPHSR   60
            MS+IYKAL  KS    SEK +      +N+QR L+ISSRG+ YRHRHLIQDL  LLPH+
Sbjct 77    MSAIYKALQSKSSKETSEKTK-----HINRQRLLVISSRGITYRHRHLIQDLLALLPHA*  131

Query 61    KEPKLDTKKDLQQLNEIAELYNCNNVLFFEARKHQD  96
            KEPK D+KK+L QLNE+AELYNCNN+ FFE  KH +
Sbjct 132   KEPKFDSKKNLHQLNEVAELYNCNNIFFFECGKHHE  167
```

384192F11.s1.seq No Description
Score = 254   Length = 109   Expect = 2e-16   Frame = +2
Identities = 49/79 (62%) Similarities = 59/79 (75%)
```
Query 1     MSSIYKALAGKSKDNKSEKKQGNVKQFMNKQRTLLISSRGVNYRHRHLIQDLSGLLPHSR   60
            MS+ YKAL  KS    SEK +      +N+QR L+ISSRG+ YRHRHLIQDL  LLPH+R
Sbjct 33    MSANYKALQSKSSKETSEKTK-----HINRQRLLVISSRGITYRHRHLIQDLLALLPHAR   87

Query 61    KEPKLDTKKDLQQLNEIAE   79
            KEPK D+KK+L QLNE+AE
Sbjct 88    KEPKFDSKKNLHQLNEVAE  106
```

FIG.37

```
                           SEQUENCE LISTING

<160> NUMBER OF SEQ ID NOS: 62

<210> SEQ ID NO 1
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 1
gaggatcgac aaaaaatgga tgtccacgag gtctctgata cccgcacatt tgtttccgta     60
cgctgcaggt cgac                                                      74

<210> SEQ ID NO 2
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 2
aattcatagc tatgctcacg gtgtcggtct cgtaggatag gtccctcaga cgactatcga     60
tgaattcgag ctcg                                                      74

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 3
aaaagccgac agagcagctt tttctgagag gatcgacaaa aaatg                    45

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 4
ataactatat ttcggtttat aaagaaaaat tcatagctat gctca                    45

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 5
ggaatattta gagtccgatt accgt                                          25

<210> SEQ ID NO 6
<211> LENGTH: 25
```

```
<212> TYPE: DNA
<213> ORGANISM: Artificial Sequence
<220> FEATURE:
<223> OTHER INFORMATION: Description of Artificial Sequence: primer

<400> SEQUENCE: 6
aatgtgacct aacagacata gaggc                                           25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 7
catatttgtt gcactttcc tcttt                                            25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 8
atggcgatta ctgataaact gctac                                           25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 9
tgtacgggcg acagtcacat                                                 20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 10
cctcgacatc atctgcccag at                                              22

<210> SEQ ID NO 11
<211> LENGTH: 5097
<212> TYPE: DNA
<213> ORGANISM: Saccharomyces cerevisiae

<400> SEQUENCE: 11
atgtccttac cactaaagcc ccttacaatt gactcaaata ataaacaact agactccaaa     60
cagaagaagt ttcgtgctaa tgtcgagcga gcattagaaa gatttgactc tgtaacagaa    120
tgggcggact atattgctag tttgggaaca ctattaaagg cgttgcaaag ctggtcacct    180
aaatttcaga atgtaaggta ctatgttcct tctccatatc aagtaagtcg aagattgaca    240
tcctcattat cgccggcgtt accagcaggt gttcatcaga aactttaga agtatatacg     300 tatatctttg aacatattgg ccttgaaact ctggctacag aatgtaacat ttggatcccg    360
ggaattttac ctttgatgac ttatgcctct atgtctgtta ggtcacattt gatagagctt    420
```

-continued

| | | |
|---|---|---|
| tacgataact atatccttct gttgcctcaa acaacgttaa gactgctcat cagacctttg | 480 |
| atttctagtt tattgccagg aattgatgat gaaagcaacg attttttacc tttaacttta | 540 |
| aaactcattg agactctgca ggagaacttg gatgatgatt ccttattttg gcaaacgttg | 600 |
| tttctagtca tgactgcaaa taaaggcaga agactgggcg gactcacgtg gttgactaga | 660 |
| aagtttccgt cgttgaatgc tgtacctcat ctagtaaata aaataaaaat ggaagcggaa | 720 |
| gagaacccaa gtgaaactga accaacgat tctcatctag acaggaaaaa aagaaaagaa | 780 |
| gaagctttca aggtcttatt gcctgctgcc aaagatttag taaccctga accaggtcta | 840 |
| cttatccgat gccttgtcgg ttgtttagaa gatgaaaatg atattcttat taaaaggagc | 900 |
| gttttggacc ttttattaca gaggttgagg ctagactctc ccgttttgaa tgttcttatt | 960 |
| acttctgagg ataaaaagtt attgataatg agttgttgta gaactacttt gagcaaggat | 1020 |
| atgtctttga acagaagaat atggaactgg cttctcggtc ctactgctgg gggcatgcta | 1080 |
| aacaataacg gcgggaactc catggaatat actacctcgg ttaagtcagc aaacgaggaa | 1140 |
| agtaatgtat atttttacaaa atatggatta agcgcccttt tagaaggttt aagcgacctt | 1200 |
| ctttcagaag aagaatccgt gttaactgca ttcaggataa gtatggcagt aatggataga | 1260 |
| tgggaaattg gctcacttgt aattcctgaa ttgttcatcc cacttctcta ttcctcggaa | 1320 |
| aaatttaaac aaaacgaaca aataatgaaa acggcacgta ctttctttga caatactgaa | 1380 |
| acaaatatta tatggggaaa gctatttcaa gaacttgaag acatcaaaaa cctaaaaatt | 1440 |
| ttggatttcg tattaacaaa ttttaatatt ggaaacgacg aagagattat cgtacgccac | 1500 |
| cttcctttga tattattaac tttactggcc cttccatcta atgataaaga tttcgacaat | 1560 |
| atttataagc tccaaaaatt ttctttgtac aacaaattgt taaactatat ccccgagaga | 1620 |
| gcccttctcc ctctcagtca ctcaaaacta agcacgatg atgaagtaag ctgcgaagaa | 1680 |
| cttttggcca aaatacgtgg gttttatacc aatgtttcta atccatctag cattttagag | 1740 |
| aaagaaaata tagctgagcg tttgccaccc tttacaacag aagatctaac tttttttaata | 1800 |
| gcagacctga ttcagaagaa gcttctttca gtttatggg acttgaaaaa tatcaatgaa | 1860 |
| agctccaaat tatttatagc tattttcgaa aagatacctg agtctgaaga acttaaagga | 1920 |
| cgatctcaca taagctggtc ggataaaaaa ataactcaga gcatatttga ggctattccc | 1980 |
| aggctttgtg aatctaataa tgatgcaaaa tcagaagaaa tcgttggaat tgtggaaatt | 2040 |
| tttggtaact acttatattc acgcatggaa ttcattgaat cgatgaaatt attgaaagta | 2100 |
| gtcatgatgg ccgtatggaa atctttaaaa gatccacgcc atcaaatact aggtgtcaag | 2160 |
| aacttaaaga ctttaaacag atttattcca tccaaattta ttgaaagtgc gttagtgtat | 2220 |
| actttgtgg aagaggaaga tatatccgag agattaagcg tgttagatct gttatggaca | 2280 |
| caattagact cagattcaaa cttgattagg cgccctcttg aattaatttt gggcgaactt | 2340 |
| tttgatgacc agaatccttt ttatttaacc gtttcaaagt ggatttttatc gatattaaac | 2400 |
| tcgggatctg cttcaagatt attttacatt ttgactgata atattttaaa ggttaatcgt | 2460 |
| ctcgaaaaag aaagattaga cgaaagggat gatcttgata tgctcacata tgagttccaa | 2520 |
| atgcttgctt atgttttgaa aacaaacaat ggacgcacta ggaaagtttt ttccactgag | 2580 |
| cttacctcaa taaaatcttc gaccatatgg aagaatgaag acgtttccac atataaaagt | 2640 |
| tgctgttgg ttacattgat gagatttcta aatataaaga gcaatacaca tgcgaaaagt | 2700 |
| atcaggagtg ctctgattct tttggatatc ttactcgatg gaactgagca aaatttcaag | 2760 |
| gacattgtca tattttttgct gcaaatgtcg tctaaatata ttgcagaaga aggaattgag | 2820 |

```
cccgagttaa tagcagtttc cttgttagat attgtatcga aggttctcag actatcacac    2880
gataatggta ttaaactaga cattttgat gacaatgctg cccattaaa atatatcgat     2940 ttccttgtta ccagcgtttc aaatatgaaa agccctctta ttgtaacggc ctatgtgaag    3000
cttctttccg aaagcattgt ttattttgag aattctatat ttcgaatgat tttaccattg    3060
tctgcatctc ttgtacagtg tgttcagaga ttgttttgc tagaaaagag agaaggtggt     3120
tattaccaac caatagcttt gcttctgggt ggtctggaag agctattaga gatttcacat    3180
ggttaccttg tcaccgagga aagggaagga tacttttctg ggtctaatct aaagggtgat    3240
tttattcaat ccgttgtttc aaacgttttt tcgtcagatt cttccaatga agaaagtaag    3300 attcagggg aaagagacgt aatactacaa tctttcagac aggtgatttc atgctgttta    3360
gatatctggt attgggccca taacatttcg tgtaaatcta acgatgattc tagcctggac    3420
gccactaatc ataactcata caagttcaaa tttaggtcga agaaactgtt ggaaacctta    3480
tttctactag aacctttgga acttctggaa aatttgatca gcattagatc agacaatact    3540
acagtcacac tagtacatgt gctcgacggc aataaacccg ccattacaat accacattta    3600
ttgtatggtg taattatcag atacaacaga acggcatctg tcaagtttc taatcgtgac    3660 ggaagtaggc caagcacaac taaattaact aaaggggagc cttccatgtt aaaaagatta    3720
agcggggaat cgattattgc attttgttt aactacgtgg attctgtaga aaactctgca    3780
atggaggagt tttatggga tttcctgcta tttttcagag aagtagcaac caattataac    3840
ctttattctg atgtttcgtt gtctatatta aaacttgttg cccttatttc tggaaaagta    3900
agtaaaacgc agtttggaga acaaaaacga gttaggaggg agatatctga tgtgtttttc    3960
aaatacctac ctaatgcatt tataaacttt acgaacttat atcgtggcca ccctgattca    4020
tttaaagatt tagaatttgt agtatggcgt gttcaatata tcgtcaacga tcaaattgga    4080
ggagacaagt ttaatacaac gttagcgaca attgtaaatc aatgcctaac cccttatatc    4140
aaacccaaaa gtgaaaaaac tattccagtt tatgtcttag aattggccgc ggtcgtatcc    4200
catttaggtt caaaagttaa aagttggagg cttttaattg cggaattgtt ccaaaatgac    4260
aaaaaacttt cggtaattgg cagcgatcaa acttgggaaa agattattta cgaatggtcc    4320
atttatccag aaaataagtc aaaaatcttg aacgatttac tattagaaat tggctccaag    4380
cgttcaagtg tgactccgac tttaatcacg tttaacttag gaagcgattc tgaagtcgag    4440
tacaagtgcc aaaaccttt gaaaatatcg tacttgttga tggtatcgcc aaatgacgca    4500
tatttgttgc acttttcctc tttaataagt tgcattttcc actatttggt gtccaaagat    4560
atcaagctca agggaagctg ctggatctta ctaagggttt tactttaag attttcagag    4620 tcccatttca atgactattg gtctatgatc agttactgtt tacaaactaa tttgcaagaa    4680
ttttatgaat cacttcaaat acagtcagaa gtcgatccac aaacaatatt gcaagtatgt    4740
aaaactttgg atttgctact cttactcaac atggaaggct tcacctctac gaatgagtgg    4800
atctttgtta ttgatacaat aaattgcgta tataaaacga actcattcgt cgcgctggta    4860
gatgaaatcg cagaattcaa agattacgaa ataaccaaaa ctgatgatct tgaattaccg    4920
acaactttaa aagatggtct cccattatta cgaggcattc acaaaatcga gagacacacg    4980
caactaagaa gcttcttcca gaatttgagt tatctacatt atgagaaagt ttacggacta    5040
gggtcagttg atttatatgg ttgtggtgaa gatctcaaaa aagatattct gtcatga       5097
```

<210> SEQ ID NO 12

```
<211> LENGTH: 1698
<212> TYPE: PRT
<213> ORGANISM: Saccharomyces cerevisiae

<400> SEQUENCE: 12

Met Ser Leu Pro Leu Lys Pro Leu Thr Ile Asp Ser Asn Asn Lys Gln
 1               5                  10                  15

Leu Asp Ser Lys Gln Lys Phe Arg Ala Asn Val Glu Arg Ala Leu
             20                  25                  30

Glu Arg Phe Asp Ser Val Thr Glu Trp Ala Asp Tyr Ile Ala Ser Leu
         35                  40                  45

Gly Thr Leu Leu Lys Ala Leu Gln Ser Trp Ser Pro Lys Phe Gln Asn
     50                  55                  60

Val Arg Tyr Tyr Val Pro Ser Pro Tyr Gln Val Ser Arg Arg Leu Thr
 65                  70                  75                  80

Ser Ser Leu Ser Pro Ala Leu Pro Ala Gly Val His Gln Lys Thr Leu
                 85                  90                  95

Glu Val Tyr Thr Tyr Ile Phe Glu His Ile Gly Leu Glu Thr Leu Ala
            100                 105                 110

Thr Glu Cys Asn Ile Trp Ile Pro Gly Ile Leu Pro Leu Met Thr Tyr
        115                 120                 125

Ala Ser Met Ser Val Arg Ser His Leu Ile Glu Leu Tyr Asp Asn Tyr
    130                 135                 140

Ile Leu Leu Leu Pro Gln Thr Thr Leu Arg Leu Leu Ile Arg Pro Leu
145                 150                 155                 160

Ile Ser Ser Leu Leu Pro Gly Ile Asp Asp Glu Ser Asn Asp Phe Leu
                165                 170                 175

Pro Leu Thr Leu Lys Leu Ile Glu Thr Leu Gln Glu Asn Leu Asp Asp
            180                 185                 190

Asp Ser Leu Phe Trp Gln Thr Leu Phe Leu Val Met Thr Ala Asn Lys
        195                 200                 205

Gly Arg Arg Leu Gly Gly Leu Thr Trp Leu Thr Arg Lys Phe Pro Ser
    210                 215                 220

Leu Asn Ala Val Pro His Leu Val Asn Lys Ile Lys Met Glu Ala Glu
225                 230                 235                 240

Glu Asn Pro Ser Glu Thr Glu Thr Asn Asp Ser His Leu Asp Arg Lys
                245                 250                 255

Lys Arg Lys Glu Glu Ala Phe Lys Val Leu Leu Pro Ala Ala Lys Asp
            260                 265                 270

Leu Val Thr Pro Glu Pro Gly Leu Leu Ile Arg Cys Leu Val Gly Cys
        275                 280                 285

Leu Glu Asp Glu Asn Asp Ile Leu Ile Lys Arg Ser Val Leu Asp Leu
    290                 295                 300

Leu Leu Gln Arg Leu Arg Leu Asp Ser Pro Val Leu Asn Val Leu Ile
305                 310                 315                 320

Thr Ser Glu Asp Lys Lys Leu Leu Ile Met Ser Cys Cys Arg Thr Thr
                325                 330                 335

Leu Ser Lys Asp Met Ser Leu Asn Arg Arg Ile Trp Asn Trp Leu Leu
            340                 345                 350

Gly Pro Thr Ala Gly Gly Met Leu Asn Asn Asn Gly Gly Asn Ser Met
        355                 360                 365

Glu Tyr Thr Thr Ser Val Lys Ser Ala Asn Glu Glu Ser Asn Val Tyr
    370                 375                 380

Phe Thr Lys Tyr Gly Leu Ser Ala Leu Leu Glu Gly Leu Ser Asp Leu
```

```
                385                 390                 395                 400
Leu Ser Glu Glu Ser Val Leu Thr Ala Phe Arg Ile Ser Met Ala
                405                 410                 415
Val Met Asp Arg Trp Glu Ile Gly Ser Leu Val Ile Pro Glu Leu Phe
                420                 425                 430
Ile Pro Leu Leu Tyr Ser Ser Glu Lys Phe Lys Gln Asn Glu Gln Ile
                435                 440                 445
Met Lys Thr Ala Arg Thr Phe Phe Asp Asn Thr Glu Thr Asn Ile Ile
                450                 455                 460
Trp Gly Lys Leu Phe Gln Glu Leu Glu Asp Ile Lys Asn Leu Lys Ile
465                 470                 475                 480
Leu Asp Phe Val Leu Thr Asn Phe Asn Ile Gly Asn Asp Glu Ile
                485                 490                 495
Ile Val Arg His Leu Pro Leu Ile Leu Leu Thr Leu Leu Ala Leu Pro
                500                 505                 510
Ser Asn Asp Lys Asp Phe Asp Asn Ile Tyr Lys Leu Gln Lys Phe Ser
                515                 520                 525
Leu Tyr Asn Lys Leu Leu Asn Tyr Ile Pro Glu Arg Ala Leu Leu Pro
                530                 535                 540
Leu Ser His Ser Lys Leu Lys His Asp Asp Glu Val Ser Cys Glu Glu
545                 550                 555                 560
Leu Leu Ala Lys Ile Arg Gly Phe Tyr Thr Asn Val Ser Asn Pro Ser
                565                 570                 575
Ser Ile Leu Glu Lys Glu Asn Ile Ala Glu Arg Leu Pro Pro Phe Thr
                580                 585                 590
Thr Glu Asp Leu Thr Phe Leu Ile Ala Asp Leu Ile Gln Lys Lys Leu
                595                 600                 605
Leu Ser Ser Leu Trp Asp Leu Glu Asn Ile Asn Glu Ser Ser Lys Leu
                610                 615                 620
Phe Ile Ala Ile Phe Glu Lys Ile Pro Glu Ser Glu Leu Lys Gly
625                 630                 635                 640
Arg Ser His Ile Ser Trp Ser Asp Lys Lys Ile Thr Gln Ser Ile Phe
                645                 650                 655
Glu Ala Ile Pro Arg Leu Cys Glu Ser Asn Asn Asp Ala Lys Ser Glu
                660                 665                 670
Glu Ile Val Gly Ile Val Glu Ile Phe Gly Asn Tyr Leu Tyr Ser Arg
                675                 680                 685
Met Glu Phe Ile Glu Ser Met Lys Leu Leu Lys Val Val Met Met Ala
                690                 695                 700
Val Trp Lys Ser Leu Lys Asp Pro Arg His Gln Ile Leu Gly Val Lys
705                 710                 715                 720
Asn Leu Lys Thr Leu Asn Arg Phe Ile Pro Ser Lys Phe Ile Glu Ser
                725                 730                 735
Ala Leu Val Tyr Thr Phe Val Glu Glu Asp Ile Ser Glu Arg Leu
                740                 745                 750
Ser Val Leu Asp Leu Leu Trp Thr Gln Leu Asp Ser Asp Ser Asn Leu
                755                 760                 765
Ile Arg Arg Pro Leu Glu Leu Ile Leu Gly Glu Leu Phe Asp Asp Gln
                770                 775                 780
Asn Pro Phe Tyr Leu Thr Val Ser Lys Trp Ile Leu Ser Ile Leu Asn
785                 790                 795                 800
Ser Gly Ser Ala Ser Arg Leu Phe Tyr Ile Leu Thr Asp Asn Ile Leu
                805                 810                 815
```

-continued

```
Lys Val Asn Arg Leu Glu Lys Glu Arg Leu Asp Glu Arg Asp Asp Leu
        820                 825                 830

Asp Met Leu Thr Tyr Glu Phe Gln Met Leu Ala Tyr Val Leu Lys Thr
        835                 840                 845

Asn Asn Gly Arg Thr Arg Lys Val Phe Ser Thr Glu Leu Thr Ser Ile
        850                 855                 860

Lys Ser Ser Thr Ile Trp Lys Asn Glu Asp Val Ser Thr Tyr Lys Ser
865                 870                 875                 880

Leu Leu Leu Val Thr Leu Met Arg Phe Leu Asn Ile Lys Ser Asn Thr
                885                 890                 895

His Ala Lys Ser Ile Arg Ser Ala Leu Ile Leu Leu Asp Ile Leu Leu
        900                 905                 910

Asp Gly Thr Glu Gln Asn Phe Lys Asp Ile Val Ile Phe Leu Leu Gln
        915                 920                 925

Met Ser Ser Lys Tyr Ile Ala Glu Glu Gly Ile Glu Pro Glu Leu Ile
        930                 935                 940

Ala Val Ser Leu Leu Asp Ile Val Ser Lys Val Leu Arg Leu Ser His
945                 950                 955                 960

Asp Asn Gly Ile Lys Leu Asp Ile Phe Asp Asp Asn Ala Ala His Leu
                965                 970                 975

Lys Tyr Ile Asp Phe Leu Val Thr Ser Val Ser Asn Met Lys Ser Pro
                980                 985                 990

Leu Ile Val Thr Ala Tyr Val Lys Leu Leu Ser Glu Ser Ile Val Tyr
                995                 1000                1005

Phe Glu Asn Ser Ile Phe Arg Met Ile Leu Pro Leu Ser Ala Ser Leu
        1010                1015                1020

Val Gln Cys Val Gln Arg Leu Phe Leu Leu Glu Lys Arg Glu Gly Gly
1025                1030                1035                1040

Tyr Tyr Gln Pro Ile Ala Leu Leu Leu Gly Gly Leu Glu Glu Leu Leu
                1045                1050                1055

Glu Ile Ser His Gly Tyr Leu Val Thr Glu Glu Arg Glu Gly Tyr Phe
                1060                1065                1070

Ser Gly Ser Asn Leu Lys Gly Asp Phe Ile Gln Ser Val Val Ser Asn
        1075                1080                1085

Val Phe Ser Ser Asp Ser Ser Asn Glu Glu Ser Lys Ile Gln Gly Glu
        1090                1095                1100

Arg Asp Val Ile Leu Gln Ser Phe Arg Gln Val Ile Ser Cys Cys Leu
1105                1110                1115                1120

Asp Ile Trp Tyr Trp Ala His Asn Ile Ser Cys Lys Ser Asn Asp Asp
                1125                1130                1135

Ser Ser Leu Asp Ala Thr Asn His Asn Ser Tyr Lys Phe Lys Phe Arg
                1140                1145                1150

Ser Lys Lys Leu Leu Glu Thr Leu Phe Leu Leu Glu Pro Leu Glu Leu
        1155                1160                1165

Leu Glu Asn Leu Ile Ser Ile Arg Ser Asp Asn Thr Thr Val Thr Leu
        1170                1175                1180

Val His Val Leu Asp Gly Asn Lys Pro Ala Ile Thr Ile Pro His Leu
1185                1190                1195                1200

Leu Tyr Gly Val Ile Ile Arg Tyr Asn Arg Thr Ala Ser Val Lys Phe
                1205                1210                1215

Ser Asn Arg Asp Gly Ser Arg Ser Thr Thr Lys Leu Thr Lys Gly
                1220                1225                1230
```

-continued

```
Glu Pro Ser Met Leu Lys Arg Leu Ser Gly Glu Ser Ile Ile Ala Phe
        1235                1240                1245

Leu Phe Asn Tyr Val Asp Ser Val Glu Asn Ser Ala Met Glu Glu Phe
        1250                1255                1260

Tyr Gly Asp Phe Leu Leu Phe Phe Arg Glu Val Ala Thr Asn Tyr Asn
1265                1270                1275                1280

Leu Tyr Ser Asp Val Ser Leu Ser Ile Leu Lys Leu Val Ala Leu Ile
            1285                1290                1295

Ser Gly Lys Val Ser Lys Thr Gln Phe Gly Glu Gln Lys Arg Val Arg
            1300                1305                1310

Arg Glu Ile Ser Asp Val Phe Phe Lys Tyr Leu Pro Asn Ala Phe Ile
        1315                1320                1325

Asn Phe Thr Asn Leu Tyr Arg Gly His Pro Asp Ser Phe Lys Asp Leu
        1330                1335                1340

Glu Phe Val Val Trp Arg Val Gln Tyr Ile Val Asn Asp Gln Ile Gly
1345                1350                1355                1360

Gly Asp Lys Phe Asn Thr Thr Leu Ala Thr Ile Val Asn Gln Cys Leu
            1365                1370                1375

Thr Pro Tyr Ile Lys Pro Lys Ser Glu Lys Thr Ile Pro Gly Tyr Val
            1380                1385                1390

Leu Glu Leu Ala Ala Val Val Ser His Leu Gly Ser Lys Val Lys Ser
        1395                1400                1405

Trp Arg Leu Leu Ile Ala Glu Leu Phe Gln Asn Asp Lys Lys Leu Ser
        1410                1415                1420

Val Ile Gly Ser Asp Gln Thr Trp Glu Lys Ile Ile Tyr Glu Trp Ser
1425                1430                1435                1440

Ile Tyr Pro Glu Asn Lys Ser Lys Ile Leu Asn Asp Leu Leu Leu Glu
            1445                1450                1455

Ile Gly Ser Lys Arg Ser Ser Val Thr Pro Thr Leu Ile Thr Phe Asn
            1460                1465                1470

Leu Gly Ser Asp Ser Glu Val Glu Tyr Lys Cys Gln Asn Leu Leu Lys
        1475                1480                1485

Ile Ser Tyr Leu Leu Met Val Ser Pro Asn Asp Ala Tyr Leu Leu His
        1490                1495                1500

Phe Ser Ser Leu Ile Ser Cys Ile Phe His Tyr Leu Val Ser Lys Asp
1505                1510                1515                1520

Ile Lys Leu Lys Gly Ser Cys Trp Ile Leu Leu Arg Val Leu Leu Leu
            1525                1530                1535

Arg Phe Ser Glu Ser His Phe Asn Asp Tyr Trp Ser Met Ile Ser Tyr
        1540                1545                1550

Cys Leu Gln Thr Asn Leu Gln Glu Phe Tyr Glu Ser Leu Gln Ile Gln
        1555                1560                1565

Ser Glu Val Asp Pro Gln Thr Ile Leu Gln Val Cys Lys Thr Leu Asp
        1570                1575                1580

Leu Leu Leu Leu Leu Asn Met Glu Gly Phe Thr Ser Thr Asn Glu Trp
1585                1590                1595                1600

Ile Phe Val Ile Asp Thr Ile Asn Cys Val Tyr Lys Thr Asn Ser Phe
            1605                1610                1615

Val Ala Leu Val Asp Glu Ile Ala Glu Phe Lys Asp Tyr Glu Ile Thr
            1620                1625                1630

Lys Thr Asp Asp Leu Glu Leu Pro Thr Thr Leu Lys Asp Gly Leu Pro
        1635                1640                1645

Leu Leu Arg Gly Ile His Lys Ile Glu Arg His Thr Gln Leu Arg Ser
```

Phe Phe Gln Asn Leu Ser Tyr Leu His Tyr Glu Lys Val Tyr Gly Leu
1665                1670                1675                1680

Gly Ser Val Asp Leu Tyr Gly Cys Gly Glu Asp Leu Lys Lys Asp Ile
                1685                1690                1695

Leu Ser

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 13
acacgacaga ccataatgga tgtccacgag gtctctgaga tttactaacc ctctgccgta    60
cgctgcaggt cgac                                                     74

<210> SEQ ID NO 14
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 14
cgaatcccaa gatgcttacg gtgtcggtct cgtaggaggg ttctccactt cactgatcga    60
tgaattcgag ctcg                                                     74

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 15
tagccttctg caaaagttct taagaaaaca cgacagacca taatg                   45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 16
aataaaacaa tcgtcctctt ggttctccga atcccaagat gctta                   45

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 17
tcagtcacct gttcataagc aaata                                         25

<210> SEQ ID NO 18
<211> LENGTH: 25
<212> TYPE: DNA
<213> ORGANISM: Artificial Sequence

```
<220> FEATURE:
<223> OTHER INFORMATION: Description of Artificial Sequence: primer

<400> SEQUENCE: 18
tatagccttg atatcatctt ccagc                                         25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 19
gtttcagact gatgtcgtta aacct                                         25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 20
atgaaataaa ctggagtacg gatca                                         25

<210> SEQ ID NO 21
<211> LENGTH: 1827
<212> TYPE: DNA
<213> ORGANISM: Saccharomyces cerevisiae

<400> SEQUENCE: 21
atgagtgata aaacagtcg tatcgctatc gttagcgctg ataaatgtaa accaaaaaag      60
tgtcgtcaag agtgtaaacg ttcgtgtccc gttgtgaaaa ctggtaaatt atgtattgaa    120
gtcactccaa cttcaaaaat cgcattcatt tccgaaatct tgtgtattgg ttgtggtatt    180
tgcgttaaga aatgtccatt tgatgctatt caaattatca atttgccaac taatttagaa    240
gcccatgtaa ctcaccgtta ctctgccaat agtttcaaac tgcacagatt gccaacacca    300
agaccgggtc aagtccttgg tttagtcggt accaacggta ttggtaagtc taccgccttg    360
aaaatcttag ccggtaaaca aaaacctaat ttaggtcgtt ttgatgatcc tcctgaatgg    420
caggaaatta ttaaatattt ccgtggttct gaattacaaa attacttcac caagatgctg    480
gaagatgata tcaaggctat aatcaaacct caatatgttg ataacattcc tcgtgctatt    540
aaaggtccgg ttcaaaaagt tggcgaactt ttgaaattga aatggaaaa aagtcctgaa    600 gatgtgaaac gctacatcaa aattttacag ttggaaaacg ttttgaaaag agatattgaa    660
aagttatctg gtggtgaact gcaaagattt gccattggta tgtcatgtgt tcaagaggct    720
gatgtttata tgttcgatga accttcatct tatttggatg ttaagcaacg tttgaatgcc    780
gctcaaatta ttagatcttt actagctcca actaaatacg ttatttgtgt tgagcacgat    840
ttgtcagttt tggattatct ttccgatttc gtttgtatca tatatggtgt tccatctgtt    900
tacggtgttg ttacattacc agcctctgtc agagaaggta tcaacatatt cttggacggt    960
catattcctg ctgaaaacct gagattcaga actgaagctt tacaatttag aatagctgat   1020
gctaccgaag acttgcagaa tgactctgct agtcgcgcct tctcttaccc aagtttgaag   1080
aaaactcaag gtgattttgt tttgaatgtt gaagaaggta aattctccga ttccgaaatc   1140
cttgttatga tgggtgaaaa cggtaccggt aagaccactt tgatcaaatt actagctggt   1200
```

-continued

```
gctttgaagc cagatgaagg acaagatatt ccaaaattga atgtttctat gaaaccacaa    1260
aaaattgcac caaagttccc aggtactgtc agacaattgt ttttcaagaa aattagagga    1320
caattcctaa atccacagtt tcagactgat gtcgttaaac ctttaaggat tgacgatatt    1380
attgatcaag aagtccaaca tttgtctggt ggtgaattac aaagagtcgc catcgtcttg    1440
gcattgggta tcccagcaga catatacttg attgatgagc catctgccta cttagattcc    1500
gaacaacgta ttatctgttc taaagttatc agaagattca tcttacataa taagaaaact    1560
gcgtttattg tcgagcacga tttcatcatg gctacttatc ttgctgataa ggtcattgtt    1620
tttgaaggta ttccttccaa gaatgctcac gcaagagccc ctgaatcttt gttgactggt    1680
tgtaacagat ttttgaagaa tttgaatgtc accttcagaa gggatccaaa ctccttcaga    1740
ccaagaatta ataagctaga ttcccaaatg gataaagaac aaaaatcatc aggaaactac    1800
tttttcttgg ataacaccgg tatttaa                                       1827
```

<210> SEQ ID NO 22
<211> LENGTH: 608
<212> TYPE: PRT
<213> ORGANISM: Saccharomyces cerevisiae

<400> SEQUENCE: 22

```
Met Ser Asp Lys Asn Ser Arg Ile Ala Ile Val Ser Ala Asp Lys Cys
 1               5                  10                  15

Lys Pro Lys Lys Cys Arg Gln Glu Cys Lys Arg Ser Cys Pro Val Val
            20                  25                  30

Lys Thr Gly Lys Leu Cys Ile Glu Val Thr Pro Thr Ser Lys Ile Ala
        35                  40                  45

Phe Ile Ser Glu Ile Leu Cys Ile Gly Cys Gly Ile Cys Val Lys Lys
    50                  55                  60

Cys Pro Phe Asp Ala Ile Gln Ile Ile Asn Leu Pro Thr Asn Leu Glu
65                  70                  75                  80

Ala His Val Thr His Arg Tyr Ser Ala Asn Ser Phe Lys Leu His Arg
                85                  90                  95

Leu Pro Thr Pro Arg Pro Gly Gln Val Leu Gly Leu Val Gly Thr Asn
            100                 105                 110

Gly Ile Gly Lys Ser Thr Ala Leu Lys Ile Leu Ala Gly Lys Gln Lys
        115                 120                 125

Pro Asn Leu Gly Arg Phe Asp Asp Pro Pro Glu Trp Gln Glu Ile Ile
    130                 135                 140

Lys Tyr Phe Arg Gly Ser Glu Leu Gln Asn Tyr Phe Thr Lys Met Leu
145                 150                 155                 160

Glu Asp Asp Ile Lys Ala Ile Ile Lys Pro Gln Tyr Val Asp Asn Ile
                165                 170                 175

Pro Arg Ala Ile Lys Gly Pro Val Gln Lys Val Gly Glu Leu Leu Lys
            180                 185                 190

Leu Arg Met Glu Lys Ser Pro Glu Asp Val Lys Arg Tyr Ile Lys Ile
        195                 200                 205

Leu Gln Leu Glu Asn Val Leu Lys Arg Asp Ile Glu Lys Leu Ser Gly
    210                 215                 220

Gly Glu Leu Gln Arg Phe Ala Ile Gly Met Ser Cys Val Gln Glu Ala
225                 230                 235                 240

Asp Val Tyr Met Phe Asp Glu Pro Ser Ser Tyr Leu Asp Val Lys Gln
                245                 250                 255

Arg Leu Asn Ala Ala Gln Ile Ile Arg Ser Leu Leu Ala Pro Thr Lys
```

```
                260                 265                 270
Tyr Val Ile Cys Val Glu His Asp Leu Ser Val Leu Asp Tyr Leu Ser
            275                 280                 285

Asp Phe Val Cys Ile Ile Tyr Gly Val Pro Ser Val Tyr Gly Val Val
        290                 295                 300

Thr Leu Pro Ala Ser Val Arg Glu Gly Ile Asn Ile Phe Leu Asp Gly
305                 310                 315                 320

His Ile Pro Ala Glu Asn Leu Arg Phe Arg Thr Glu Ala Leu Gln Phe
                325                 330                 335

Arg Ile Ala Asp Ala Thr Glu Asp Leu Gln Asn Asp Ser Ala Ser Arg
            340                 345                 350

Ala Phe Ser Tyr Pro Ser Leu Lys Lys Thr Gln Gly Asp Phe Val Leu
        355                 360                 365

Asn Val Glu Glu Gly Glu Phe Ser Asp Ser Glu Ile Leu Val Met Met
    370                 375                 380

Gly Glu Asn Gly Thr Gly Lys Thr Thr Leu Ile Lys Leu Leu Ala Gly
385                 390                 395                 400

Ala Leu Lys Pro Asp Glu Gly Gln Asp Ile Pro Lys Leu Asn Val Ser
                405                 410                 415

Met Lys Pro Gln Lys Ile Ala Pro Lys Phe Pro Gly Thr Val Arg Gln
            420                 425                 430

Leu Phe Phe Lys Lys Ile Arg Gly Gln Phe Leu Asn Pro Gln Phe Gln
        435                 440                 445

Thr Asp Val Val Lys Pro Leu Arg Ile Asp Asp Ile Asp Gln Glu
    450                 455                 460

Val Gln His Leu Ser Gly Gly Glu Leu Gln Arg Val Ala Ile Val Leu
465                 470                 475                 480

Ala Leu Gly Ile Pro Ala Asp Ile Tyr Leu Ile Asp Glu Pro Ser Ala
                485                 490                 495

Tyr Leu Asp Ser Glu Gln Arg Ile Ile Cys Ser Lys Val Ile Arg Arg
            500                 505                 510

Phe Ile Leu His Asn Lys Lys Thr Ala Phe Ile Val Glu His Asp Phe
        515                 520                 525

Ile Met Ala Thr Tyr Leu Ala Asp Lys Val Ile Val Phe Glu Gly Ile
    530                 535                 540

Pro Ser Lys Asn Ala His Ala Arg Ala Pro Glu Ser Leu Leu Thr Gly
545                 550                 555                 560

Cys Asn Arg Phe Leu Lys Asn Leu Asn Val Thr Phe Arg Arg Asp Pro
                565                 570                 575

Asn Ser Phe Arg Pro Arg Ile Asn Lys Leu Asp Ser Gln Met Asp Lys
            580                 585                 590

Glu Gln Lys Ser Ser Gly Asn Tyr Phe Phe Leu Asp Asn Thr Gly Ile
        595                 600                 605

<210> SEQ ID NO 23
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 23
attatccact atctcatgga tgtccacgag gtctctggag actcttgcac attatgcgta      60
cgctgcaggt cgac                                                       74
```

```
<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 24
caaattaccc actattcacg gtgtcggtct cgtagcagga cgctgcatgt ttatgatcga      60
tgaattcgag ctcg                                                        74

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 25
aagaggaaaa gtagaagcca agagtcaatt atccactatc tcatg                      45

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 26
atttaattat caaaaattca tgaaagacaa attacccact attca                      45

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 27
atttcacctg caagttcata aaaag                                            25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 28
catataatac tctgtcatcc tgggg                                            25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 29
tcggttatgt agaagaatgt gtcaa                                            25

<210> SEQ ID NO 30
<211> LENGTH: 25
<212> TYPE: DNA
<213> ORGANISM: Artificial Sequence
```

```
<220> FEATURE:
<223> OTHER INFORMATION: Description of Artificial Sequence: primer

<400> SEQUENCE: 30
aattcattgg tgcaggtagt tagag                                              25

<210> SEQ ID NO 31
<211> LENGTH: 1227
<212> TYPE: DNA
<213> ORGANISM: Saccharomyces cerevisiae

<400> SEQUENCE: 31
atgtccaaaa tagaagagct accaccatca gatactgatg accattcgta ttctagtaaa      60
ccgggagatg tatttttagc atttgtggac gcacctgtta agagactga tgacatatta     120
gttgaagata gctttattgg cggtgaacct aagtggctac atccggattc cgaaccacct     180
gctgaactat tgaaatgtgg tgcttgtaaa tcagcggata atatgaagct gttactacaa     240
gcttttttcgc ccttagatga tgagcagatg agtgccatac aacaacgtct tggtatcaat     300
aatatgagct atattaatcc ccaggatgac agagtattat atgtcttcct gtgtaccgaa     360
tgtcaaagga agggcaattc tgttcgctgt atcagaggag taagaagaa taaaaacgtt      420
gatagccttt ccgaaaaaat ggcttcaact tcattggaaa aagacttcca aatcaatccc     480
tttgacttgt cgaataattc agattctaaa tgtaatgctt tttcaagcaa cccatttggc     540
ggtgcaaatg ctaacccttt tggagctgat agcattaatt ccaatatatc acaaagcaag     600
gacgaaggca aaagaagga atctgctacc gtttctgcaa agacggcgag aaaactacat      660
gatttacaaa aggacaaaga atacgatggc aataaatgct ttaaaagttg tttgttgtac     720
gttgaagagg aaaccttcaa aaataaaag ccagctcatc tgcagctgcc aaaaaattta     780
aaaattgata aggaggcact agatttaaca ggagatgagg atctcgaaaa agatccgatc     840
aaattggacc cgaggacaga aaaattatcc aagtttcttg atgacgacac attccaaaaa     900
ttccaagaag tggttggtta aacccgctt caagtattac gttatgactt aggcggaaaa      960
cctttgctat atgccgaaac aaaagtcgat attttaagca ctgtgccaag accgggctac    1020
aacccatcga gccaaagaat ctttgaaatg cagttaatgc caaagatgat ttttgatctg    1080
gaagaagtag tgtctgtcga taacggtatg gaatggggta ccattcttgt tttcactgat    1140
gttgaaaatt acatgcctga atttgatgaa catggtgtcg gttatgtaga agaatgtgtc    1200
aaagttcagt gggaatcgag aacgtga                                        1227

<210> SEQ ID NO 32
<211> LENGTH: 408
<212> TYPE: PRT
<213> ORGANISM: Saccharomyces cerevisiae

<400> SEQUENCE: 32

Met Ser Lys Ile Glu Glu Leu Pro Pro Ser Asp Thr Asp Asp His Ser
 1               5                  10                  15

Tyr Ser Ser Lys Pro Gly Asp Val Phe Leu Ala Phe Val Asp Ala Pro
                20                  25                  30

Val Lys Glu Thr Asp Asp Ile Leu Val Glu Asp Ser Phe Ile Gly Gly
            35                  40                  45

Glu Pro Lys Trp Leu His Pro Asp Ser Glu Pro Pro Ala Glu Leu Leu
        50                  55                  60

Lys Cys Gly Ala Cys Lys Ser Ala Asp Asn Met Lys Leu Leu Leu Gln
65                  70                  75                  80
```

-continued

```
Ala Phe Ser Pro Leu Asp Asp Glu Gln Met Ser Ala Ile Gln Gln Arg
                 85                  90                  95

Leu Gly Ile Asn Asn Met Ser Tyr Ile Asn Pro Gln Asp Asp Arg Val
            100                 105                 110

Leu Tyr Val Phe Leu Cys Thr Glu Cys Gln Arg Lys Gly Asn Ser Val
        115                 120                 125

Arg Cys Ile Arg Gly Val Lys Lys Asn Lys Asn Val Asp Ser Leu Ser
    130                 135                 140

Glu Lys Met Ala Ser Thr Ser Leu Glu Lys Asp Phe Gln Ile Asn Pro
145                 150                 155                 160

Phe Asp Leu Ser Asn Asn Ser Asp Ser Lys Cys Asn Ala Phe Ser Ser
                165                 170                 175

Asn Pro Phe Gly Gly Ala Asn Ala Asn Pro Phe Gly Ala Asp Ser Ile
            180                 185                 190

Asn Ser Asn Ile Ser Gln Ser Lys Asp Glu Gly Lys Lys Lys Glu Ser
        195                 200                 205

Ala Thr Val Ser Ala Lys Thr Ala Arg Lys Leu His Asp Leu Gln Lys
    210                 215                 220

Asp Lys Glu Tyr Asp Gly Asn Lys Cys Phe Lys Ser Cys Leu Leu Tyr
225                 230                 235                 240

Val Glu Glu Glu Thr Phe Lys Asn Lys Pro Ala His Leu Gln Leu
                245                 250                 255

Pro Lys Asn Leu Lys Ile Asp Lys Glu Ala Leu Asp Leu Thr Gly Asp
            260                 265                 270

Glu Asp Leu Glu Lys Asp Pro Ile Lys Leu Asp Pro Arg Thr Glu Lys
        275                 280                 285

Leu Ser Lys Phe Leu Asp Asp Asp Thr Phe Gln Lys Phe Gln Glu Val
    290                 295                 300

Val Gly Tyr Asn Pro Leu Gln Val Leu Arg Tyr Asp Leu Gly Gly Lys
305                 310                 315                 320

Pro Leu Leu Tyr Ala Glu Thr Lys Val Asp Ile Leu Ser Thr Val Pro
                325                 330                 335

Arg Pro Gly Tyr Asn Pro Ser Ser Gln Arg Ile Phe Glu Met Gln Leu
            340                 345                 350

Met Pro Lys Met Ile Phe Asp Leu Glu Glu Val Val Ser Val Asp Asn
        355                 360                 365

Gly Met Glu Trp Gly Thr Ile Leu Val Phe Thr Asp Val Glu Asn Tyr
    370                 375                 380

Met Pro Glu Phe Asp Glu His Gly Val Gly Tyr Val Glu Glu Cys Val
385                 390                 395                 400

Lys Val Gln Trp Glu Ser Arg Thr
                405

<210> SEQ ID NO 33
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 33
ccacaagaca gaaatatgga tgtccacgag gtctctcatg gatagtgacc tagttgcgta      60
cgctgcaggt cgac                                                       74
```

```
<210> SEQ ID NO 34
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 34
tgctttggtg atcgtttacg gtgtcggtct cgtagtgcca gtctgcatgt cgttgatcga      60
tgaattcgag ctcg                                                        74

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 35
aacatcaccc cccttcttac gaaactgcca caagacagaa atatg                      45

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 36
tgtgtattta tttatgtagg ttgctaatgc tttggtgatc gttta                      45

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 37
ccaaatatgt ctgcaacgtg tacta                                            25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 38
ggtacacctt ataccccttg tttct                                            25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 39
aaccatagaa acaagggta taagg                                             25

<210> SEQ ID NO 40
<211> LENGTH: 25
<212> TYPE: DNA
<213> ORGANISM: Artificial Sequence
<220> FEATURE:
```

-continued

<223> OTHER INFORMATION: Description of Artificial Sequence: primer

<400> SEQUENCE: 40
tgatgcgaaa ttcaacatct tagta                                          25

<210> SEQ ID NO 41
<211> LENGTH: 342
<212> TYPE: DNA
<213> ORGANISM: Saccharomyces cerevisiae

<400> SEQUENCE: 41
atgacagagg ttgtgggatt ctgggagagc gtgtcagatg acgaatcaga agacaaagac    60
tgtatggagg tgcagaacac agtgagtgcc gacgagagcc cacttgtgca gagccttgta   120
tcctttgtag gctcgtgctc catcaaccta cttttgccct tcctcaacgg catgatgctc   180
ggcttcggcg agctatttgc tcacgagctc tgctggagat tcaattggtt taaccataga   240 aacaagggt ataaggtgta cccagagtcg cgcaaaatag cagcattgaa agagatttca    300
agccctggca cccgtgggag ggttgcgtcc aagttccttt aa                      342

<210> SEQ ID NO 42
<211> LENGTH: 113
<212> TYPE: PRT
<213> ORGANISM: Saccharomyces cerevisiae

<400> SEQUENCE: 42

Met Thr Glu Val Val Gly Phe Trp Glu Ser Val Ser Asp Asp Glu Ser
  1               5                  10                  15

Glu Asp Lys Asp Cys Met Glu Val Gln Asn Thr Val Ser Ala Asp Glu
             20                  25                  30

Ser Pro Leu Val Gln Ser Leu Val Ser Phe Val Gly Ser Cys Ser Ile
         35                  40                  45

Asn Leu Leu Pro Phe Leu Asn Gly Met Met Leu Gly Phe Gly Glu
     50                  55                  60

Leu Phe Ala His Glu Leu Cys Trp Arg Phe Asn Trp Phe Asn His Arg
 65                  70                  75                  80

Asn Lys Gly Tyr Lys Val Tyr Pro Glu Ser Arg Lys Ile Ala Ala Leu
                 85                  90                  95

Lys Glu Ile Ser Ser Pro Gly Thr Arg Gly Arg Val Ala Ser Lys Phe
            100                 105                 110

Leu

<210> SEQ ID NO 43
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 43
agctatatcc ctagcatgga tgtccacgag gtctctctct atattggatg gagcgtcgta    60
cgctgcaggt cgac                                                     74

<210> SEQ ID NO 44
<211> LENGTH: 74
<212> TYPE: DNA
<213> ORGANISM: Artificial Sequence
<220> FEATURE:
<223> OTHER INFORMATION: Description of Artificial Sequence: primer

```
<400> SEQUENCE: 44
tgcaatagtg aaagattacg gtgtcggtct cgtagtacct gctgctagat ggcgtatcga      60
tgaattcgag ctcg                                                        74

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 45
atcaaataaa agggcgtggt acataaaagc tatatcccta gcatg                      45

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 46
ttacatctat atgtgtataa ttaattatgc aatagtgaaa gatta                      45

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 47
gattaacctt tacagaaccg ctaca                                            25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 48
gtaacatttg gtgaattttt caagg                                            25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 49
ggactatgct gaatggaaga tagaa                                            25

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 50
gatttcttca atggtgagag accta                                            25
```

<210> SEQ ID NO 51
<211> LENGTH: 3282
<212> TYPE: DNA
<213> ORGANISM: Saccharomyces cerevisiae

<400> SEQUENCE: 51

| | | | | | |
|---|---|---|---|---|---|
| atgaccagtc | taatagattt | gggcagatat | gttgaaagaa | cgcatcatgg | agaagataca | 60 |
| gagccaagat | cgaaaagggt | aaaaatcgca | aacctgact | tgtcttcctt | ccaaccaggc | 120 |
| agcattatta | agatccgttt | acaggatttt | gttacttaca | ctttaaccga | attcaatctt | 180 |
| tcaccgtctt | taaatatgat | cattgggcca | acggatctg | gaaaatctac | tttcgtatgc | 240 |
| gcagtgtgtt | taggattggc | tggtaaaccc | gagtatattg | gtaggagtaa | aaaagtggaa | 300 |
| gatttcatca | aaaatggtca | agatgtttca | aaaattgaaa | tcaccttgaa | aaattcacca | 360 |
| aatgttactg | atattgaata | catagacgca | cgtgatgaaa | caataaagat | taccaggatt | 420 |
| attacgagat | ccaagaggag | atcggattat | ctaataaatg | actaccaggt | atctgagagt | 480 |
| gtagttaaaa | ctttagttgc | tcagctgaac | attcagttgg | ataatctttg | tcaatttta | 540 |
| tctcaagagc | gtgttgagga | gtttgctcgc | ttgaagtcag | ttaaattatt | agtagagact | 600 |
| ataaggtcaa | tcgatgcaag | cttattggat | gtgttggatg | aactaaggga | attacaagga | 660 |
| aatgagcaaa | gcttgcaaaa | agatctcgat | tttaaaaaag | ctaaaattgt | tcatttgaga | 720 |
| caagaaagtg | ataaactacg | taaatcagtt | gaatctttac | gagattttca | aaataagaag | 780 |
| ggtgaaatcg | agttacactc | ccaactatta | ccttatgtga | agtaaagga | ccataaagaa | 840 |
| aagctaaaca | tatataaaga | agaatacgaa | cgagcgaaag | cgaacttaag | ggctatactg | 900 |
| aaggataaaa | aaccatttgc | aaatactaag | aagactttgg | aaaatcaggt | ggaagagtta | 960 |
| acagagaagt | gttccctaaa | aactgatgag | ttcctgaaag | caaagaaaa | gatcaacgaa | 1020 |
| atcttcgaaa | aattaaatac | tattagggat | gaggtcatca | aaaagaaaaa | ccagaacgaa | 1080 |
| tattatagag | gaagaaccaa | aaaactacag | gccaccatta | ttagtacaaa | ggaagatttt | 1140 |
| ctaaggagtc | aggaaatatt | agcacaaaca | catcttcctg | agaaaagcgt | atttgaagat | 1200 |
| atagacatta | aaagaaagga | aattattaat | aaagaaggcg | aaattaggga | tcttatttcc | 1260 |
| gaaattgatg | cgaaggcgaa | cgctattaat | catgagatga | aagcataca | gagacaagct | 1320 |
| gaaagcaaga | ccaaatccct | tacaacaact | gataaaatcg | gtatcttaaa | tcaggaccag | 1380 |
| gatttaaagg | aggtccgtga | tgctgtgttg | atggttagag | agcatccaga | aatgaaagat | 1440 |
| aaaattctag | aaccgccaat | aatgaccgtg | tctgccatta | acgctcaatt | tgctgcatat | 1500 |
| ttagcacaat | gtgtggatta | taatacgagt | aaagccttga | ctgttgttga | ttctgattct | 1560 |
| tacaagctat | ttgcaaatcc | aattcttgac | aaattcaagg | ttaatttgag | agaactctcc | 1620 |
| agtgcagaca | ccaccctcc | tgtaccagcg | gaaacggtga | gggacctggg | atttgagggt | 1680 |
| tatctatccg | atttattac | cggtgataag | agggttatga | aaatgctttg | tcaaactagc | 1740 |
| aaaattcata | ctataccggt | atcaagaagg | gaattgacgc | ctgctcagat | aaagaagttg | 1800 |
| attacaccaa | gaccgaatgg | gaaaattctt | tttaaaagga | ttattcatgg | aataggtta | 1860 |
| gtcgatatca | agcaatcagc | atatggtagt | aagcaggtct | ttcctactga | cgttagtatt | 1920 |
| aaacaaacta | attttatca | gggatcaatc | atgtcaaatg | agcagaaaat | tagaattgaa | 1980 |
| aatgaaatta | tcaacttaaa | gaatgaatac | aacgatcgaa | atctacgtt | agatgcattg | 2040 |
| tcaaaccaga | aaagtggtta | taggcacgaa | ttatctgagt | tggcgtcaaa | aaacgacgat | 2100 |
| attaataggg | aagctcatca | attaaatgag | attcgcaaga | agtacactat | gagaaaaagt | 2160 |

-continued

```
acaatagaga ctttaagaga gaaattagat caactgaaac gtgaagctag aaaggacgta    2220
tctcaaaaga ttaaagatat tgatgatcag atccaacaac tattactcaa gcaaagacat    2280
ttgctgtcta aaatggcctc ttcaatgaag agtttaaaga attgtcagaa ggagttaata    2340
agtactcaaa tccttcaatt tgaagcccaa aatatggatg tttctatgaa tgacgtaatt    2400
ggttttttca atgagaggga agctgatttg aagagccaat atgaagacaa gaaaaagttc    2460
gtaaaagaaa tgagagacac tcctgaattt caatcatgga tgagagaaat caggtcttat    2520
gaccaagaca ctaaggaaaa attgaataaa gtggcagaaa aatacgagga ggaagggaat    2580
ttcaatctgt cattcgttca ggatgttctc gataaattag aatcggagat agctatggta    2640
aaccacgacg agtcagccgt aacaattttg gatcaagtca cagccgaact gagagagttg    2700
gagcacacgg ttcctcagca gtcgaaagac ttggagacca ttaaagctaa attaaaagaa    2760
gatcacgcag ttttggagcc caaattagat gatattgtat caaaaatctc tgcaagattt    2820
gcgcgcttat tcaacaatgt tgggagtgct ggtgcggttc gtctagaaaa gccgaaggac    2880
tatgctgaat ggaagataga aatcatggta aaattcagag ataatgcacc tttaaaaaag    2940
ttagattccc acacgcaatc aggtggtgaa agagctgttt ctacagttct ttacatgatt    3000
gctttgcaag agtttacctc tgcaccattt agagtggttg atgaaatcaa tcaaggtatg    3060
gactctagaa atgaaaggat cgttcataaa gctatggtgg agaacgcgtg tgccgaaaac    3120
acttctcaat attttttaat cactccaaaa ttattgactg gcttgcatta tcatgaaaag    3180
atgagaatac actgtgtcat ggctggttct tggattccaa accctcctga ggatccgaag    3240
atgatacatt tcggtgaaac ttctaactac tcattcgatt aa                        3282
```

<210> SEQ ID NO 52
<211> LENGTH: 1093
<212> TYPE: PRT
<213> ORGANISM: Saccharomyces cerevisiae

<400> SEQUENCE: 52

```
Met Thr Ser Leu Ile Asp Leu Gly Arg Tyr Val Glu Arg Thr His His
  1               5                  10                  15

Gly Glu Asp Thr Glu Pro Arg Ser Lys Arg Val Lys Ile Ala Lys Pro
                 20                  25                  30

Asp Leu Ser Ser Phe Gln Pro Gly Ser Ile Ile Lys Ile Arg Leu Gln
             35                  40                  45

Asp Phe Val Thr Tyr Thr Leu Thr Glu Phe Asn Leu Ser Pro Ser Leu
         50                  55                  60

Asn Met Ile Ile Gly Pro Asn Gly Ser Gly Lys Ser Thr Phe Val Cys
 65                  70                  75                  80

Ala Val Cys Leu Gly Leu Ala Gly Lys Pro Glu Tyr Ile Gly Arg Ser
                 85                  90                  95

Lys Lys Val Glu Asp Phe Ile Lys Asn Gly Gln Asp Val Ser Lys Ile
                100                 105                 110

Glu Ile Thr Leu Lys Asn Ser Pro Asn Val Thr Asp Ile Glu Tyr Ile
            115                 120                 125

Asp Ala Arg Asp Glu Thr Ile Lys Ile Thr Arg Ile Ile Thr Arg Ser
        130                 135                 140

Lys Arg Arg Ser Asp Tyr Leu Ile Asn Asp Tyr Gln Val Ser Glu Ser
145                 150                 155                 160

Val Val Lys Thr Leu Val Ala Gln Leu Asn Ile Gln Leu Asp Asn Leu
                165                 170                 175
```

-continued

```
Cys Gln Phe Leu Ser Gln Glu Arg Val Glu Glu Phe Ala Arg Leu Lys
                180                 185                 190
Ser Val Lys Leu Leu Val Glu Thr Ile Arg Ser Ile Asp Ala Ser Leu
            195                 200                 205
Leu Asp Val Leu Asp Glu Leu Arg Glu Leu Gln Gly Asn Glu Gln Ser
        210                 215                 220
Leu Gln Lys Asp Leu Asp Phe Lys Lys Ala Lys Ile Val His Leu Arg
225                 230                 235                 240
Gln Glu Ser Asp Lys Leu Arg Lys Ser Val Glu Ser Leu Arg Asp Phe
                245                 250                 255
Gln Asn Lys Lys Gly Glu Ile Glu Leu His Ser Gln Leu Leu Pro Tyr
            260                 265                 270
Val Lys Val Lys Asp His Lys Glu Lys Leu Asn Ile Tyr Lys Glu Glu
        275                 280                 285
Tyr Glu Arg Ala Lys Ala Asn Leu Arg Ala Ile Leu Lys Asp Lys Lys
            290                 295                 300
Pro Phe Ala Asn Thr Lys Lys Thr Leu Glu Asn Gln Val Glu Glu Leu
305                 310                 315                 320
Thr Glu Lys Cys Ser Leu Lys Thr Asp Glu Phe Leu Lys Ala Lys Glu
                325                 330                 335
Lys Ile Asn Glu Ile Phe Glu Lys Leu Asn Thr Ile Arg Asp Glu Val
            340                 345                 350
Ile Lys Lys Lys Asn Gln Asn Glu Tyr Tyr Arg Gly Arg Thr Lys Lys
        355                 360                 365
Leu Gln Ala Thr Ile Ile Ser Thr Lys Glu Asp Phe Leu Arg Ser Gln
        370                 375                 380
Glu Ile Leu Ala Gln Thr His Leu Pro Glu Lys Ser Val Phe Glu Asp
385                 390                 395                 400
Ile Asp Ile Lys Arg Lys Glu Ile Ile Asn Lys Glu Gly Glu Ile Arg
                405                 410                 415
Asp Leu Ile Ser Glu Ile Asp Ala Lys Ala Asn Ala Ile Asn His Glu
            420                 425                 430
Met Arg Ser Ile Gln Arg Gln Ala Glu Ser Lys Thr Lys Ser Leu Thr
        435                 440                 445
Thr Thr Asp Lys Ile Gly Ile Leu Asn Gln Asp Gln Asp Leu Lys Glu
        450                 455                 460
Val Arg Asp Ala Val Leu Met Val Arg Glu His Pro Glu Met Lys Asp
465                 470                 475                 480
Lys Ile Leu Glu Pro Pro Ile Met Thr Val Ser Ala Ile Asn Ala Gln
                485                 490                 495
Phe Ala Ala Tyr Leu Ala Gln Cys Val Asp Tyr Asn Thr Ser Lys Ala
            500                 505                 510
Leu Thr Val Val Asp Ser Asp Ser Tyr Lys Leu Phe Ala Asn Pro Ile
        515                 520                 525
Leu Asp Lys Phe Lys Val Asn Leu Arg Glu Leu Ser Ser Ala Asp Thr
        530                 535                 540
Thr Pro Pro Val Pro Ala Glu Thr Val Arg Asp Leu Gly Phe Glu Gly
545                 550                 555                 560
Tyr Leu Ser Asp Phe Ile Thr Gly Asp Lys Arg Val Met Lys Met Leu
                565                 570                 575
Cys Gln Thr Ser Lys Ile His Thr Ile Pro Val Ser Arg Arg Glu Leu
            580                 585                 590
Thr Pro Ala Gln Ile Lys Lys Leu Ile Thr Pro Arg Pro Asn Gly Lys
```

-continued

```
            595                 600                 605
Ile Leu Phe Lys Arg Ile Ile His Gly Asn Arg Leu Val Asp Ile Lys
            610                 615                 620
Gln Ser Ala Tyr Gly Ser Lys Gln Val Phe Pro Thr Asp Val Ser Ile
625                 630                 635                 640
Lys Gln Thr Asn Phe Tyr Gln Gly Ser Ile Met Ser Asn Glu Gln Lys
                645                 650                 655
Ile Arg Ile Glu Asn Glu Ile Ile Asn Leu Lys Asn Glu Tyr Asn Asp
            660                 665                 670
Arg Lys Ser Thr Leu Asp Ala Leu Ser Asn Gln Lys Ser Gly Tyr Arg
                675                 680                 685
His Glu Leu Ser Glu Leu Ala Ser Lys Asn Asp Asp Ile Asn Arg Glu
            690                 695                 700
Ala His Gln Leu Asn Glu Ile Arg Lys Lys Tyr Thr Met Arg Lys Ser
705                 710                 715                 720
Thr Ile Glu Thr Leu Arg Glu Lys Leu Asp Gln Leu Lys Arg Glu Ala
                725                 730                 735
Arg Lys Asp Val Ser Gln Lys Ile Lys Asp Ile Asp Asp Gln Ile Gln
            740                 745                 750
Gln Leu Leu Lys Gln Arg His Leu Leu Ser Lys Met Ala Ser Ser
            755                 760                 765
Met Lys Ser Leu Lys Asn Cys Gln Lys Glu Leu Ile Ser Thr Gln Ile
770                 775                 780
Leu Gln Phe Glu Ala Gln Asn Met Asp Val Ser Met Asn Asp Val Ile
785                 790                 795                 800
Gly Phe Phe Asn Glu Arg Glu Ala Asp Leu Lys Ser Gln Tyr Glu Asp
                805                 810                 815
Lys Lys Lys Phe Val Lys Glu Met Arg Asp Thr Pro Glu Phe Gln Ser
                820                 825                 830
Trp Met Arg Glu Ile Arg Ser Tyr Asp Gln Asp Thr Lys Glu Lys Leu
            835                 840                 845
Asn Lys Val Ala Glu Lys Tyr Glu Glu Glu Gly Asn Phe Asn Leu Ser
            850                 855                 860
Phe Val Gln Asp Val Leu Asp Lys Leu Glu Ser Glu Ile Ala Met Val
865                 870                 875                 880
Asn His Asp Glu Ser Ala Val Thr Ile Leu Asp Gln Val Thr Ala Glu
                885                 890                 895
Leu Arg Glu Leu Glu His Thr Val Pro Gln Ser Lys Asp Leu Glu
            900                 905                 910
Thr Ile Lys Ala Lys Leu Lys Glu Asp His Ala Val Leu Glu Pro Lys
            915                 920                 925
Leu Asp Asp Ile Val Ser Lys Ile Ser Ala Arg Phe Ala Arg Leu Phe
930                 935                 940
Asn Asn Val Gly Ser Ala Gly Ala Val Arg Leu Glu Lys Pro Lys Asp
945                 950                 955                 960
Tyr Ala Glu Trp Lys Ile Glu Ile Met Val Lys Phe Arg Asp Asn Ala
                965                 970                 975
Pro Leu Lys Lys Leu Asp Ser His Thr Gln Ser Gly Gly Glu Arg Ala
                980                 985                 990
Val Ser Thr Val Leu Tyr Met Ile Ala Leu Gln Glu Phe Thr Ser Ala
                995                 1000                1005
Pro Phe Arg Val Val Asp Glu Ile Asn Gln Gly Met Asp Ser Arg Asn
            1010                1015                1020
```

```
Glu Arg Ile Val His Lys Ala Met Val Glu Asn Ala Cys Ala Glu Asn
1025                1030                1035                1040

Thr Ser Gln Tyr Phe Leu Ile Thr Pro Lys Leu Leu Thr Gly Leu His
            1045                1050                1055

Tyr His Glu Lys Met Arg Ile His Cys Val Met Ala Gly Ser Trp Ile
        1060                1065                1070

Pro Asn Pro Ser Glu Asp Pro Lys Met Ile His Phe Gly Glu Thr Ser
    1075                1080                1085

Asn Tyr Ser Phe Asp
    1090

<210> SEQ ID NO 53
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 53
agagttcaac caaagatgga tgtccacgag gtctctagtg agcgcctcgc atctatcgta      60
cgctgcaggt cgac                                                       74

<210> SEQ ID NO 54
<211> LENGTH: 74
<212> TYPE: DNA
<213> ORGANISM: Artificial Sequence
<220> FEATURE:
<223> OTHER INFORMATION: Description of Artificial Sequence: primer

<400> SEQUENCE: 54
atagtattat gcttattacg gtgtcggtct cgtagaggcc atgcttccat agtatatcga      60
tgaattcgag ctcg                                                       74

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 55
ttctttatac attcgtcagg tgttgaaaga gttcaaccaa agatg                     45

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 56
atatacaatg ttatgtaaaa ctctctgata gtattatgct tatta                     45

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 57
agttttgcat agcattgttt gaagt                                           25
```

```
<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 58
ctacaatact gaaggacatg acgtg                                      25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 59
agatgataaa atatgggtga ggaca                                      25

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 60
ttattggttg ttccaaatcc tttta                                      25

<210> SEQ ID NO 61
<211> LENGTH: 876
<212> TYPE: DNA
<213> ORGANISM: Saccharomyces cerevisiae

<400> SEQUENCE: 61
atgtcttcta tctacaaagc cctcgcagga aagagcaaag ataataaatc tgaaagaag    60 caaggcaatg tcaagcaatt tatgaacaag caaagaactc ttctgatttc gagtagaggt  120
gttaactata gacatcgtca tttaattcaa gacttaagcg gattattgcc tcattccaga  180
aaggagccaa aattggatac taaaaaggat cttcaacagt tgaacgaaat cgctgagttg  240
tacaattgta ataatgttct attctttgag gccagaaaac accaagattt gtatctatgg  300
ttatccaagc cgccaaatgg gccaactata aaattttaca ttcaaaactt gcatactatg  360
gatgagttga attttacagg taactgttta aagggttctc gtccggtatt gtcgtttgat  420
caacgtttcg aatcctcccc acactaccaa ttaattaagg agttgctagt gcataatttt  480
tgtgtaccac caaatgctag aaaatctaag ccatttattg atcacgtcat gtccttcagt  540
attgtagatg ataaaatatg ggtgaggaca tatgagatct cacacagtac taagaacaaa  600
gaagaatatg aagatggcga agaagacata tcattagtgg aaattggccc taggtttgtt  660
atgactgtca ttttgatcct agaaggttca tttggtggtc caaagatcta tgaaaataaa  720
caatatgttt cgccaaacgt cgtaagagct caaattaaac aacaagctgc tgaggaggca  780
aagtctagag ctgaagctgc tgtggaaaga aaaattaaga gaagagagaa tgttcttgcc  840
gccgatcctt tatcaaacga tgccttgttt aaataa                            876

<210> SEQ ID NO 62
<211> LENGTH: 291
<212> TYPE: PRT
```

```
<213> ORGANISM: Saccharomyces cerevisiae

<400> SEQUENCE: 62

Met Ser Ser Ile Tyr Lys Ala Leu Ala Gly Lys Ser Lys Asp Asn Lys
 1               5                  10                  15

Ser Glu Lys Lys Gln Gly Asn Val Lys Gln Phe Met Asn Lys Gln Arg
                 20                  25                  30

Thr Leu Leu Ile Ser Ser Arg Gly Val Asn Tyr Arg His Arg His Leu
             35                  40                  45

Ile Gln Asp Leu Ser Gly Leu Leu Pro His Ser Arg Lys Glu Pro Lys
         50                  55                  60

Leu Asp Thr Lys Lys Asp Leu Gln Gln Leu Asn Glu Ile Ala Glu Leu
 65                  70                  75                  80

Tyr Asn Cys Asn Asn Val Leu Phe Phe Glu Ala Arg Lys His Gln Asp
                 85                  90                  95

Leu Tyr Leu Trp Leu Ser Lys Pro Pro Asn Gly Pro Thr Ile Lys Phe
                100                 105                 110

Tyr Ile Gln Asn Leu His Thr Met Asp Glu Leu Asn Phe Thr Gly Asn
            115                 120                 125

Cys Leu Lys Gly Ser Arg Pro Val Leu Ser Phe Asp Gln Arg Phe Glu
130                 135                 140

Ser Ser Pro His Tyr Gln Leu Ile Lys Glu Leu Leu Val His Asn Phe
145                 150                 155                 160

Cys Val Pro Pro Asn Ala Arg Lys Ser Lys Pro Phe Ile Asp His Val
                165                 170                 175

Met Ser Phe Ser Ile Val Asp Asp Lys Ile Trp Val Arg Thr Tyr Glu
                180                 185                 190

Ile Ser His Ser Thr Lys Asn Lys Glu Glu Tyr Glu Asp Gly Glu Glu
            195                 200                 205

Asp Ile Ser Leu Val Glu Ile Gly Pro Arg Phe Val Met Thr Val Ile
        210                 215                 220

Leu Ile Leu Glu Gly Ser Phe Gly Gly Pro Lys Ile Tyr Glu Asn Lys
225                 230                 235                 240

Gln Tyr Val Ser Pro Asn Val Val Arg Ala Gln Ile Lys Gln Gln Ala
                245                 250                 255

Ala Glu Glu Ala Lys Ser Arg Ala Glu Ala Ala Val Glu Arg Lys Ile
                260                 265                 270

Lys Arg Arg Glu Asn Val Leu Ala Ala Asp Pro Leu Ser Asn Asp Ala
            275                 280                 285

Leu Phe Lys
        290
```

ESSENTIAL GENES OF YEAST AS TARGETS FOR ANTIFUNGAL AGENTS, HERBICIDES, INSECTICIDES AND ANTI-PROLIFERATIVE DRUGS

1. FIELD OF THE INVENTION

The present invention relates to genes in *Saccharomyces cerevisiae* which are essential for germination and proliferation of *S. cerevisiae* and using the identified genes or their encoded proteins as targets for highly specific antifungal agents, insecticides, herbicides and anti-proliferation drugs. Specifically, the present invention relates to essential genes YDR141C, YDR091C, YOL022C, YOL026C, YOL034W, and YOL077C. The present invention provides antisense molecules and ribozymes comprising sequences complementary to the sequences of mRNAs of essential genes that function to inhibit the essential genes. The present invention also provides neutralizing antibodies to proteins encoded by essential genes that bind to and inactivate the essential gene products.

2. BACKGROUND OF THE INVENTION

Fungal pathogens are responsible for a large number of diseases in humans, animals and plants. Fungal diseases often occur as opportunistic infections in humans who have a suppressed immune system, such as in patients with AIDS, leukemia, or diabetes mellitus, or in patients receiving immunosuppressive drugs or chemotherapy. Fungal infections are a significant problem in veterinary medicine as well, and fungal diseases also affect plant crops which are critical to the agricultural industry. Since fungi are eukaryotic cells, many metabolic pathways and genes of fungi are similar to those of mammalian and/or plant cells. Therefore, treatment of fungal diseases is frequently hindered because antifungal agents are often toxic to mammalian or plant cells.

The most widely used class of antifungal compounds in human medicine is the family of azole compounds, which are used to treat both systemic and topical fungal infections. The common target of all azole compounds is the cytochrome P450 lanosterol 14α-demethylase. Lanosterol demethylase is an essential gene required for the intracellular biosynthesis of sterols, which are critical components of biological membranes. In *S. cerevisiae*, the ERG11 gene encodes lanosterol demethylase. Although azole compounds are effective antifungal inhibitors, the enzymes involved in sterol biosynthesis are highly conserved in all eukaryotic cells. Lanosterol demethylases from all eukaryotic cells, including human, exhibit a high degree of nucleotide sequence identity, as shown in FIG. 7. Thus, the azoles inhibit lanosterol demethylase from the host cell as well as lanosterol demethylase from yeast, which causes undesirable side effects upon administration. These side effects may be especially deleterious in patients who are already immunocompromised because it may make them more susceptible to other opportunistic infections. Therefore, the identification of new targets for new antifungal compounds with fewer side effects is an active area of clinical research.

The use of herbicides and insecticides are critical in agriculture to ensure an adequate food supply for a growing world population. One problem with current herbicides and insecticides is that agricultural pests often become resistant to them. Another problem is that many pesticides currently in use are highly toxic to farmworkers working in the fields, humans or animals who eat the food produced by the treated crops, or other plant and animal species that come in contact with the pesticide through soil, water or air contamination. Thus, new herbicides and insecticides that are less toxic to humans and animals and that are effective against resistant species of weeds and insects are desirable.

Drugs to prevent proliferation are critical in the treatment of diseases characterized by uncontrolled or poorly controlled cell proliferation. For instance, anti-proliferation drugs are used to treat many types of cancer, benign tumors, psoriasis, and to prevent restenosis after angioplasty. Identifying new targets for anti-proliferation drugs is an active area of research because different cells, especially malignant cells, vary dramatically in their responses to particular anti-proliferation drugs. It is often the case that an anti-proliferation drug will inhibit cell proliferation in one cell type but be ineffective in another cell type. Thus, the identification of new anti-proliferation drugs, directed against novel targets, provides a larger arsenal from which a physician can treat a patient with a cell proliferation disorder.

As discussed above, identifying new targets and compounds for antifungal drugs, herbicides, insecticides and anti-proliferation agents is critical for improvements in agriculture and in veterinary and human health. One promising avenue for identifying targets and compounds is the information contained within the complete genomic sequence of baker's yeast, *Saccharomyces cerevisiae*. *S. cerevisiae* has long been used as a model for eukaryotic cells. *S. cerevisiae* shares many basic cellular functions with other eukaryotic cells, including vertebrate, insect and plant cells. Furthermore, it is easy to grow *S. cerevisiae* and to manipulate its genes. Many of the genes of *S. cerevisiae* are specific to *S. cerevisiae* or to fungi in general, and have no homologs in other eukaryotic organisms. However, many genes from *S. cerevisiae* exhibit significant homology to genes in other organisms, including mammals, plants and insects.

The sequencing of the *S. cerevisiae* genome marked the first complete, ordered set of genes from a eukaryotic organism. The sequencing of *S. cerevisiae* revealed the presence of over 6,000 genes on 16 chromosomes (Mewes et al. (1997) *Nature* 387:7–65; Goffeau et al. (1996) *Science* 274:546–67). The sequence of the roughly 6,000 ORFs in the yeast genome is compiled in the Saccharomyces Genome Database (SGD). The SGD provides Internet access to the complete genomic sequence of *S. cerevisiae*, ORFS, and the putative polypeptides encoded by these ORFs. The SGD can be accessed via the World Wide Web. A gazetteer and genetic and physical maps of *S. cerevisiae* is found in Mewes et al., 1997. References therein also contain the sequence of each chromosome of *S. cerevisiae*.

Approximately half of the putative proteins encoded by the open reading frames (ORF) identified in the sequencing of the yeast genome have no known function. The function of many others is assigned only by structural similarity to homologous proteins in other cell types. Thus, the role of many genes in *S. cerevisiae* is unknown. However, in order to use the information gathered from the sequencing of *S. cerevisiae* most efficiently for identifying targets or compounds for antifungal and anti-proliferation drugs, as well as herbicides and insecticides, the function of the many *S. cerevisiae* genes must be identified.

Citation of a reference herein shall not be construed as indicating that such reference is prior art to the present invention.

3. SUMMARY OF THE INVENTION

This invention provides genes in *S. cerevisiae*, a budding yeast, which are essential for germination or proliferation.

The essential genes are useful as targets for new antifungal agents, insecticides, herbicides and anti-proliferation drugs. Specifically, the invention provides yeast essential genes YDR141C, YDR091C, YOL022C, YOL026C, YOL034W, and YOL077C.

The invention provides a method of comparing the sequences of the essential S. cerevisiae genes to sequences from plants, insects and vertebrates, including humans and non-human mammals, to determine whether the essential S. cerevisiae genes have any homologs in these higher eukaryotes. If no human or mammalian homologs exist, the S. cerevisiae genes themselves, or the proteins which these genes encode, provide targets for the design or discovery of highly specific antifungal agents for use in human patients or in veterinary settings. Similarly, if no plant homologs exist, the S. cerevisiae genes or their encoded proteins provide targets for the production of highly specific antifungal agents for plants. The advantage of the method is that the new antifungal agents would be expected to have few or no side effects in human or non-human mammals or in plants. The invention further encompasses methods of identifying antifungal targets from fungi other than S. cerevisiae, including Aspergillus and Candida.

The invention also encompasses methods of identifying targets for herbicides and insecticides when an essential S. cerevisiae gene has either or both a plant or insect homolog, respectively. The method comprises the steps of identifying essential S. cerevisiae genes and comparing the sequence of the essential S. cerevisiae gene to sequences from plants and/or insects. If a plant or insect homolog exists, the method comprises the step of determining whether the plant or insect homolog is critical to growth or proliferation. If the plant or insect homolog is critical for growth or proliferation, the insect, plant or yeast gene and/or its encoded protein can be used as targets for the design and discovery of new herbicides and insecticides.

The invention also includes a method of identifying targets for anti-proliferation drugs in cases in which an essential S. cerevisiae gene has a human or non-human mammalian homolog. After identification of an essential S. cerevisiae gene, the method comprises determining whether a human or non-human mammalian homolog exists. The method further comprises the step of determining if the mammalian or human homolog is important for cell proliferation. If the identified human or mammalian gene is important for cell proliferation, the human, mammalian or yeast gene or its encoded protein can be used as targets in the design of new anti-proliferation drugs.

An essential gene from S. cerevisiae, YDR141C (FIG. 4) has been identified. The polypeptide encoded by this gene (FIG. 5), Ydr141cp has a weak homolog (Type 2, see below) in C. elegans, and no homology to any known plant, insect, mammalian or other vertebrate polypeptide (FIG. 6). The invention thus provides the polynucleotide sequence of YDR141C (FIG. 4, SEQ ID NO: 11) and vectors and host cells comprising YDR141C for use in methods of identifying, designing and discovering highly specific antifungal agents. The invention also provides the amino acid sequence of Ydr141cp (FIG. 5, SEQ ID NO: 12), a method of recombinantly producing Ydr141 cp for use as a target, and a method for producing antibodies directed against Ydr141cp.

A number of other essential genes in S. cerevisiae have been identified, including YDR091C (FIG. 10, SEQ ID NO: 21), YOL022C (FIG. 17, SEQ ID NO: 31) YOL026C (FIG. 22, SEQ ID NO: 41), YOL034W (FIG. 27, SEQ ID NO: 51) and YOL077C (FIG. 33, SEQ ID NO: 61). These genes were previously identified only as hypothetical ORFs and had no known function. The polypeptide encoded by YDR091C (FIG. 11, SEQ ID NO: 22) has strong Type 1 homologs (defined below) in Pyrococcus, Methanococcus, Methanobacterium, Archaeoglobus, and Homo sapiens, as well as many weak Type 2 homologs in, inter alia, Arabidopsis, Synechocystis, Lactobacillus, Staphylococcus, and B. subtilis (FIG. 12). The polypeptide encoded by YDR091C has 68% sequence identity (82% sequence homology) to the H. sapiens RNase L inhibitor (FIG. 13) and 65% sequence identity (81% sequence homology) to the H. sapiens 2'-5' oligoadenylate binding protein (FIG. 14). The polypeptide encoded by YOL022C (FIG. 18, SEQ ID NO: 32) has a strong homolog (Type 1 homolog) in its own genome, and a weak homolog in S. pombe (FIG. 19). The polypeptide encoded by YOL026C (FIG. 23, SEQ ID NO: 42) has been identified as a previously-known membrane protein with no significant homologies to any other known proteins (FIG. 24). The polypeptide encoded by YOL034W (FIG. 28, SEQ ID NO: 52) has a strong homologs in S. pombe, C. elegans, and H. sapiens, and weak homologs in, inter alia, its own genome, Methanococcus, Mycoplasma, and Entamoeba (FIG. 29). The polypeptide encoded by YOL034W exhibits 23% sequence identity (43% sequence homology) to an H. sapiens brain protein of unknown function (FIG. 30). The polypeptide encoded by YOL077C (FIG. 34, SEQ ID NO: 62) has a strong homolog in C. elegans (FIG. 35). The polypeptide exhibits 44% sequence identity (66% sequence homology) to the C. elegans protein, which has an unknown function (FIG. 36). Amino acid sequence alignments of portion of Yo1077cp (SEQ ID NO: 62) and ESTs from the C. albicans genome show that the polypeptide has one Type 1 homolog and two Type 2 homologs in the C. albicans genome (FIG. 37).

The invention provides the polynucleotide sequences of these ORFs and vectors and host cells comprising these OhPFs for use in methods of identifying, designing and discovering highly specific antifungal agents. The invention also provides a methods of recombinantly producing the protein encoded these ORFs for use as a target in methods of identifying, designing and discovering highly specific antifungal agents and for producing antibodies directed against the encoded protein.

Highly specific antifungal compounds encompassed by this invention include antisense polynucleotides that target RNAs transcribed from YDR141C, YDR091C, YOL022C, YOL026C, YOL034W, and YOL077C. Highly specific antifungal compounds also include ribozymes that cleave YDR141C, YDR091C, YOL022C, YOL026C, YOL034W, or YOL077C polynucleotides. The invention also encompasses antibodies which bind to and neutralize Ydr141cp or the proteins encoded by the YDR091C, YOL022C, YOL026C, YOL034W, and YOL077C ORFs. The invention also encompasses small organic molecules which inhibit Ydr141cp activity or the activity of the YDR091C, YOL022C, YOL026C, YOL034W, or YOL077C encoded proteins. Also contemplated are methods for specific inhibition of transcription of YDR141C, YDR091C, YOL022C, YOL026C, YOL034W, or YOL077C by inhibiting specific transcriptional factors or combinations of such factors. The invention also provides methods of isolating highly specific antifungal compounds using Ydr141cp or the proteins encoded by one of the YDR091C, YOL022C, YOL026C, YOL034W, or YOL077C ORFs.

4. BRIEF DESCRIPTION OF THE DRAWINGS

FIG. 1. A one-step, PCR based strategy for the construction of a yeast strain containing a specific gene deletion, e.g., a "knock-out" mutation (Rothstein (1991) *Methods Enzymol.* 194:281–301). Two rounds of PCR are utilized to produce a DNA molecule containing the KanMX marker flanked by 45 basepairs of the yeast sequence immediately upstream of the start codon of the target gene and 45 basepairs of the yeast sequence immediately downstream of the stop codon of the target gene. In round 1, primer pair UPTAG and DOWNTAG are used to produce a DNA molecule having 18 basepairs of yeast sequence upstream of the start codon of the target gene and 19 basepairs of yeast sequence downstream of the stop codon of the target gene at the ends of the DNA molecule. In round 2, the primer pair UPSTREAM45 and DOWNSTREAM45 are used to produce a DNA molecule having 45 base pairs of the yeast sequence both upstream and downstream of the target gene at the end of the DNA molecule. The DNA is then transformed into yeast (Ito el al. (1983) *J Bacteriol.* 153:163–68; Schiestl & Gietz (1989) *Curr. Genet.* 16: 339–46) where the integration event is targeted to the correct locus by homologous recombination. The resulting mutant allele is a precise replacement of the targeted open reading frame with the KanMX marker (Wach et al. (1994) *Yeast* 10:1793–1808). The KanMX marker confers resistance to the drug G-418.

Figure 2:
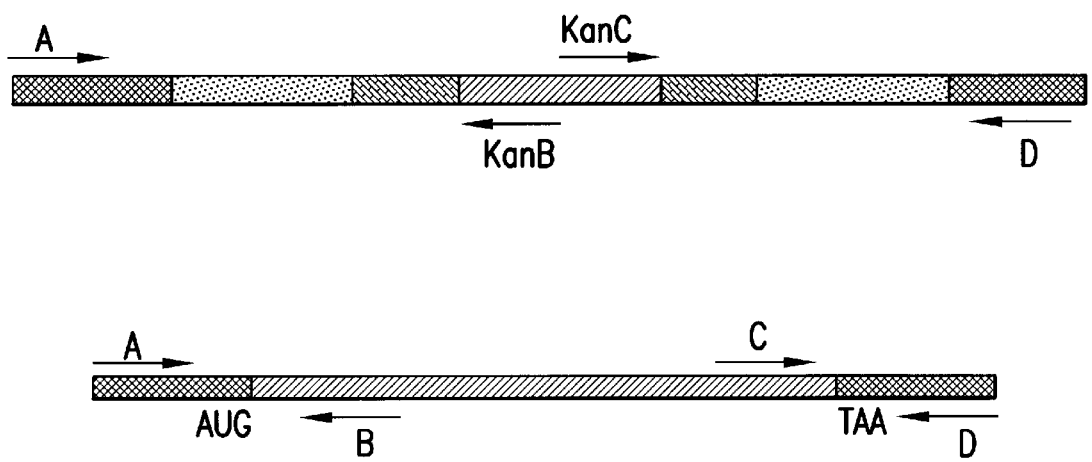

FIG. 2. A PCR based strategy for the analysis of the knock-out mutation. Four primers (A, B, C, and D) are gene specific (i.e. YFR003C, YGR277C, YGR278W YKR071C, YKR079C, or YKR083C), and two primers are marker specific (KanB and KanC). The wildtype allele produces PCR products of predicted sizes with primer pairs AB, CD, and AD, but not with pairs AKanB and KanCD. The mutant allele produces PCR products of predicted sizes with primer pairs AKanB, KanCD, and AD, but not with pairs AB and CD.

FIG. 3. The ten oligonucleotides used as PCR primers for the construction and analysis of the YDR141C knock-out mutant. Four of the primers were used to construct the DNA molecule use to transform yeast: UPTAG (SEQ ID NO: 1), DOWNTAG (SEQ ID NO: 2), Upstream45 (SEQ ID NO: 3), and Downstream45 (SEQ ID NO: 4). The other six primers were used to analyze the mutant allele: A (SEQ ID NO: 5), B (SEQ ID NO: 6), C (SEQ ID NO: 7), D (SEQ ID NO: 8), KanB (SEQ ID NO: 9), and KanC (SEQ ID NO: 10).

FIG. 4. Nucleotide sequence of the coding region of the *S. cerevisiae* gene YDR141C (SEQ ID NO: 11). There are 5,097 nucleotides including the start codon (ATG, in bold) and the stop codon (TGA, in bold).

FIG. 5. Amino acid sequence of the *S. cerevisiae* protein Ydr141cp (SEQ ID NO: 12) as predicted by the nucleotide sequence of the YDR141C gene. The gene encodes a protein of 1,698 amino acids.

FIG. 6. Blastp (Altschul et al. (1997) *Nucleic Acids Res.* 25:3389–402) search results of the yeast protein Yfr003cp against the amino acid sequences in the Swiss protein database swissprot shows that this polypeptide has a weak homolog in *C. elegans*.

FIG. 7. Blastp (Altschul et al., 1997) search results of the yeast protein Erg11p (cytochrome P450 lanosterol 14α-demethylase) against the Swiss protein database. Cytochrome P450 lanosterol 14α-demethylase proteins from numerous species show significant sequence homologies.

Figure 8:
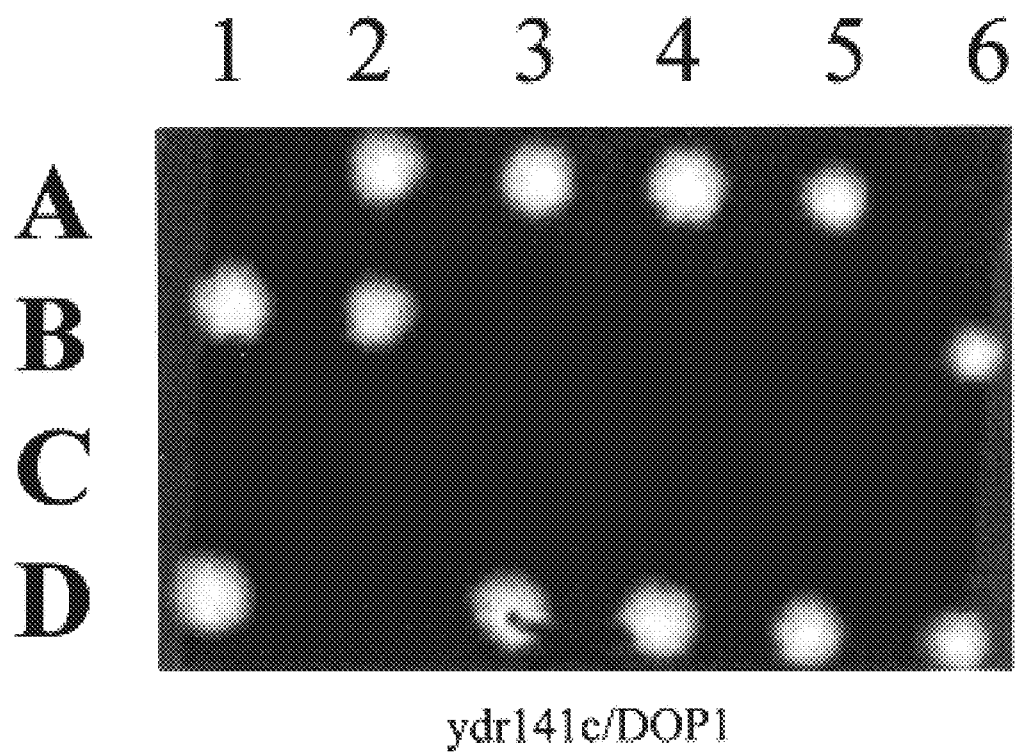

FIG. 8. Lethality of a YDR141C null mutation. A diploid strain containing a heterozygous null mutation of the YDR141C gene (marked by the KanMX gene conferring resistance to the drug G-418) was sporulated and dissected. The four spores of each tetrad were placed in a vertical line (labeled A, B, C and D), and allowed to germinate on rich medium. Six complete tetrads are shown. The observed lethality co-segregated with G-418 resistance, indicating that the lethality was due to the KanMX-marked YDR141 C deletion mutation.

FIG. 9. The ten oligonucleotides used as PCR primers for the construction and analysis of the YDR091C knock-out mutant. Four of the primers were used to construct the DNA molecule use to transform yeast: UPTAG (SEQ ID NO: 13), DOWNTAG (SEQ ID NO: 14), Upstream45 (SEQ ID NO: 15), and Downstream45 (SEQ ID NO: 16). The other six primers were used to analyze the mutant allele: A (SEQ ID NO: 17), B (SEQ ID NO: 18), C (SEQ ID NO: 19), D (SEQ ID NO: 20), KanB (SEQ ID NO: 9), and KanC (SEQ ID NO: 10).

FIG. 10. Nucleotide sequence of the coding region of the *S. cerevisiae* gene YDR091C (SEQ ID NO: 21). The gene comprises 1,827 nueleotides of coding sequence including the start codon (ATG, in bold) and the stop codon (TAA, in bold).

FIG. 11. The predicted amino acid sequence of the *S. cerevisiae* protein encoded by the YDR091C gene, Ydr091cp (SEQ ID NO: 22). The gene encodes a protein of 608 amino acids.

FIG. 12. Blastp (Altschul et al., 1997) search results of the yeast protein Ydr091 cp against the NCBI non-redundant database. Ydr091p has strong Type 1 homologs in Pyrococcus, Methanococcus, Methanobacterium, Archaeoglobus, and *Homo sapiens*, as well as many weak Type 2 homologs in, inter alia, Arabidopsis, Synechocystis, Lactobacillus, Staphylococcus, and *B. subtilis*.

FIG. 13. Blast (Altschul et al., 1997) alignment of Ydr091cp with the human RNase L inhibitor. The Ydr091cp polypeptide exhibits 68% sequence identity (82% sequence homology) with the *H. sapiens* RNase L inhibitor protein.

FIG. 14. Blast (Altschul et al., 1997) alignment of Ydr091cp with the human 2'–5' oligoadenylate binding protein. The Ydr091cp polypeptide exhibits 65% sequence identity (81% sequence homology) with the *H. sapiens* 2'–5' oligoadenylate binding protein.

Figure 15:
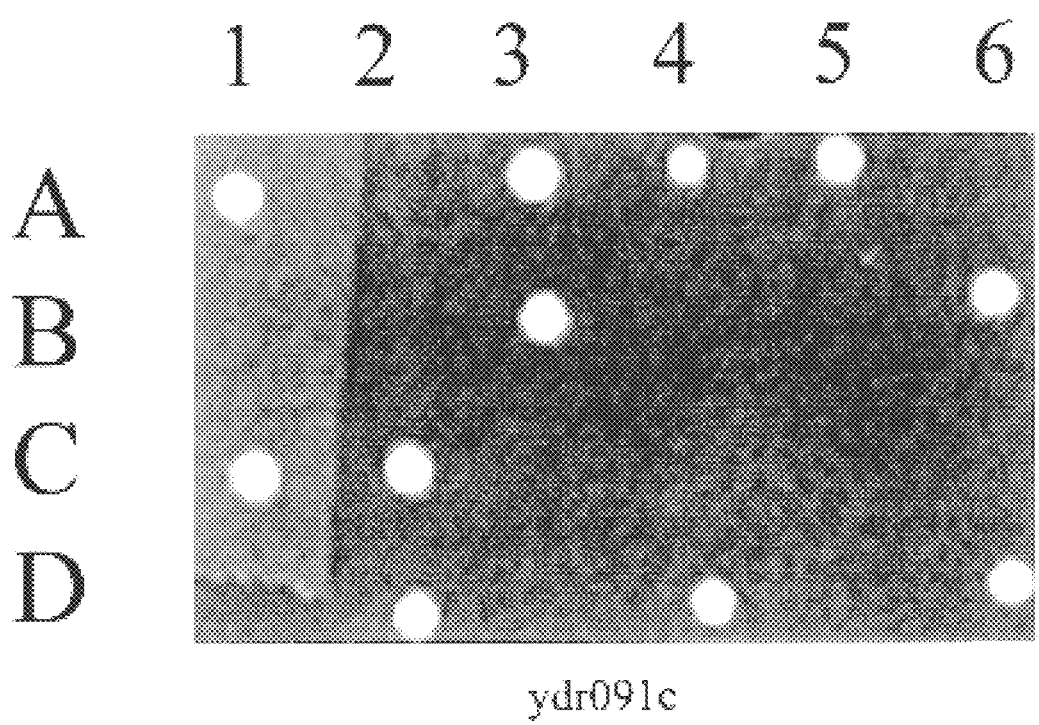

FIG. 15. Lethality of a YDR091C null mutation. A diploid strain containing a heterozygous null mutation of the YDR091C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YDR091C deletion mutation.

FIG. 16. The ten oligonucleotides used as PCR primers for the construction and analysis of the YOL022C knock-out mutant. Four of the primers were used to construct the DNA molecule use to transform yeast: UPTAG (SEQ ID NO: 23), DOWNTAG (SEQ ID NO: 24), Upstream45 (SEQ ID NO: 25), and Downstream45 (SEQ ID NO: 26). The other six primers were used to analyze the mutant allele: A (SEQ ID NO: 27), B (SEQ ID NO: 28), C (SEQ ID NO: 29), D (SEQ ID NO: 30), KanB (SEQ ID NO: 9), and KanC (SEQ ID NO: 10).

FIG. 17. Nucleotide sequence of the coding region of the *S. cerevisiae* gene YOL022C (SEQ ID NO: 31). The gene comprises 1,227 nucleotides of coding sequence, including the start codon (ATG, in bold) and the stop codon (TGA, in bold).

FIG. 18. The predicted amino acid sequence of the *S. cerevisiae* protein encoded by the YOL022C gene, Yo1022cp (SEQ ID NO: 32). The gene encodes a protein of 408 amino acids.

FIG. 19. Blastp (Altschul et al., 1997) search results of the yeast protein Yo1022cp against the NCBI non-redundant database, supra. The polypeptide encoded by YOL022C, Yo1022cp (SEQ ID NO: 32), has a strong homolog (Type 1) in its own genome, and a weak homolog in S. pombe.

Figure 20:
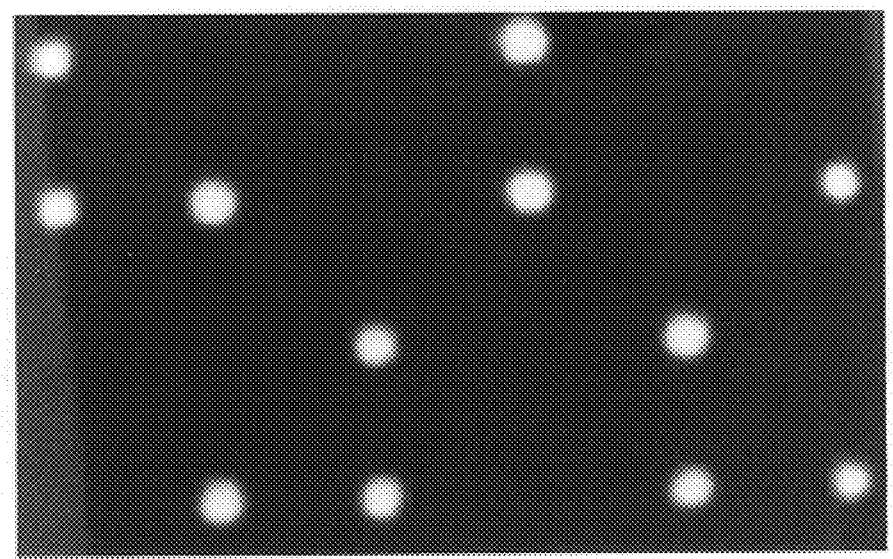

FIG. 20. Lethality of a YOL022C null mutation. A diploid strain containing a heterozygous null mutation of the YOL022C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YOL022C deletion mutation.

FIG. 21. The ten oligonucleotides used as PCR primers for the construction and analysis of the YOL026C knock-out mutant. Four of the primers were used to construct the DNA molecule use to transform yeast: UPTAG (SEQ ID NO: 33), DOWNTAG (SEQ ID NO: 34), Upstream45 (SEQ ID NO: 35), and Downstream45 (SEQ ID NO: 36). The other six primers were used to analyze the mutant allele: A (SEQ ID NO: 37), B (SEQ ID NO: 38), C (SEQ ID NO: 39), D (SEQ ID NO: 40), KanB (SEQ ID NO: 9), and KanC (SEQ ID NO: 10).

FIG. 22. Nucleotide sequence of the coding region of the S. cerevisiae gene YOL026C (SEQ ID NO: 41). The gene comprises 342 nucleotides of coding sequence, including the start codon (ATG, in bold) and the stop codon (TAA, in bold).

FIG. 23. The predicted amino acid sequence of the S. cerevisiae protein encoded by the YOL026C gene, Yo1026cp (SEQ ID NO: 42). The gene encodes a protein of 113 amino acids.

FIG. 24. Blast (Altschul et al., 1997) search results only identified the Yo1026cp protein itself and found no other sequence homologies.

Figure 25:
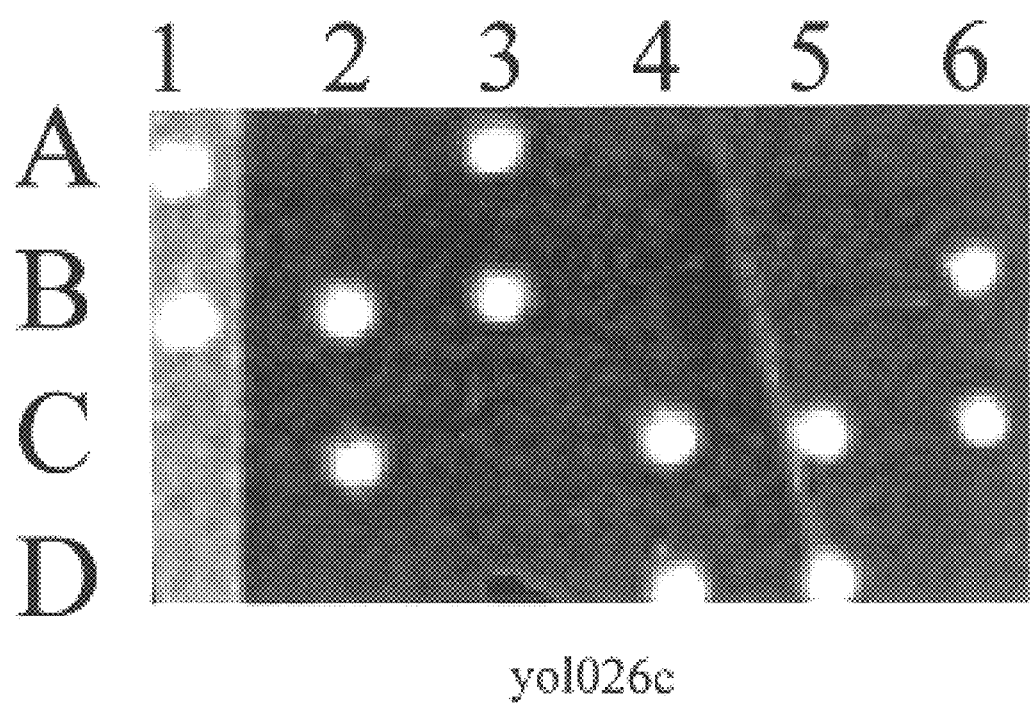

FIG. 25. Lethality of a YOL026C null mutation. A diploid strain containing a heterozygous null mutation of the YOL026C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YOL026C deletion mutation.

FIG. 26. The ten oligonucleotides used as PCR primers for the construction and analysis of the YOL034W knock-out mutant. Four of the primers were used to construct the DNA molecule use to transform yeast: UPTAG (SEQ ID NO: 43), DOWNTAG (SEQ ID NO: 44), Upstream45 (SEQ ID NO: 45), and Downstream45 (SEQ ID NO: 46). The other six primers were used to analyze the mutant allele: A (SEQ ID NO: 47), B (SEQ ID NO: 48), C (SEQ ID NO: 49), D (SEQ ID NO: 50), KarB (SEQ ID NO: 9), and KanC (SEQ ID NO: 10).

FIG. 27. Nucleotide sequence of the coding region of the S. cerevisiae gene YOL034W(SEQ ID NO: 51). The gene comprises 3,282 nucleotides of coding sequence, including the start codon (ATG, in bold) and the stop codon (TAA, in bold).

FIG. 28. The predicted amino acid sequence of the S. cerevisiae protein encoded by the YOL034W gene, Yo1034wp (SEQ ID NO: 52). The gene encodes a protein of 1,093 amino acids.

FIG. 29. Blastp (Altschul el al., 1997) search results of the yeast protein Yo1034wp against the NCBI non-redundanit database, supra. The polypeptide encoded by YOL034W, Yo1034wp (SEQ ID NO: 52), has a strong homologs in S. pombe, C. elegans, and H. sapiens, and weak homologs in, inter alia, its own genome, Methanococcus, Mycoplasma, and Entamoeba.

FIG. 30. Blast (Altschul et al., 1997) alignment of Yo1034wp shows that the polypeptide exhibits 23% sequence identity (43% sequence homology) to an H. sapiens brain protein of unknown function.

Figure 31:
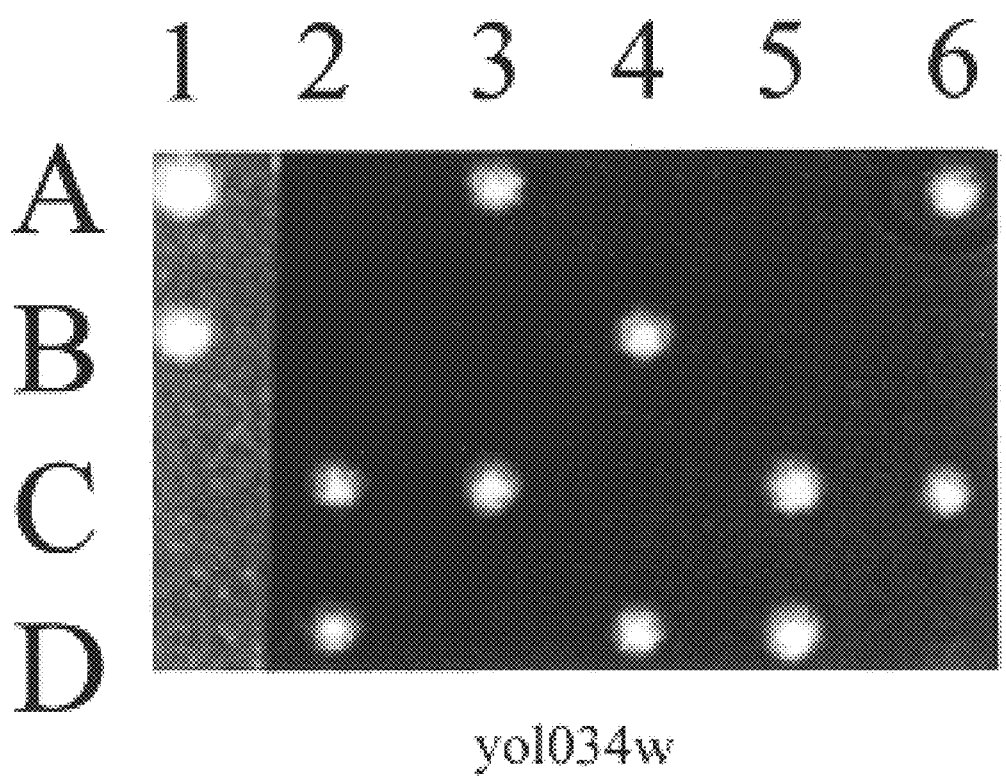

FIG. 31. Lethality of a YOL034W null mutation. A diploid strain containing a heterozygous null mutation of the YOL034 W gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YOL034W deletion mutation.

FIG. 32. The ten oligonucleotides used as PCR primers for the construction and analysis of the YOL077C knock-out mutant. Four of the primers were used to construct the DNA molecule use to transform yeast: UPTAG (SEQ ID NO: 53), DOWNTAG (SEQ ID NO: 54), Upstream45 (SEQ ID NO: 55), and Downstream45 (SEQ ID NO: 56). The other six primers were used to analyze the mutant allele: A (SEQ ID NO: 57), B (SEQ ID NO: 58), C (SEQ ID NO: 59), D (SEQ ID NO: 60), KanB (SEQ ID NO: 9), and KanC (SEQ ID NO: 10).

FIG. 33. Nucleotide sequence of the coding region of the S. cerevisiae gene YOL077C (SEQ ID NO: 61). The gene comprises 876 nucleotides of coding sequence, including the start codon (ATG, in bold) and the stop codon (TAA, in bold).

FIG. 34. The predicted amino acid sequence of the S. cerevisiae protein encoded by the YOL077C gene, Yo1077cp (SEQ ID NO: 62). The gene encodes a protein of 291 amino acids.

FIG. 35. Blast-p (Altschul et al., 1997) search results of the yeast protein Yo1077cp against the NCBI non-redundant database, supra. The polypeptide encoded by YOL077C, Yo1077cp (SEQ ID NO: 62), has a strong homolog in C. elegans.

FIG. 36. Blast (Altschul el al., 1997) alignment of Yo1077cp with a C. elegans protein shows that the polypeptide exhibits 44% sequence identity (66% sequence homology) to the C. elegans protein, which has an unknown function.

FIG. 37. Amino acid sequence alignments of portion of Yo1077cp and ESTs from the C. albicans genome show that the polypeptide has one Type 1 homolog and two Type 2 homologs in the C. albicans genome.

Figure 38:
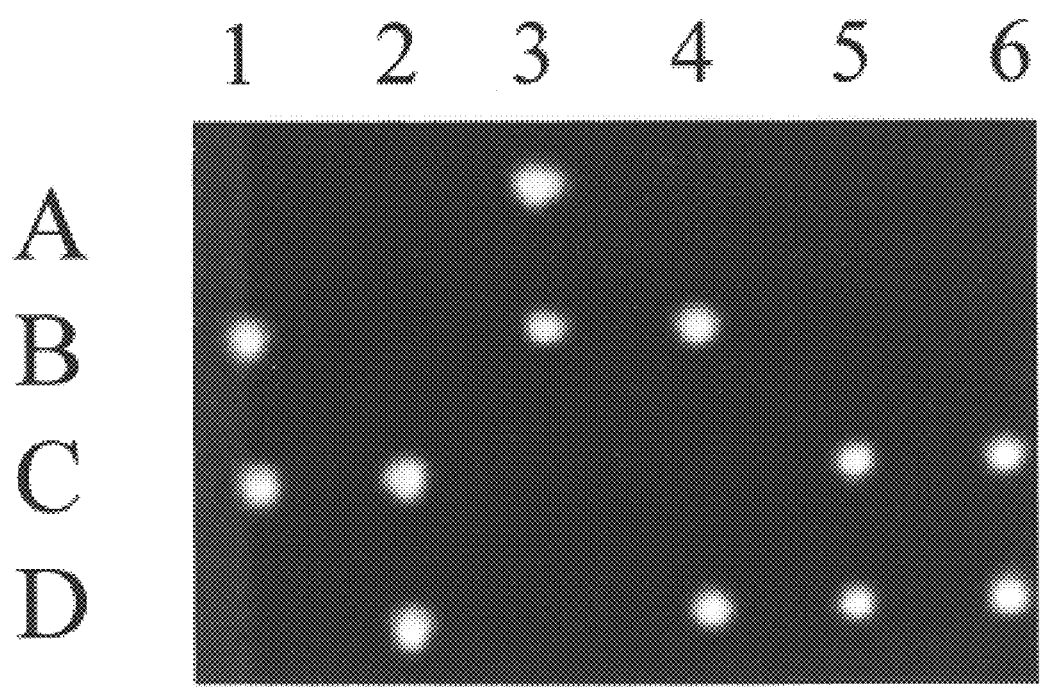

FIG. 38. Lethality of a YOL077C null mutation. A diploid strain containing a heterozygous null mutation of the YOL077C gene (marked by the KanMX gene conferring resistance to the drug G-418) was sporulated and dissected. The four spores of each tetrad were placed in a vertical line (labeled A, B, C and D) and allowed to germinate on rich medium. Six complete tetrads are shown. The observed lethality co-segregated with G-418 resistance, indicating that the lethality was due to the KanMX-marked YOL077C deletion mutation.

5. DETAILED DESCRIPTION OF THE INVENTION

5.1 Goals of the Invention

The essential genes from *S. cerevisiae* provide targets for the design or discovery of antifungal agents, herbicides and insecticides, and anti-proliferation drugs, that can be used in a variety of therapeutic, veterinary and agricultural settings.

Genes demonstrated to be essential in *S. cerevisiae* can be used to define a number of different categories of targets. Essential genes of *S. cerevisiae* that do not have plant and/or mammalian homologs can be used as targets for the design and discovery of highly specific antifungal agents. Alternatively, essential *S. cerevisiae* genes that have insect or plant homologs can be used as targets for the preparation of insecticides and herbicides, respectively. Lastly, essential *S. cerevisiae* genes that have mammalian homologs can be used as targets for the design of anti-proliferative agents, such as those that can be used in the treatment of psoriasis, prevention of restenosis after angioplasty, benign tumors and cancer, for example. These groups may not be mutually exclusive. For instance, an essential *S. cerevisiae* gene may have a plant homolog but no mammalian homolog. The gene or the protein it encodes may be used as a target to identify potential antifungal agents for mammals as well as a target to isolate herbicides which will be safe to mammals. Similarly, an essential *S. cerevisiae* gene may have plant, insect and mammalian homologs, and may be used as a target for the design or discovery of potential herbicides, insecticides and mammalian anti-proliferative agents.

A primary goal of the instant invention is thus to identify a new collection of antifungal targets for rational drug design based upon the sequence and function of *S. cerevisiae* genes.

The rationale underlying the identification of *S. cerevisiae* genes encoding new antifungal targets described here is two-fold. First, the genes encoding the potential antifungal targets must be essential for germination or vegetative growth. If a gene is essential, an inhibitor of the gene or its encoded protein will prevent germination or inhibit the growth of the cell. Second, the gene encoding the potential antifungal target preferably does not have a human or non-human mammalian homolog. If a target is to be useful for production of agricultural antifungal agents, it is preferable that the gene does not have a plant homolog. If the genes of a mammal or plant do not encode a protein that is homologous to the protein encoded by the essential *S. cerevisiae* gene, the targets defined by the essential *S. cerevisiae* genes have the potential to be highly fungal specific. Alternatively, if the target exhibits some homology with mammalian or plant proteins, antifungal agents may be designed to exploit the differences between the yeast target and the homologous mammalian or plant proteins to produce a specific antifungal agent. Finally, even if there is substantial homology between an essential *S. cerevisiae* gene or encoded protein and a mammalian or plant gene or encoded protein, the invention encompasses methods in which the *S. cerevisiae* gene or the protein target encoded by the gene can be used in the design or discovery of antifungal agents that can be selected or designed for few side effects in host organisms.

A second goal of the instant invention is the use of essential *S. cerevisiae* genes to identify novel targets for new herbicides and insecticides.

Genes that are homologous between *S. cerevisiae* and plants or insect not only exhibit sequence similarities but often exhibit functional similarities as well. Thus, if an *S. cerevisiae* gene is essential and is homologous to an insect or plant gene, there is a reasonable likelihood that the homologous insect or plant gene will be important for growth of the insect or plant as well.

Once a homologous gene to an essential *S. cerevisiae* gene has been identified, a number of techniques can be used to determine whether the homologous insect or plant gene is important or essential for insect or plant growth. For instance, one could knock out the homologous gene using standard genetic techniques in Drosophila, a well-characterized insect system, to determine whether the homologous insect gene is critical for cell proliferation in an insect. Similarly, the homologous gene could be knocked out in the well-characterized plant system Arabidopsis to determine whether the homologous plant gene is critical for germination or proliferation in a plant. If the homologous insect or plant gene is critical for growth and/or proliferation, the gene or its encoded protein can be used as a target for the design or discovery of insecticides or herbicides. One advantage of this approach is that previously unknown targets can be identified. Another advantage is that insecticides and herbicides designed to interact with certain specific targets may have fewer toxic side effects or be less likely to promote the development of resistance by a pest.

A third goal of the instant invention is to provide targets for the design of anti-proliferation drugs for mammals, especially humans.

As discussed above, genes from *S. cerevisiae* often have homologs in other eukaryotic organisms, including humans. Thus, if a gene is essential for proliferation in *S. cerevisiae*, there is a reasonable likelihood that the gene is also important for cell proliferation in vertebrates, including human and non-human mammals. Although many partial and full-length cDNAs have been identified in humans via expressed sequence tags (ESTs) and other large-scale sequencing schemes, the function of most of these sequenced cDNAs is as yet unknown. Once a vertebrate, preferably a human or non-human mammalian, gene homologous to an essential *S. cerevisiae* gene is identified, a variety of techniques can be used to determine whether the homologous gene is important for cell proliferation. For example, antisense molecules or ribozymes complementary to the vertebrate gene can be produced to determine if the inhibition of the gene inhibits cell proliferation. Alternatively, the gene can be deleted ("knocked out") in a cell line, a mouse or another transgenic organism.

If the homologous mammalian gene is critical for proliferation, the gene or its encoded protein can be used as a target for the design or discovery of anti-proliferation drugs. One advantage of this method is that genes previously unknown to be important for cell proliferation can be targeted. Anti-proliferation drugs directed against these targets may be more effective than those currently available, or they may be used in conjunction with currently available drugs to inhibit cell proliferation.

By systematically disrupting certain ORFs in the yeast genome or a portion thereof and determining whether the gene is essential to *S. cerevisiae* germination or vegetative growth, essential genes have been identified.

Second, the invention encompasses analyzing the collection of essential genes for sequence similarity to human, other mammalian and vertebrate, insect and plant genes, such that the genes or the proteins they encode can be used as targets for antifungal targets, insecticides, herbicides, or anti-proliferation drugs, as discussed above. This large scale analysis of a collection of essential genes permits the determination of whether there are common motifs that can be exploited in antifungal agents. The method also allows one to identify essential genes included in the same metabolic or signaling pathway, such that a number of genes or encoded proteins within a single pathway can be targeted by a combination of antifungal agents. A combination of antifungal agents directed against many targets may be more effective than an antifungal agent directed against a single target.

Although this invention is exemplified using *S. cerevisiae*, this method can be practiced using a number of other fungal genera. These include the human pathogens such as Aspergillus, Candida, Neurospora, and Trichoderma. In addition, plant pathogens such as Fusarium can be targeted as well. A large number of genes, as well as parts of some of these fungal genomes other than *S. cerevisiae*, have been cloned and methods of disrupting genes in these fungi are also known.

According to the present invention, newly identified yeast essential genes are YDR141C, YDR091C, YOL022C, YOL026C, YOL034W, and YOL077C.

5.2 Definitions and General Techniques

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, genetics and immunology. See, e.g., Maniatis et al. (1982) *Molecular Cloning, A Laboratory Manual*, 2d ed., Cold Spring Harbor Laboratory, Cold Spring Harbor, N.Y.; Sambrook et al. (1989) *Molecular Cloning. A Laboratory Manual* (Cold Spring Harbor, N.Y.: Cold Spring Harbor Laboratory Press); Ausubel et al. (1992) *Current Protocols in Molecular Biology* (New York: John Wiley & Sons); Guthrie & Fink (1991) *Methods Enzymol.* 194:1–863.

An "isolated" protein or polypeptide is one that has been separated from naturally associated components that accompany it in its native state. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art. A "protein" as used herein can be a peptide or polypeptide.

A "functional fragment" of a protein is any portion of the amino acid sequence that retains a functional activity of the protein, included but not limited to biological activity (e.g. ability to rescue a mutant in the gene encoding the protein so as to provide yeast growth or germination, immunogenicity, antigenicity, etc.)

A monomeric protein is "substantially pure," "substantially homogeneous" or "substantially purified" when at least about 60 to 75% of a sample exhibits a single polypeptide sequence. A substantially pure protein will typically comprise about 60 to 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "essential" refers to a gene that encodes a gene product whose function is required for vegetative growth or germination. An essential gene may be identified by a complete loss-of-function mutation (a knockout) of the gene which prevents yeast vegetative growth or germination on rich medium. However, a complete loss-of-function mutation is not the only way to identify an essential gene in yeast. An essential gene may also be identified by a non-null allele of the gene wherein the non-null allele encodes a protein with a sufficiently reduced biochemical activity that the protein is insufficient to meet the essential function required by the yeast, with the result that yeast vegetative growth or germination is prevented. For example, a non-null allele may be a gene having a point mutation at the active site of an enzyme. Finally, there are a number of genes in yeast that may be essential but which are duplicated in the yeast genome, such that there are multiple copies of a gene that encode proteins with the same function. Methods of identifying whether duplicate genes are essential are defined below in "Methods to Identify Essential Yeast Genes." Thus, the definition of essential genes also includes those duplicate genes in which the function of at least one copy of the duplicate gene is required for yeast vegetative growth or germination.

A *S. cerevisiae* protein has "homology" or is "homologous" to a protein from another organism if the encoded amino acid sequence of the yeast protein has a similar sequence to the encoded amino acid sequence of a protein of a different organism. Alternatively, a *S. cerevisiae* protein may have homology or be homologous to another *S. cerevisiae* protein if the two proteins have similar amino acid sequences. Although two proteins are said to be "homologous," this does not imply that there is necessarily an evolutionary relationship between the proteins. Instead, the term "homologous" is defined to mean that the two proteins have similar amino acid sequences. In addition, although in many cases proteins with similar amino acid sequences will have similar functions, the term "homologous" does not imply that the proteins must be functionally similar to each other.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al. (1994) *Methods in Molecular Biology* 24:307–31).

The following six groups each contain amino acids that are conservative substitutions for one another:
1) Alanine (A), Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Valine (V), and 6) Phenylalanine (F), Tyrosine (Y), Tryptophan (W).

Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof.

A preferred algorithm when comparing a *S. cerevisiae* sequence to a database containing a large number of sequences from different organisms is the computer program BLAST, especially blastp or tblastn (Altschul et al., 1997). Preferred parameters for blastp are:
Expectation value: 10 1 (default)
Filter: seg (default)
Cost to open a gap: 11 (default)
Cost to extend a gap: 1 (default
Max. alignments: 100 (default)
Word size: 11 (default)
No. of descriptions: 100 (default)
Penalty Matrix: BLOWSUM62

The length of polypeptide sequences compared for homology will generally be at least about 16 amino acid residues, usually at least about 20 residues, more usually at least about 24 residues, typically at least about 28 residues, and preferably more than about residues. When searching a database containing sequences from a large number of different organisms using a *S. cerevisiae* query sequence, it is preferable to compare amino acid sequences. Comparison of amino acid sequences is preferred to comparing nucleotide sequences because *S. cerevisiae* has significantly different codon usage compared to mammalian or plant codon usage.

Database searching using amino acid sequences can be measured by algorithms other than blastp known in the art. For instance, polypeptide sequences can be compared using Fasta, a program in GCG Version 6.1. Fasta provides alignments and percent sequence identity of the regions of the best overlap between the query and search sequences (Pearson (1990) *Methods in Enzymology* 183:63–98). For example, percent sequence identity between amino acid sequences can be determined using Fasta with its default parameters (a word size of 2 and the PAM250 scoring matrix), as provided in GCG Version 6.1.

The invention envisions two general types of polypeptide "homologs." Type 1 homologs are strong homologs. A comparison of two polypeptides that are Type 1 homologs would result in a blastp score of less than $1 \times 10^{-40}$, using the blastp algorithm and the parameters listed above. The lower the blastp score, that is, the closer it is to zero, the better the match between the polypeptide sequences. For instance, yeast lanosterol demethylase, which is a common target of antifungal agents, as discussed above, has a Type 1 homolog in humans. Comparison of yeast and human lanosterol demethylases produces a blastp score of $1 \times 10^{-86}$.

Type 2 homologs are weaker homologs. A comparison of two polypeptides that are Type 2 homologs would result in a blastp score of between $1 \times 10^{-40}$ and $1 \times 10^{-10}$, using the Blast algorithm and the parameters listed above. One having ordinary skill in the art will recognize that other algorithms can be used to determine weak or strong homology.

The terms "no substantial homology" or "no human (or mammalian, vertebrate, insect or plant) homolog" refers to a yeast polypeptide sequence which exhibits no substantial sequence identity with a polypeptide sequence from human, non-human mammals, other vertebrates, insects or plants. A comparison of two polypeptides which have no substantial homology to one another would result in a blastp score of greater than $1 \times 10^{-10}$, using the Blast algorithm and the parameters listed above. One having ordinary skill in the art will recognize that other algorithms can be used to determine whether two polypeptides demonstrate no substantial homology to each other.

A polypeptide "fragment," "portion" or "segment" refers to a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

A polypeptide "mutein" refers to a polypeptide whose sequence contains substitutions, insertions or deletions of one or more amino acids compared to the amino acid sequence of the native or wild type protein. A mutein has at least 50% sequence homology to the wild type protein, preferred is 60% sequence homology, more preferred is 70% sequence homology. Most preferred are muteins having 80%, 90% or 95% sequence homology to the wild type protein, in which sequence homology is measured by any common sequence analysis algorithm, such as Gap or Bestfit.

A "derivative" refers to polypeptides or fragments thereof that are substantially homologous in primary structural sequence but which include, e.g., in vivo or in vitro chemical and biochemical modifications or which incorporate unusual amino acids. Such modifications include but are not limited to, for example, acetylation, carboxylation, phosphorylation, glycosylation, ubiquitination, labeling, e.g., with radionuclides, and various enzymatic modifications, or conservative substitutions, as will be readily appreciated by those well skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled anti-ligands (e.g., antibodies), fluorophores, chemiluminescent agents, enzymes, and anti-ligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992.

The term "fusion protein" refers to polypeptides comprising polypeptides or fragments bound via a peptide bond to heterologous amino acid sequences. Fusion proteins are useful because they can be constructed to contain two or more desired functional elements from two or more different proteins. Fusion proteins can be produced recombinantly by constructing a nucleic acid sequence which encodes the polypeptide or a fragment thereof in frame with a nucleic acid sequence encoding a different protein or peptide and then expressing the fusion protein.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, or genomic sequences with which it is naturally associated. The term embraces a nucleic acid or polynucleotide that has been removed from its naturally occurring environment. The term "isolated" or "substantially pure" also can be used in reference to recombinant or cloned DNA isolates, chemically synthesized polynucleotide analogs, or polynucleotide analogs that are biologically synthesized by heterologous systems.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using Fasta, a program in GCG Version 6.1. Fasta provides alignments and percent sequence identity of the regions of the best overlap between the query and search sequences (Pearson, 1990). For instance, percent sequence identity between nucleic acid sequences can be determined using Fasta with its default parameters (a word size of 6 and the NOPAMfactor for the scoring matrix) as provided in GCG Version 6.1.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases, as measured by any well-known algorithm of sequence identity, such as Fasta, as discussed above.

Alternatively, substantial homology or similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity—preferably at least about 65%, more preferably at least about 75%, and most preferably at least about 90%—over a stretch of at least about 14 nucleotides. See, e.g., Kanehisa (1984) *Nucl. Acids Res.* 12:203–213.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., p. 9.51.

The $T_m$ for a particular DNA-DNA hybrid can be estimated by the formula:

$T_m$=81.5° C.+16.6 ($\log_{10}$[Na$^+$])+0.41 (fraction G+C)–0.63 (% formamide)–(600/l) where l is the length of the hybrid in base pairs.

The $T_m$ for a particular RNA-RNA hybrid can be estimated by the formula:

$T_m$=79.8° C.+18.5 ($\log_{10}$[Na$^+$])+0.58 (fraction G+C)+11.8 (fraction G+C)$^2$–0.35 (% formamide)–(820/l).

The $T_m$ for a particular RNA-DNA hybrid can be estimated by the formula:

$T_m$=79.8° C.+18.5($\log_{10}$[Na$^+$])+0.58 (fraction G+C)+11.8 (fraction G+C)$^2$–0.50 (% formamide)–(820/l).

In general, the $T_m$ decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated $T_m$ of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well known in the art.

An example of stringent hybridization conditions for hybridization of complementary nucleic acid sequences having more than 100 complementary residues on a filter in a Southern or Northern blot or for screening a library is 50% formamide/6× SSC at 42° C. for at least ten hours. Another example of stringent hybridization conditions is 6× SSC at 68° C. for at least ten hours. An example of low stringency hybridization conditions for hybridization of complementary nucleic acid sequences having more than 100 complementary residues on a filter in a Southern or northern blot or for screening a library is 6× SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6× SSC), or keeping the hybridization temperature and salt concentration constant (e.g. 42° C. and 6× SSC) and varying the formamide concentration from 50% to 0%. Hybridization buffers may also include blocking agents to lower background. These agents are well-known in the art. See Sambrook et al., pp. 8.46 and 9.46–9.58.

Wash conditions also can be altered to change stringency conditions. An example of stringent wash conditions is a 0.2× SSC wash at 65° C. for 15 minutes (see Sambrook et al., for SSC buffer). Often the high stringency wash is preceded by a low stringency wash to remove excess probe. An exemplary medium stringency wash for duplex DNA of more than 100 base pairs is 1× SSC at 45° C. for 15 minutes. An exemplary low stringency wash for such a duplex is 4× SSC at 40° C. for 15 minutes. In general, signal-to-noise ratio of 2× or higher than that observed for an unrelated probe in the particular hybridization assay indicates detection of a specific hybridization.

As defined herein, nucleic acids that do not hybridize to each other under stringent conditions are still substantially homologous to one another if they encode polypeptides that are substantially identical to each other. This occurs, for example, when a nucleic acid is created synthetically or recombinantly using a high codon degeneracy as permitted by the redundancy of the genetic code.

The polynucleotides of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Conservatively modified variations" of a particular nucleic acid sequence refers to nucleic acids that encode identical or essentially identical amino acid sequences or DNA sequences where no amino acid sequence is encoded. Due to the degeneracy of the genetic code, a large number of functionally identical nucleic acids encode any given polypeptide sequence. When a nucleic acid sequence is changed at one or more positions with no corresponding change in the amino acid sequence which it encodes, that mutation is called a "silent mutation." Thus, one species of a conservatively modified variation according to this invention is a silent mutation. Accordingly, every nucleic acid sequence herein which encodes a polypeptide also describes every possible silent mutation or variation.

Furthermore, one of skill in the art will recognize that individual substitutions, deletions, additions and the like, which alter, add or delete a single amino acid or a small percentage of amino acids (less than 5%, more typically less than 1%) in an encoded sequence are "conservatively modified variations" where the alterations result in the substitution of one amino acid with a chemically similar amino acid. Conservative substitution tables providing functionally similar amino acids are well known in the art.

The term "antibody" refers to a polypeptide encoded by an immunoglobulin gene, genes, or fragments thereof. The immunoglobulin genes include the kappa, lambda, alpha, gamma, delta, epsilon and mu constant regions, as well as a myriad of immunoglobulin variable regions. Light chains are classified as either kappa or lambda. Heavy chains are classified as gamma, mu, alpha, delta, or epsilon, which in turn define the immunoglobulin classes IgG, IgM, IgA, IgD and IgE, respectively.

Antibodies exist for example, as intact immunoglobulins or as a number of well-characterized fragments produced by digestion with various peptidases. For example, trypsin digests an antibody below the disulfide linkages in the hinge region to produce F(ab)'$_2$, a dimer of Fab which itself is a light chain joined to a $V_H$—$C_H$1 by a disulfide bond. The F(ab)'$_2$ may be reduced under mild conditions to break the disulfide linkage in the hinge region thereby converting the F(ab)'$_2$ dimer to a Fab' monomer. The Fab' monomer is essentially an Fab with part of the hinge region. See Paul, ed. (1993) *Fundamental Immunology*, Third Edition (New York: Raven Press), for a detailed description of epitopes, antibodies and antibody fragments. One of skill in the art recognizes that such Fab' fragments may be synthesized de novo either chemically or using recombinant DNA technology. Thus, as used herein, the term antibody includes antibody fragments produced by the modification of whole antibodies or those synthesized de novo. The term antibody also includes single-chain antibodies, which generally consist of the variable domain of a heavy chain linked to the variable domain of a light chain. The production of single-chain antibodies is well known in the art (see, e.g., U.S. Pat. No. 5,359,046). The antibodies of the present invention are optionally derived from libraries of recombinant antibodies in phage or similar vectors (see, e.g., Huse et al. (1989) *Science* 246:1275–81; Ward et al. (1989) *Nature* 341:544–46; Vaughan el al. (1996) *Nature Biotech.* 14:309–14).

As used herein, "epitope" refers to an antigenic determinant of a polypeptide, i.e., a region of a polypeptide that provokes an immunological response in a host. This region need not comprise consecutive amino acids. The term epitope is also known in the art as "antigenic determinant." An epitope may comprise as few as three amino acids in a spatial conformation which is unique to the immune system of the host. Generally, an epitope consists of at least five such amino acids, and more usually consists of at least 8–10 such amino acids. Methods for determining the spatial conformation of such amino acids are known in the art.

5.3 Methods for Constructing Mutant Yeast Strains

There are a number of methods well known in the art by which a person can disrupt a particular gene in yeast. One of skill in the art can disrupt an entire gene and create a null allele, in which no portion of the gene is expressed. One can also produce and express an allele comprising a portion of the gene which is not sufficient for gene function. This can be done by inserting a nonsense codon into the sequence of the gene such that translation of the mutant mRNA transcript ends prematurely. One can also produce and express alleles containing point mutations, individually or in combination, that reduce or abolish gene function.

There are a number of different strategies for creating conditional alleles of genes. Broadly, an allele can be conditional for function or expression. An example of an allele that is conditional for function is a temperature sensitive mutation where the gene product is functional at one temperature but non-functional at another, e.g., due to misfolding or mislocalization. One of ordinary skill in the art can produce mutant alleles which may have only one or a few altered nucleotides but which encode inactive or temperature-sensitive proteins. Temperature-sensitive mutant yeast strains express a functional protein at permissive temperatures but do not express a functional protein at non-permissive temperatures.

An example of an allele that is conditional for expression is a chimeric gene where a regulated promoter controls the expression of the gene. Under one condition the gene is expressed and under another it is not. One may replace or alter the endogenous promoter of the gene with a heterologous or altered promoter that can be activated only under certain conditions. These conditional mutants only express the gene under defined experimental conditions. All of these methods are well known in the art. For example, see Stark (1998) *Methods in Microbiology* 26:83–100; Garfinkel et al. (1998) *Methods in Microbiology* 26:101–118; and Lawrence & Rothstein (1991) *Methods in Enzymology* 194:281–301.

One having ordinary skill in the art also may decrease expression of a gene without disrupting or mutating the gene. For instance, one can decrease the expression of an essential gene by transforming yeast with an antisense molecule under the control of a regulated or constitutive promoter (see Nasr et al. (1995) *Molecular & General Genetics* 249:51–57). One can introduce an antisense construct operably linked to an inducible promoter into *S. cerevisiae* to study the function of a conditional allele (see Nasr et al. supra). One problem that may be encountered, however, is that many antisense molecules do not work well in yeast, for reasons that are, as yet, unclear (see Atkins et al. (1994) *Biological Chemistry* 375:721–29; and Olsson et al. (1997) *Applied and Environmental Microbiology* 63:2366–71).

One may also decrease gene expression by inserting a sequence by homologous recombination into or next to the gene of interest wherein the sequence targets the mRNA or the protein for degradation. For instance, one can introduce a construct that encodes ubiquitin such that a ubiquitin fusion protein is produced. This protein will be likely to have a shorter half-life than the wildtype protein. See, e.g., Johnson et al. (1992) *EMBO J.* 11:497–505.

In a preferred mode, a gene of interest is completely disrupted in order to ensure that there is no residual function of the gene. One can disrupt a gene by "classical" or PCR-based methods. The "classical" method of gene knockout is described by Rothstein, 1991. However, it is preferable to use a PCR-based deletion method because it is faster and less labor intensive.

The strategy adopted by the consortium is to utilize a one-step, polymerase chain reaction (PCR) based gene deletion method (Rothstein, 1991). Each DNA construct that is used to create the mutations are produced by two rounds of PCR (FIG. 1). All oligonucleotide synthesis and the two rounds of construct PCR (see below) are performed at a central location (Ron Davis' laboratory, Stanford University). The purified PCR products and the primers required for the analysis of the mutants are then assigned and dispersed to the various consortium members.

Gene specific UPTAG and DOWNTAG primer pairs are designed for PCR amplification of the plasmid pFA6a-KanMX4 (Wach et al. (1994) *Yeast* 10: 1793–1808). The 3' ends of the UPTAG and DOWNTAG synthetic oligonucleotides have been designed to include 18 basepairs (bp) and 19 bp, respectively, of nucleotide homology flanking the KanMX gene of the plasmid pFA6a-KanMX4 template (see FIG. 1). All of the gene specific UPTAG and DOWNTAG primer pairs contain these complementary sequences, such that the same plasmid pFA6a-KanMX4 template can be used for all of the first round PCR reactions. At their 5' ends, the UPTAG and DOWNTAG primers each have gene specific sequence homologies. The UPTAG primer contains a nucleotide sequence which includes the start codon of the gene to be knocked out and the sequence immediately upstream of the start codon. The DOWNTAG primer contains a nucleotide sequence which includes the stop codon of the gene and the sequence immediately downstream of the stop codon. For each set of primers, the sequences of the gene are derived from one of the 6000 ORFs identified in the SGD.

The UPTAG and DOWNTAG primers are then used to amplify the pFA6a-KanMX4 by PCR using conditions for PCR as described below. Hybridization conditions for specific UPTAG and DOWNTAG primers can be experimentally determined, or estimated by a number of formulas. One such formula is $T_m = 81.5 + 16.6 \, (\log_{10}[Na^+]) + 0.41$ (fraction G+C)−(600/N). See Sambrook et al. pages 11.46–11.47. The products of the first round PCR reactions are DNA molecules containing the KanMX marker (conferring resistance to the drug G-418 in *S. cerevisiae*) flanked on both ends by 18 bp of gene specific sequences (FIG. 1).

The gene specific flanking sequences are extended during the second round PCR reactions (FIG. 1). The sequences of the two gene specific PCR primers (Upstream45 and Downstream45) are derived from the 45 bp immediately upstream (including the start codon) and the 45 bp immediately downstream (including the stop codon) of each gene. Thus, following the second round of PCR the product contains the KanMX marker flanked by 45 bp of gene specific sequences corresponding to the sequences flanking the gene's ORF. The PCR products are purified by an isopropanol precipitation, and shipped with the analytical primers (see below) to the consortium members on dry ice. The precipitated PCR products are resuspended in TE buffer (10 mM Tris-HCl [pH 7.6], 1 mM EDTA).

The various mutations are constructed in two related *Saccharomyces cerevisiae* strains, BY4741 (MATα his3Δ1 leu2Δ0 met15Δ0 ura3Δ0) and BY4743 (MATa/MATαhis3Δ1/his3Δ1 leu2Δ0/leu2Δ0 LYS2/lys2Δ0 met15Δ0/MET15 ura3Δ0/ura3Δ0) (Brachmann et al. (1998) *Yeast* 14:115–32). Both of these strains are transformed with the PCR products by the lithium acetate method as described by Ito et al. (1983) *J. Bacteriol.* 153:163–68; and Schiestl & Gietz, 1989. The flanking, gene- specific yeast sequences target the integration event by homologous recombination to the desired locus (FIG. 1). Transformants are selected on rich medium (YPD) which contains G-418 (Geneticin, Life Technologies, Inc.) as described by Guthrie & Fink, 1991. Ideally, independent mutations are isolated in the haploid (BY4741) and the diploid (BY4743) strains. The heterozygous mutant diploid strain is then sporulated, and subjected to tetrad analysis (Sherman (1991) *Methods Enzymol.* 194:3–21; Sherman & Wakem (1991) *Methods Enzymol.* 194:38–57). This allows for the isolation of the mutation in MATα haploid strain. The two independently isolated MATa and MATα haploid strains are then mated to create a homozygous mutant diploid strain. Additionally, the tetrad analysis of the heterozygous mutant diploid strain allows for the identification of genes that are essential for germination and/or vegetative growth.

The molecular structure of each mutation is confirmed by a PCR strategy, utilizing four gene specific primers and two marker specific primers (FIG. 2). Two primers (A and D) flank the gene, and two primers (B and C) are within the coding region. Both recombination junctions are examined using gene specific (A/B and C/D, 5' and 3' junctions respectively) and marker specific (A/KanB and KanC/D, 5' and 3' respectively) primer pairs. A correct mutant locus fails to produce PCR products with the gene specific primers, and produces PCR products of predicted sizes with the marker specific primers. Additionally, the overall size of the locus is confirmed utilizing the flanking (A/D) primers. The resulting locus is a precise deletion of the ORF (except the start and stop codons), and the insertion of the construct PCR product containing the KanMX marker.

5.4 Methods to Identify Essential Yeast Genes

One of skill in the all will recognize that a number of methods can be used to test whether a gene is essential for vegetative growth or germination. In general, the preferred strategy depends upon the assumptions made regarding the function of the gene. For example, if one creates a conditional allele of the gene, then one can engineer a mutant strain wherein the wildtype allele has been replaced by a conditional allele. Sec, e.g., Stark (1998) *Methods in Microbiology* 26:83–100. The strain is constructed and propagated under the permissive condition, and then the strain is switched to the non-permissive (or restrictive) condition and proliferation is monitored to test whether the gene is essential for growth. This can be done in a haploid cell, or in a diploid cell as either a homozygous or heterozygous mutant.

A preferred method of testing whether a gene is essential for vegetative growth or germination is to knockout the gene completely and then analyze the knockout yeast strain by tetrad analysis. This method is preferred because one does not need to be able to engineer a conditional allele. Furthermore, as the knockout is a null allele, one is assured that it is the null phenotype that is assessed, rather than a phenotype resulting from a potentially hypomorphic conditional allele. In addition, a complete knockout of the gene can be constructed in a diploid strain where the potentially essential function of the gene is complemented by the second copy of the gene.

Once the knockout has been constructed as a heterozygous mutant, the lethality of the mutation is assessed in the haploid spores. Tetrad analysis of the haploid spores allows for the genetic characterization of a mutation because it can be determined that lethality is due to a single, nuclear mutation linked to the knockout marker (G-418 resistance).

As discussed above, an essential gene may affect either germination or vegetative growth of a yeast cell. Germination refers to a spore's reentry into the cell cycle and proliferative growth, while vegetative growth refers to the growth of the spores after germination. Tetrad analysis can be used to determine the effects of a knockout gene on either germination or vegetative growth. Tetrad dissection is the most direct way to assess germination because one can immediately and visually determine (microscopically) whether a yeast spore has germinated, or, if it has germinated, whether it has proliferated. If a gene is essential either for vegetative growth or germination, those spores containing the knockout allele will not proliferate, while those containing the wildtype allele will grow normally.

One of ordinary skill in the art will recognize that whether a gene is characterized as essential is dependent in part upon the conditions under which tetrad analysis is performed. The choice of growth medium and growing conditions may influence the effect of the knockout on vegetative growth and germination. For instance, asci dissection and growth performed on minimal medium may produce a greater number of essential genes compared to asci dissection and growth performed on rich medium. Temperature will also affect the determination of essential genes. One having ordinary skill in the art will be able to determine what growth parameters are important for their particular use. Preferably, tetrad analysis is performed on a rich growth medium at 30° C. in order to minimize the number of genes that are essential only in medium that contains limited amounts of nutrients and under normal growth conditions.

Approximately 20% of the *S. cerevisiae* genome is duplicated. Therefore, there are a number of essential cellular functions that are encoded by two or more copies of the gene. For example, the genes RAS1 and RAS2 are highly homologous and encode GTP-binding proteins involved in the regulation of the essential cAMP pathway. Due to the overlapping functions of these two genes, a RAS1 mutation is not lethal in a wildtype background but is lethal in a RAS2 background (Toda et al. (1987) *Cell* 50:277–87). With the complete genomic sequence of *S. cerevisiae* known, it has been possible to compile all of the duplicated genes. Thus, it may be necessary to construct multiple mutations in order to assess which of the duplicated genes encode essential functions. This can be easily achieved by crossing the MATα haploid of one mutant to the MATα haploid of another mutant to create a double heterozygous diploid. Tetrad analysis can then be performed to determine if the double mutation is lethal. Further multiple mutations (i.e., triple, quadruple, etc.) can be created and assessed in an analogous manner.

If a gene is determined to be essential for the vegetative growth and/or germination of *S. cerevisiae*, further analysis can be performed to characterize the lethal phenotype. The dead spores can be examined microscopically to determine if any cell division had occurred. If the spore fails to divide even once, it would suggest that the gene product is required for germination. This can be addressed further by constructing a conditional allele of the gene, which allows for a separate assessment of the gene's involvement in vegetative growth and germination. If a spore divides a number of times before ceasing growth, it would indicate that the spore is able to germinate and that the gene is required for vegetative growth but not for germination. The cellular morphology can be examined further to determine if the cells are arrested at a specific point of the cell cycle (Lew et oil. (1997) "Cell Cycle Control in *Saccharomyces cerevisiae*," in *The Molecular and Cellular Biology of the Yeast Saccharomyces*, J. R. Pringle, J. R. Broach and E. W. Jones, eds. (Cold Spring Harbor, N.Y.: Cold Spring Harbor Laboratory Press), pp. 607–696). A specific cell cycle arrest may provide some insights into the function of the gene product.

Another method for characterizing the essential gene is to determine whether the heterozygous diploid has a slow growth phenotype compared to the wildtype strain. In general, the heterozygous diploid will have only half of the amount of the essential gene product compared to the wildtype strain. Therefore, if the heterozygous diploid grows more slowly than the wildtype strain, it is likely that the quantity of the essential gene product is limiting for cell proliferation in the heterozygous diploid. If this is the case, it may indicate that it is not necessary to inhibit completely the function of the gene product to give rise to an impaired phenotype. This information is useful because it provides information about whether an antifungal agent would have to inhibit the gene completely to be effective, or whether only a decrease in the gene's activity would be required.

In order to characterize whether the heterozygous diploid has a slow growth phenotype, a co-culture experiment with the wildtype strain may be performed. During the course of co-culturing the two strains, samples are removed and the relative amounts of the two strains in the culture are determined. This can be achieved simply by plating a calculated dilution of the culture on rich media, counting the total number of cells, and then replica-plating the cells on selective media plates. In the case where the essential gene is disrupted using, the KanMX marker, one can use YPD-G-418 plates to determine the fraction of these cells that are heterozygous diploids. If, after co-culturing, the heterozygous diploids are present as a smaller fraction of cells than the fraction they represented before co-culturing, then the heterozygous diploids exhibit a slow growth phenotype. Time courses of co-cultured strains may be done in order to provide more precise estimates of relative growth proficiencies.

Some fungal species are pathogenic only in the pseudohyphal or hyphal phase. For such species, genes can be assessed for their requirement for pseudohyphal or hyphal growth. For instance, *S. cerevisiae* genes required for pseudohyphal growth can be identified by growing the mutants on the appropriate medium which promotes pseudohyphal growth (i.e., a low nitrogen medium).

5.5 Methods to Identify Potential Homologs in Other Organisms

Once a gene has been mutated and shown to be essential for vegetative growth or germination, one can determine whether the essential gene from yeast has homologs in other organisms, such as lumans, non-human mammals, other vertebrates such as fish, insects, plants, or other fungi.

One method of determining whether an essential *S. cerevisiae* gene has homologs is by the use of low stringency hybridization and washing. In general, genome DNA or cDNA libraries can be screened using probes derived from the essential *S. cerevisiae* gene using methods known in the art. See above and pp. 8.46–8.49 and 9.46–9.58 of Sambrook et al., 1989. Preferably, genomic DNA libraries are screened because cDNA libraries generally will not contain all the mRNA species an organism can make. Genomic DNA libraries from a variety of different organisms, such as plants, fungi, insects, and various mammalian species are commercially available and can be screened. This method is useful for determining whether there are homologs in organisms whose DNA sequences have not been characterized extensively.

A second method of determining whether an essential *S. cerevisiae* gene has homologs is through the use of degenerate PCR. In this method, degenerate oligonucleotides that encode short amino acid sequences of the essential *S. cerevisiae* gene are made. Methods of preparing degenerate oligonucleotides and using them in PCR to isolate uncloned genes are well known in the art (see Sambrook et al., 1989, pp. 14.7–14.8).

The most preferred method is to compare the sequence of the *S. cerevisiae* gene to sequences from other organism. Either the nucleotide sequence of the essential gene or its encoded amino acid sequence is compared to the sequences from other organisms. Preferably, the encoded amino acid sequence of the essential gene is compared to amino acid sequences from other organisms. The sequence of the essential gene can be compared by a number of different algorithms well known in the art (see definitions section). In general, computer programs designed for sequence analysis are used for the purpose of comparing the sequence of interest to a large database of other sequences. Any computer program designed for the purpose of sequence comparison can be used in this method. Some computer programs, such as Fasta, produce results that are typically presented as "% sequence identity." Other computer programs, such as blastp, produce results presented as "p-values." Preferably, the essential gene sequence will be compared to other sequences using the blastp algorithm.

Nucleotide and amino acid sequences of essential genes may be compared to vertebrate sequences, including human and non-human mammalian sequences, as well as plant and insect sequences using any one of the large number of programs known in the art for comparing nucleotide and amino acid sequences to sequences in a database. Examples of such programs are Fasta and blastp, discussed above. Examples of databases which can be searched include GenBank-EMBL, SwissProt, DDBJ, GeneSeq, and EST databases, as well as databases containing combinations of these databases.

The invention envisions that, regardless of how the homolog is first identified, the blastp algorithm or functional equivalent or improvement thereof, will be used to determine the "p-value" for the amino acid sequence encoded by an essential yeast gene and the amino acid sequence of its homolog. The invention envisions that the homolog will fall into one of three groups based upon its level of sequence identity to genes from other organisms. One group are those proteins wherein the sequence encoded by essential yeast genes exhibits no substantial homology to a protein sequence from the organism of interest. For instance, if a human antifungal agent is desired, the essential fungal gene or encoded protein target exhibits no substantial homology to any known gene or EST, or to any encoded protein from a gene from human. If a plant antifungal agent is desired, the essential fungal gene or encoded protein target exhibits no significant homology to any known gene, EST, or encoded protein from a plant. Conversely, if an herbicide or insecticide is desired, the essential fungal gene target preferably will exhibit strong (Type 1) or weak (Type 2) homology to a plant or insect protein. Similarly, if an anti-proliferative drug is desired, the essential fungal gene target preferably will exhibit strong (Type 1) homology, or less desirably weak (Type 2) homology, to a human or mammalian protein.

Essential yeast genes may encode potential antifungal targets even when there is homology with an amino acid sequence of a protein from a desired host. Preferably, the yeast gene exhibits a limited degree of homology with the amino acid sequence of a protein from a desired host. Members of this group would be considered a weak homolog (Type 2). For instance, the polypeptide of the essential yeast gene could show a low level of sequence identity or homology over the entire length of the host protein. Alternatively, the encoded yeast protein could exhibit substantial homology or sequence identity over small region(s) with the protein from a desired host. A third group of potential antifungal targets encompasses essential yeast genes which exhibit substantial homology (Type 1 homologs) with polypeptides from a desired host. This group is less preferred as antifungal targets than genes which encode proteins with no homology or with limited homology. However, even minor differences between the essential gene or its encoded protein and the homologous gene or its encoded protein in the desired host can be exploited using the essential yeast gene target to produce antifungal agents by the methods described below.

As a further characterization of the yeast essential gene (see above), any potential homologs from other organisms can be assessed for their ability to functionally complement the yeast mutant. This can be achieved by first cloning the homolog into a *S. cerevisiae* expression vector by standard methods. This plasmid can then be transformed into the heterozygous mutant diploid strain. Upon sporulation and tetrad dissection the ability of the homolog to complement the yeast function is determined by whether or not the haploid spores harboring the knockout mutation are able to grow. The ability of the homolog to complement the yeast mutant would indicate shared function(s) and suggest that the homolog may also be essential in the original organism.

5.6 Nucleic Acids, Vectors and Production of Recombinant Polypeptides

The present invention provides nucleic acids and recombinant DNA vectors which comprise *S. cerevisiae* essential gene DNA sequences. Specifically, vectors comprising all or portions of the DNA sequence of YDR141C, YDR091C, YOL022C, YOL026C, YOL034W, and YOL077C are provided. The vectors of this invention also include those comprising DNA sequences which hybridize under stringent conditions to the YDR141C, YDR091C, YOL022C, YOL026C, YOL034W, and YOL077C gene sequences, and conservatively modified variations thereof.

The nucleic acids of this invention include single-stranded and double-stranded DNA, RNA, oligonucleotides, anti-sense molecules, or hybrids thereof and may be isolated from biological sources or synthesized chemically or by recombinant DNA methodology. The nucleic acids, recombinant DNA molecules and vectors of this invention may be present in transformed or transfected cells, cell lysates, or in partially purified or substantially pure forms.

DNA sequences may be expressed by operatively linking them to an expression control sequence in an appropriate expression vector and employing that expression vector to transform an appropriate unicellular host. Expression control sequences are sequences which control the transcription, post-transcriptional events and translation of DNA sequences. Such operative linking of a DNA sequence of this invention to an expression control sequence, of course, includes, if not already part of the DNA sequence, the provision of a translation initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences.

Useful expression vectors for bacterial hosts include bacterial plasmids, such as those from *E. coli,* including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGTh10 and λGT11, and other phages, e.g., M13 and filamentous single stranded phage DNA. In yeast, vectors include Yeast Integrating plasmids (e.g., YIp5) and Yeast Replicating plasmids (the YRp and YEp series plasmids), Yeast centromere plasmids (the YCp series plasmids), pGPD-2, 2μ plasmids and derivatives thereof, and improved shuttle vectors such as those described in Gietz & Sugino (1988) *Gene* 74:527–34 (YIplac, YEplac and YCplac). Expression in mammalian cells can be achieved using a variety of plasmids, including pSV2, pBC12BI, and p91023, as well as lytic vinis vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL941.

In addition, any of a wide variety of expression control sequences—sequences that control the expression of a DNA sequence when operatively linked to it—may be used in these vectors to express the DNA sequences of this invention. Such useful expression control sequences include the expression control sequences associated with structural genes of the foregoing expression vectors. Expression control sequences that control transcription include, e.g., promoters, enhancers and transcription termination sites. Expression control sequences that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct expression of the polypeptide to particular cellular compartments, and sequences in the 5' and 3' untranslated regions that modify the rate or efficiency of translation.

Examples of useful expression control sequences include, for example, the early and late promoters of SV40 or adenovirus, the lac system, the trp system, the TAC or TRC system, the T3 and T7 promoters, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system, the GAL1 or GAL10 promoters, and other constitutive and inducible promoter sequences known to control the expression of genes of prokaryotic or eukaryotic cells or their viruses, and various combinations thereof. See, e.g., *The Molecular Biology of the Yeast Saccharomyces* (eds. Strathern, Jones and Broach) Cold Spring Harbor Lab., Cold Spring Harbor, N.Y. for details on yeast molecular biology in general and on yeast expression systems (pp. 181–209).

DNA vector design for transfection into mammalian cells should include appropriate sequences to promote expression of the gene of interest, including: appropriate transcription initiation, termination and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A great number of expression control sequences—constitutive, inducible and/or tissue-specific—are known in the art and may be utilized. For eukaryotic cells, expression control sequences typically include a promoter, an enhancer derived from immunoglobulin genes, SV40, cytomegalovirus, etc., and a polyadenylation sequence which may include splice donor and acceptor sites. Substantial progress in the development of mammalian cell expression systems has been made in the last decade and many aspects of the system are well characterized.

Preferred DNA vectors also include a marker gene and means for amplifying the copy number of the gene of interest. DNA vectors may also comprise stabilizing sequences (e.g., orl- or ARS-like sequences and telomere-like sequences), or may alternatively be designed to favor directed or non-directed integration into the host cell genome. In a preferred embodiment, DNA sequences of this invention are inserted in frame into an expression vector that allows high level expression of an RNA which encodes a fusion protein comprising encoded DNA sequence of interest.

Of course, not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered.

In selecting an expression control sequence, a variety of factors should also be considered. These include, for example, the relative strength of the sequence, its controllability, and its compatibility with the DNA sequence of this invention, particularly with regard to potential secondary structures. Unicellular hosts should be selected by consideration of their compatibility with the chosen vector, the toxicity of the product coded for by the DNA sequences of this invention, their secretion characteristics, their ability to fold the polypeptide correctly, their fermentation or culture requirements, and the ease of purification from them of the products coded for by the DNA sequences of this invention.

Within these parameters, one of skill in the art may select various vector/expression control sequence/host combinations that will express the DNA sequences of this invention in fermentation or in other large scale cultures.

Given the strategies described herein, one of skill in the art can construct a variety of vectors and nucleic acid molecules comprising functionally equivalent nucleic acids. DNA cloning and sequencing methods are well known to those of skill in the art and are described in an assortment of laboratory manuals, including Sambrook et al., 1989; and Ausubel et al., 1994 Supplement. Product information from manufacturers of biological, chemical and immunological reagents also provide useful information.

The recombinant DNA molecules and more particularly, the expression vectors of this invention may be used to express the essential genes from *S. cerevisiae* as recombinant polypeptides in a heterologous host cell. The polypeptides of this invention may be full-length or less than full-length polypeptide fragments recombinantly expressed from the DNA sequences according to this invention. Such polypeptides include variants and muteins having biological activity. The polypeptides of this invention may be soluble, or may be engineered to be membrane- or substrate-bound using techniques well known in the art.

Particular details of the transfection, expression and purification of recombinant proteins are well documented and are understood by those of skill in the art. Further details on the various technical aspects of each of the steps used in recombinant production of foreign genes in mammalian cell expression systems can be found in a number of texts and laboratory manuals in the art. See, e.g., Ausubel et al., 1989.

Transformation and other methods of introducing nucleic acids into a host cell (e.g., transfection, electroporation, liposome delivery, membrane fusion techniques, high velocity DNA-coated pellets, viral infection and protoplast fusion) can be accomplished by a variety of methods which are well known in the art (see, for instance, Austibel, supra, and Sambrook, supra). Bacterial, yeast, plant or mammalian cells are transformed or transfected with an expression vector, such as a plasmid, a cosmid, or the like, wherein the expression vector comprises the DNA of interest. Alternatively, the cells may be infected by a viral expression vector comprising the DNA or RNA of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

A wide variety of unicellular host cells are useful in expressing the DNA sequences of this invention. These hosts may include well known eukaryotic and prokaryotic hosts, such as strains of *E. coli,* Pseudomonas, Bacillus, Streptomyces, fungi, yeast, insect cells such as *Spodoptera frugiperda* (SF9), animal cells such as CHO, BHK, MDCK and various murine cells, e.g., 3T3 and WEHI cells, African green monkey cells such as COS 1, COS 7, BSC 1, BSC 40, and BMT 10, and human cells such as VERO, WI38, and HeLa cells, as well as plant cells in tissue culture.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or cleavage of a signal sequence to produce a "mature" protein. Accordingly, the polypeptide expression products of this invention encompass full-length polypeptides and modifications or derivatives thereof, such as glycosylated versions of such polypeptides, mature proteins and polypeptides retaining a signal peptide. The present invention also provides for biologically active fragments of the polypeptides. Sequence analysis or genetic manipulation may identify those domains responsible for the essential function of the protein in yeast. Thus, the invention encompasses the production of biologically active fragments that can be used as antifungal targets. The invention also encompasses fragments of the polypeptides which would be valuable as antigens for the production of antibodies, or as competitors for antibody binding.

The polypeptides of this invention may be fused to other molecules, such as genetic, enzymatic or chemical or immunological markers such as epitope tags. Fusion partners include, inter alia, myc, hemagglutinin (HA), GST, immunoglobulins, β-galactosidase, biotin trpE, protein A, β-lactamase, a amylase, maltose binding protein, alcohol dehydrogenase, polyhistidine (for example, six histidine at the amino and/or carboxyl terminus of the polypeptide), lacZ, green fluorescent protein (GFP), yeast α mating factor, GAL4 transcription activation or DNA binding domain, luciferase, and serum proteins such as ovalbumin, albumin and the constant domain of IgG. See, e.g., Godowski et al. (1988) *Science* 241(4867):812–6; and Ausubel et al., supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques such as those described in Merrifield, et al. (1965) *Nature* 207(996):522–3, or produced by chemical cross-linking.

Tagged fusion proteins permit easy localization, screening and specific binding via the epitope or enzyme tag. See Ausubel et al., 1991, Chapter 16. Some tags allow the protein of interest to be displayed on the surface of a phagemid, such as M13, which is useful for panning agents that may bind to the desired protein targets. Thus, fusion proteins are useful for screening potential antifungal agents, insecticides, herbicides or anti-proliferation drugs using the protein targets encoded by the essential genes.

One advantage of fusion proteins is that an epitope or enzyme tag can simplify purification. These fusion proteins may be purified, often in a single step, by affinity chromatography. For example, a $His^6$ tagged protein can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. A second advantage of fusion proteins is that the epitope tag can be used to bind the fusion protein to a plate or column through an affinity linkage for screening targets.

In addition, fusion proteins comprising the constant domain of IgG or other serum proteins can increase a protein's half-life in circulation for use therapeutically.

Fusion proteins comprising a targeting domain can be used to direct the protein to a particular cellular compartment or tissue target in order to increase the efficacy of the functional domain. See, e.g., U.S. Pat. No. 5,668,255, which discloses a fusion protein containing a domain which binds to an animal cell coupled to a translocation domain of a toxin protein. Fusion proteins may also be useful for improving antigenicity of a protein target. Examples of making and using fusion proteins are found in U.S. Pat. Nos. 5,225,538, 5,821,047, and 5,783,398.

5.7 Production of Polypeptide Fragments, Derivatives and Muteins and Biological Assays Thereof Fragments, derivatives and muteins of polypeptides encoded by essential genes can be produced recombinantly or chemically, as discussed above. One can produce fragments of a polypeptide encoding an essential gene by truncating the DNA encoding the essential gene and then expressing it recombinantly. Alternatively, one can produce a fragment by chemically synthesizing a portion of the full-length polypeptide. One may also produce a fragment by enzymatically cleaving the polypeptide. Methods of producing polypeptide fragments are well-known in the art (see, e.g., Sambrook et al. and Ausubel et al., supra). Molecules comprising a protein or fragment can also be made by cross-linking the protein or fragment to another chemical structure.

One may produce muteins of a polypeptide encoded by an essential gene by introducing mutations into the DNA sequence of the essential gene and then expressing it recombinantly. These mutations may be targeted, in which particular encoded amino acids are altered, or may be untargeted, in which random encoded amino acids within the polypeptide are altered. Muteins with random amino acid alterations can be screened for a particular biological activity. Methods of producing muteins with targeted or random amino acid alterations are well known in the art, see e.g., Sambrook et al. and Ausubel et al., supra, and U.S. Pat. No. 5,223,408. Production of polypeptide derivatives are well known in the art, see above.

There are a number of methods known in the art to determine whether fragments, muteins and derivatives of polypeptides encoded by essential genes have the same, enhanced or decreased biological activity as the wild type polypeptides. One of the simplest assays involves determining whether the fragment, mutein or derivative can complement the essential gene in a cell which does not contain the essential gene. For instance, one can introduce a DNA encoding a fragment or mutein of a polypeptide encoded by an essential gene into a mutant yeast strain which has the essential gene of interest deleted (see above under "Methods of Producing Mutant Yeast Strains"). If introduction of the DNA encoding the fragment or mutein permits the mutant yeast strain to grow, then the fragment or mutein is biologically active, and complements the deleted gene. One can determine whether the fragment or mutein is more or less active than the wild type polypeptide by co-culturing yeast cells containing the fragment or mutein and yeast cells containing the wild type gene and determining whether the wildtype polypeptide or fragment or mutein is more effective in promoting growth (see above under "Methods to Identify Essential Yeast Genes"). In cases in which there is an essential gene homologous to the essential yeast gene in another organism, this type of complementation analysis of muteins and fragments may be called out either in yeast cells or in cells from the other organism provided that the essential gene in the cells is knocked out.

Screens may be performed to identify those genes and gene products that interact, either genetically or physically, with the essential gene in question. One may construct a yeast strain which has an essential gene that is non-functional (i.e., the gene is knocked-out or has a mutation that renders the gene product inactive), but which also contains a complementing plasmid bearing the essential gene. An expression library can be screened for clones that, when expressed in this type of yeast strain, allows the loss of the complementing plasmid bearing the essential gene (multi-copy suppression). Alternatively, a mutant screen can be performed in this type of yeast strain to identify second site mutations that allow the loss of the complementing plasmid bearing the essential gene in a strain with the knock-out mutation (synthetic viability).

In another type of screening assay, the essential gene or a fragment thereof can be used as the "bait" in a two-hybrid screen to identify molecules that physically interact with the essential gene. See Chien et al. (1991) *Proc. Natl. Acad. Sci. U.S.A.* 88(21):9578–82.

In addition, one may generate genome expression profiles of yeast strains to characterize the essential gene's function. In order to generate such profiles, a conditional allele of the essential gene in a yeast strain must be produced. The conditional allele may be constructed by any technique known in the art, including making a temperature-sensitive allele of the essential gene or operably linking the essential gene to an inducible promoter for regulated expression. The yeast strain containing the conditional allele is first grown under the permissive condition, allowing expression of the functional product of the essential gene, to permit the growth of the yeast strain for the assay. Then, the yeast strain is shifted to the nonpermissive condition, in which the product of the essential gene is not made or is non-functional. The genome expression profile of the yeast strain under the nonpermissive condition may be measured using, for example, hybridization chips, and the expression profile compared to known standards, e.g., the same yeast strain grown under permissive conditions or a wildtype yeast strain. Structure-function studies can be performed wherein a library of mutant forms of the gene is screened for the ability to complement the knock-out mutant strain.

Fragments, muteins and derivatives may also be microinjected into a mutant yeast strain in which the essential gene of interest is deleted to determine whether the introduction of the fragment, mutein or derivative can complement the genetic defect. Similarly, fragments, muteins and derivatives may be microinjected into other cell types in which the homologous gene has been deleted.

Finally, if a particular biochemical activity of a polypeptide encoded by an essential gene is known, this activity can be measured for fragments, muteins or derivatives of the polypeptide. For instance, if an essential gene encodes a kinase, one could measure the kinase activity of the wild type polypeptide and compare it to the activity of a fragment, mutein or derivative.

5.8 Production of Antibodies

The polypeptides encoded by the essential genes of this invention may be used to elicit polyclonal or monoclonal antibodies which bind to the essential gene product or a homolog from another species using a variety of techniques well known to those of skill in the art. Alternatively, peptides corresponding to specific regions of the polypeptide encoded by the essential gene may be synthesized and used to create immunological reagents according to well known methods.

Antibodies directed against the polypeptides of this invention are immunoglobulin molecules or portions thereof that are immunologically reactive with the polypeptide of the present invention. It should be understood that the antibodies of this invention include antibodies immunologically reactive with fusion proteins.

Antibodies directed against a polypeptide encoded by an essential gene may be generated by immunization of a mammalian host. Such antibodies may be polyclonal or monoclonal. Preferably they are monoclonal. Methods to produce polyclonal and monoclonal antibodies are well known to those of skill in the art. For a review of such methods, see Harlow & Lane (1988) *Antibodies, A Laboratory Manual;* Yelton et al. (1981) *Ann. Rev. of Biochem.* 50:657–80; and Ausubel et al., 1989. Determination of immunoreactivity with a polypeptide encoded by an essential gene may be made by any of several methods well known in the art, including by immunoblot assay and ELISA.

Monoclonal antibodies with affinities of $10^{-8}$ $M^{-1}$ or preferably $10^{-9}$ to $10^{-10}$ $M^{-1}$ or stronger are typically made by standard procedures as described, e.g., in Harlow & Lane, 1988. Briefly, appropriate animals are selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989, *Science* 246:1275–81. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

An antibody of this invention may also be a hybrid molecule formed from immunoglobulin sequences from different species (e.g., mouse and human) or from portions of immunoglobulin light and heavy chain sequences from the same species. An antibody may be a single-chain antibody or a humanized antibody. It may be a molecule that has multiple binding specificities, such as a bifunctional antibody prepared by any one of a number of techniques known to those of skill in the art including the production of hybrid hybridomas, disulfide exchange, chemical cross-linking, addition of peptide linkers between two monoclonal antibodies, the introduction of two sets of immunoglobulin heavy and light chains into a particular cell line, and so forth.

The antibodies of this invention may also be human monoclonal antibodies, for example those produced by immortalized human cells, by SCID-hu mice or other non-human animals capable of producing "human" antibodies, or by the expression of cloned human immunoglobulin genes. The preparation of humanized antibodies is taught by U.S. Pat. Nos. 5,777,085 and 5,789,554.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

5.9 Therapeutic Methods Using Nucleic Acids Encoding Essential Genes

Once a gene has been identified as essential in *S. cerevisiae*, the gene and its nucleotide sequence can be exploited in a number of ways so that the essential gene can be used as an antifungal target. One method is to use the primary sequence of the essential gene itself. For instance, antisense oligonucleotides can be produced which are complementary to the mRNA of the essential gene. Antisense oligonucleotides can be used to inhibit transcription or translation of an essential yeast gene. Production of antisense oligonucleotides effective for therapeutic use is well-known in the art, see Agrawal et al. (1997) *Pharmacology & Therpaeutics* 76:151–60; Lavrovsky et al. (1997) *Biochemical and Molecular Medicine* 62:11–22; and Crooke (1998) *Biotechnology and Genetic Engineering Reviews* 15:121–57. Antisense oligonucleotides are often produced using derivatized or modified nucleotides in order to increase half-life or bioavailability.

The primary sequence of the essential gene can also be used to design ribozymes that can target and cleave specific essential gene sequences. There are a number of different types of ribozymes. Most synthetic ribozymes are generally hammerhead, Tetrahymena and hairpin ribozymes. Methods of designing and using ribozymes to cleave specific RNA species are known in the art, see Zhao et al. (1998) *Mol. Cell. Neurosci.* 11:92–97; Lavrovsky et al. (1997); and Eckstein (1997) *Ciba Foundation Symposium* 207–17. Although hammerhead ribozymes are generally ineffective in yeast (Castanotto et al. (1998) *Antisense & Nucleic Acid Drug Development* 8:1–13), other types of ribozymes may be effective as antifungal agents.

As discussed above, one can use essential yeast genes to identify genes critical for growth in insects, plants, humans and other mammals. Therefore, one can design ribozymes and antisense molecules to these genes in insects and plants for use as insecticides and herbicides, respectively. Similarly, one can design ribozymes and antisense molecules to genes important to proliferation in humans or other mammals for use as anti-proliferation drugs.

5.10 Methods Using Neutralizing Antibodies to Proteins Encoded by Essential Genes The protein encoded by the essential gene can be used to elicit neutralizing antibodies for use as antifungal inhibitors, insecticides, herbicides or for anti-proliferation drugs. An antibody may be an especially good antifungal inhibitor, insecticide, herbicide or anti-proliferation drug if the gene of interest encodes a protein which is expressed on the cell surface, such as an integral membrane protein. Although polyclonal antibodies may be made, monoclonal antibodies are preferred. Monoclonal antibodies can be screened individually in order to isolate those that are neutralizing or inhibitory for the protein encoded by the essential gene. Monoclonal antibodies also may be screened for inhibition of a particular function of a protein. For instance, if it is known that the essential gene in yeast encodes a protein kinase, one can identify antibodies that inhibit kinase activity. Alternatively, if the specific function of an essential gene is unknown, one can measure inhibition of yeast proliferation using panels of antibodies. Similarly, one can screen antibodies which are directed against insect, plant or human proteins for inhibition of a particular activity or for inhibition of proliferation of appropriate cells.

Monoclonal antibodies which inhibit yeast growth in vitro may be humanized for therapeutic use using methods well-known in the art, see, e.g., U.S. Pat. Nos. 5,777,085 and 5,789,554. Monoclonal antibodies may also be engineered as single-chain antibodies using methods well-known in the art for therapeutic use, see, e.g., U.S. Pat. Nos. 5,091,513, 5,587,418, and 5,608,039.

Neutralizing antibodies may also be used diagnostically. For instance, the binding site of a neutralizing antibody to the protein encoded by the essential gene can be used to help identify domains that are required for the protein's activity. The information about the critical domains of an essential protein can be used to design inhibitors that bind to the critical domains of the essential protein. In addition, neutralizing antibodies can be used to validate whether a potential inhibitor of an essential protein inhibits the protein in in vitro assays.

5.11 Methods of Using Essential Genes to Identify Targets

Once an essential gene in yeast is identified, the Genome Reporter Matrix (see U.S. Pat. Nos. 5,569,588 and 5,777,888) can be used to identify critical functional attributes of the gene. The Genome Reporter Matrix is a library of yeast that contains several thousand yeast strains each of which contains a single gene fusion of a yeast gene to a reporter gene. Thus, each gene of the yeast genome is "tagged" by a reporter gene, and its transcription in response to a particular stimulus can be measured. In order to determine the particular transcripts an essential yeast gene modifies, one overexpresses the essential gene in the cells of the Genome Reporter Matrix. One may also express a conditional allele of the gene in the cells of the Genome Reporter Matrix. One may also express a conditional allele gene in the cells of the Genome Reporter Matrix and measure the response under the non- or semi-permissive condition. Then, one identifies a subset of genes that are either induced or repressed by overexpression of the essential gene. Methods for processing data using the Genome Reporter Matrix are also disclosed in U.S. Pat. Nos. 5,569,588 and 5,777,888. Once the genes that are regulated by an essential gene are identified, one can use this information in a number of ways to identify antifungal compounds. One may be able to ascertain what particular metabolic or signaling pathway an essential gene is part of. This knowledge may allow one to narrow the focus of a search for compounds that will target the essential gene. Alternatively, one may use the subset of cells expressing the regulated genes for screening potential antifungal compounds. For instance, if overexpression of the essential gene leads to an upregulation of particular genes, potential antifungal agents could be screened by looking for down-regulation of those genes. Conversely, if overexpression of the essential gene leads to downregulation of particular genes, antifungal agents could be screened by looking for upregulation of those genes.

Another method for isolating a potential antifungal agent of an essential gene target is to use information obtained from the "two-hybrid system" to identify and clone genes encoding proteins that interact with the polypeptide target encoded by the essential gene (see, e.g., Chien et al., 1991, Proc. Natl. Acad. Sci. U.S.A. 88(21):9578–82). The amino acid sequences of the polypeptides identified by the two-hybrid system can be used to design inhibitory peptides to the essential gene. Furthermore, the method may also identify other genes that are essential in yeast that may be good potential antifungal targets as well.

In a similar fashion, both the Genome Reporter Matrix system and the "two-hybrid system" can be used to identify genes in other organisms that may be amenable to regulation by compounds for use as insecticides, herbicides and anti-proliferation drugs.

For instance, one can overexpress a homologous insect gene in an insect Genome Reporter Matrix system and identify genes that are regulated by the insect gene. One can then screen compounds that upregulate or downregulate these regulated genes in order to identify potential insecticides. Similar plant and human Genome Reporter Matrix systems overexpressing essential or critical genes can be used in the same way to identify herbicides and anti-proliferative agents, respectively. The "two-hybrid" system using libraries of the appropriate species can also be used to identify insecticides, herbicides and/or anti-proliferative agents.

Other methods for identifying targets of genes and assaying up-regulation and/or down-regulation of genes may also be used (see, e.g., PCT publications WO 98/38329 dated Sep. 3, 1998 and WO 97/10365 dated Mar. 20, 1997).

5.12 Methods of Using Protein Targets

Recombinantly expressed purified proteins can be used to screen libraries of natural, semisynthetic or synthetic compounds. Particularly useful types of libraries include combinatorial small organic molecule libraries, phage display libraries, and combinatorial peptide libraries. Methods of determining whether components of the library bind to a particular polypeptide are well known in the art. In general, the polypeptide target is attached to solid support surface by non-specific or specific binding. Specific binding can be accomplished using an antibody which recognizes the protein that is bound to a solid support, such as a plate or column. Alternatively, specific binding may be through an epitope tag, such as GST binding to a glutathione-coated solid support, or IgG fusion protein binding to a Protein A solid support. Alternatively, the recombinantly expressed protein or fragments thereof may be expressed on the surface of phage, such as M13. A library in mobile phase is incubated under conditions to promote specific binding between the target and a compound. Compounds which bind to the target can then be identified. Alternately, the library is attached to a solid support and the polypeptide target is in the mobile phase.

Binding between a compound and target can be determined by a number of methods. The binding can be identified by such techniques as competitive ELISAs or RIAs, for example, wherein the binding of a compound to a target will prevent an antibody to the target from binding. These methods are well-known in the art, see, e.g., Harlow and Lane, supra. Another method is to use BiaCORE (BiaCORE) to measure interactions between a target and a compound using methods provided by the manufacturer. A preferred method is automated high throughput screening, see, e.g., Burbaum et al. (1997) Current Opinion in Chemical Biology 1:72–8; and Schullek et al. (1997) Analytical Biochemistry 246:20–29.

Once a compound that binds to a target is identified, one then determines whether the compound inhibits the activity of the target. For a compound that binds to a antifungal target, one can measure inhibition of proliferation or germination in yeast incubated with the potential antifungal compound. For a potential insecticide or herbicide, one can measure inhibition of proliferation of insect or plant cells, respectively. Alternatively, for a potential anti-proliferative drug, one could measure inhibition of proliferation of a mammalian cell after incubation with the potential anti-proliferative drug. If a biological function for the target protein is known, one could determine whether the compound inhibited the biological activity of the protein. For instance, if it is known that the target protein is a kinase, one can measure the inhibition of kinase activity in the presence of the potential inhibitor.

Another embodiment of the invention is to use the recombinantly expressed protein for rational drug design. The structure of the recombinant protein may be determined using x-ray crystallography or nuclear magnetic resonance (NMR). Alternatively, one could use computer modeling to determine the structure of the protein. The structure can be used in rational drug design to design potential inhibitory compounds of the target (see, e.g., Clackson (1998) *Curr. Opin. Struct. Biol.* 8:451–8; Mattos et al. (1996) *Nature Biotechnol.* 14:595–9; Hubbard (1997) *Curr. Opin. Biotechnol.* 8:696–700; Cunningham et al. (1997) *Curr. Opin. Struct. Biol.* 7:457–62; Kubinyi (1995) *Pharmazie* 50:647–62; Kleinberg et al. (1995) *Am. J. Health Syst. Pharm.* 52:1323–36.). Potential antifungal inhibitors can then be tested for inhibition of proliferation or germination in yeast, while potential anti-proliferative compounds can be tested for inhibition of mammalian, preferably human, cells. Similarly, potential herbicidal and insecticidal compounds can be tested for inhibition of plant and insect cells, respectively. In addition, rational drug design can be used to exploit differences in the sequences of the yeast gene and the host gene homolog.

5.13 Pharmaceutical Applications

Potential antifungal compounds can be tested in heterologous host cell systems (e.g., human cells) to verify they do not affect proliferation or other cell functions to a significant degree. For instance, potential antifungal compounds can be used in a mammalian Genome Reporter Matrix system to make sure that the compounds do not adversely alter gene transcription (e.g., in an undesirable way). Similarly, potential anti-proliferative compounds can be tested to be sure that they do not adversely affect functions other than proliferation. Potential herbicidal and insecticidal compounds can also be tested for potential side effects in mammalian, preferably human, cell systems, such as the Genome Reporter Matrix system, for potential side effects on cellular functions. Of course, certain changes in gene transcription may be inevitable and many of these will not be deleterious to the patient or host organism. Once lead compounds have been identified, these compounds can be refined further via rational drug design and other standard pharmaceutical techniques. Ultimately, compounds can be used as effective antifungal agents, anti-proliferative drugs, herbicides and pesticides.

The antifungal agents of this invention may be formulated into pharmaceutical compositions and administered in vivo at an effective dose to treat a particular fungal disease. Similarly, the anti-proliferative drugs of this invention may be formulated into pharmaceutical compositions and administered in vivo at an effective dose to treat a particular proliferative disorder. Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the antifungal or anti-proliferative agents of this invention, including isolated and purified forms, their salts or pharmaceutically acceptable derivatives thereof, may be accomplished using any conventionally accepted mode of administration. The pharmaceutical compositions of the present invention may be administered to a subject such as a plant or animal in order to treat anti-fungal diseases or proliferative disorders. Such animals to be treated by the pharmaceutical compositions of the present invention include humans, non-human mammals including but not limited to monkeys and other primates, dogs, cats, ferrets, guinea pigs, cattle, sheep, pigs, goats and horses, and birds. The pharmaceutical compositions of the present invention may further be used to prevent contamination of mammalian and non-mammalian cells (e.g., insect cells) grown in tissue culture by fungi, e.g., yeast, by incubating such cells in cell culture medium containing an effective amount of the agent.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The antifungal or anti-proliferative agents of this invention may, for example, be placed into sterile, isotonic formulations with or without cofactors which stimulate uptake or stability. The formulation is preferably liquid, or may be lyophilized powder. For example, the inhibitors may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Alternatively, the composition may be pressurized and contain a compressed gas, such as nitrogen or a liquified gas propellant. The liquified propellant medium and indeed the total composition is preferably such that the active ingredient does not dissolve therein to any substantial extent.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The pharmaceutical compositions of this invention may also be administered using microspheres, microparticulate delivery systems or other sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al. (1985) *Biopolymers* 22:547–56; poly(2-hydroxyethyl-methacrylate) or ethylene vinyl acetate (Langer et al. (1981) *J. Biomed. Mater. Res.* 15:167–277; Langer (1982) *Chem. Tech.* 12:98–105).

The antifungal or anti-proliferative agents of this invention may also be attached to liposomes, which may optionally contain other agents to aid in targeting or administration of the compositions to the desired treatment site. Attachment of the antifungal or anti-proliferative agents to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al. (1992) *J. Cell. Biochem. Abst. Suppl.* 16E:77).

Liposomes containing antifungal or anti-proliferative agents may be prepared by well-known methods (See, e.g. DE 3,218,121; Epstein et al. (1985) *Proc. Natl. Acad. Sci. U.S.A.* 82:3688–92; Hwang et al. (1980) *Proc. Natl. Acad. Sci. U.S.A.* 77:4030–34; U.S. Pat. Nos. 4,485,045 and 4,544, 545). Ordinarily the liposomes are of the small (about 200–800 Angstroms) unilamellar type in which the lipid content is greater than about 30 mol. % cholesterol. The proportion of cholesterol is selected to control the optimal rate of MAG derivative and inhibitor release.

The compositions also will preferably include conventional pharmaceutically acceptable carriers well known in the art (see, e.g., *Remington's Pharmaceutical Sciences*, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

6. EXAMPLE 1: CONSTRUCTION OF THE YDR141c MUTANT STRAIN AND ANALYSIS OF TRANSFORMANTS

6.1 Construction of the YDR141c Mutant Strain

PCR for Chr 4 Round 1a Construct

All of the primers (both for construct PCR and analysis of the mutant) were organized in a 96-well format. The complete set of primers for each gene occupied a defined position on the 96-well plate (e.g. the UPTAG primer for YDR141C was in position F9 of the UPTAG block, and the analytical B primer for YDR141C was in position F9 of the B block). The sequences of the construct primers for the YDR141C locus are shown in FIG. 3. The UPTAG and DOWNTAG primers were resuspended in TE (10 mM Tris-HCl, 1 mM EDTA) to a concentration of 5 $\mu$M (UPTAG) and 7 $\mu$M (DOWNTAG). A PCR master mix for the entire set 6 was prepared by combining: 4263 $\mu$l H2O, 525 $\mu$l 10× Taq buffer (100 mM Tris-HCl (pH 8.5), 500 mM KCl, 15 mM MgCl2), 52.5 $\mu$l 20 mM dNTPs, 4 $\mu$l pFA6A-KanMX4 plasmid (approx. 2.5 $\mu$g), and 52.5 $\mu$l Taq Polymerase (5 units/$\mu$l). For each of the 96 reactions, 46.6 $\mu$l of the PCR master mix was transferred to the PCR plate with 3.4 $\mu$l primer mixes (2 $\mu$l UPTAG and 1.4 $\mu$l DOWNTAG, approx. 10 pmole each). The PCR reactions were performed using a Perkin Elmer 9600 PCR machine. The PCR conditions were as follows:

(1) initial denaturation at 94° C. for 3 minutes,
(2) 94° C. for 30 seconds,
(3) 54° C. for 30 seconds,
(4) 72° C. for 1 minute,
(5) cycle from step #2 for 25 times,
(6) perform final elongation at 72° C. for 3 minutes.

To visualize the PCR reactions, 4 $\mu$l loading buffer (12.5% glycerol, 0.1 mM EDTA, dye) was transferred to each well of a 96-well plate. 6 $\mu$l of each PCR reaction was then mixed with the loading buffer and run on a 1% agarose TBE gel (with 0.4 $\mu$g/ml ethidium bromide), and visualized with UV.

PCR for Chr 4 Round 2b Construct

The second round primers were resuspended in TE to a concentration of 23 $\mu$M for UPSTREAM45 and 18 $\mu$M for DOWNSTREAM45. 2 $\mu$l of each round 1a PCR product was transferred to the corresponding well of a 96-well PCR plate. Primers 3.5 $\mu$l UPSTREAM45 and 4.4 $\mu$l DOWNSTREAM45 (approx. 80 pmole each) were added to the PCR plate. A PCR master mix was prepared by combining: 8200 $\mu$l H2O, 1050 $\mu$l 10× Taq buffer, 105 $\mu$l 20 mM dNTPs, and 105 $\mu$l Taq polymerase. 90.1 $\mu$l of the master mix was transferred to each well of the PCR plate. The PCR reactions were performed using a Perkin Elmer 9600 PCR machine. The PCR conditions were as follows:

(1) initial denaturation at 94° C. for 3 minutes,
(2) 94° C. for 30 seconds,
(3) 54° C. for 30 seconds,
(4) 72° C. for 1 minute,
(5) cycle from step #2 for 25 times,
(6) perform final elongation at 72° C. for 3 minutes.

A 6 $\mu$l sample of each reaction was visualized by agarose gel electrophoresis as before. The remainder of each round 2 PCR reaction was purified by precipitation. 10 $\mu$l 3M NaOAc and 100 $\mu$l isopropanol was transferred to each well of a 96-well plate. Then 90 $\mu$l of the round 2 PCR reactions were transferred to the corresponding wells of the NaOAc/isopropanol plated and mixed. The plate was then incubated at −20° C. for 20 minutes, and centrifuged at 3400 rpm in a Sorvall RC-3B centrifuge for 30 minutes. The supernatants were removed and the DNA pellets were allowed to air dry. Shortly before the yeast transformations, the construct PCR products were resuspended in 30 $\mu$l TE.

Transformation of Yeast

The construct PCR products were transformed into two *S. cerevisiae* strains: a haploid strain R174 (also known as BY4741, MATα his3Δ1 leu2Δ0 met15Δ0 ura3Δ0) and a diploid strain R176 (also known as BY4743, MATα/MATαhis3Δ1/his3Δ1 leu2Δ0/let2Δ0 met15Δ0/MET15 LYS2/lys2Δ0 ura3Δ0/ura3Δ0) (Brachnmann et al., 1998). The yeast transformations were performed in a 96-well format, and the procedure was adapted from the standard lithium acetate method (Ito et al., 1983; Schiestl & Gietz, 1989), as described below. Two days before the transformations fresh cultures of R174 and R176 were inoculated from the frozen stocks in 3 ml YPD media and allowed to grow overnight at 30° C.; media and standard growth techniques were used (see Guthrie & Fink, 1991; Kaiser et al. (1994) *Methods in Yeast Genetics. A Cold Spring Harbor Laboratory Manual* (Cold Spring Harbor, N.Y.: Cold Spring Harbor Laboratory Press); Rose et al. (1989) *Laboratory Course Manual for Methods in Yeast Genetics* (Cold Spring Harbor, N.Y.: Cold Spring Harbor Laboratory Press)). The day prior to the transformations the cultures were diluted 1:50 in YPD and placed at 30° C. until they reached log phase growth. These actively dividing cells were then used to inoculate 100 ml YPD cultures and placed at 30° C. The volume of the inoculum was calculated such that the cultures would still be in log phase growth after 12 hours. The day of the transformations, the cultures were harvested and made competent. The optical density (O.D.) of the cultures was measured with a spectrophotometer (Hewlett-Packard 8452A Diode Array Spectrophotometer) at a wavelength of 600 nm to ensure that the cultures were in log phase growth (R174 O.D.600=2.04, R176 O.D.600=1.75). The cells were pelleted in a Sorvall RC-5C centrifuge with an SLA-1500 rotor at 2000 rpm for 5 minutes. The cells were washed with 100 ml 100 mM lithium acetate (LiOAc), pelleted again, and resuspended in 2 ml 100 mM LiOAc.

A LiOAc/PEG solution was prepared by dissolving 15 g polyethylene glycol (PEG 3350) in 16.5 ml $H_2O$ followed by filter sterilization. 12 ml of this PEG solution was then added to 1.5 ml sterile $H_2O$ and 1.5 ml sterile 100 mM LiOAc. The 2 ml competent cells were mixed with 22 µl carrier DNA (10 mg/ml sheared and boiled salmon sperm DNA). 10 µl of the round 2b construct PCR products was transferred to the corresponding well of a 96-well U-bottom plate. 25 µl of the cell/carrier DNA mix was added to each well. The plate was then incubated at 30° C. for 15 minutes. 150 µl of the LiOAc/PEG solution was then added to each well and mixed by pipetting up and down. The plate was then incubated at 30° C. for 60 minutes. Next, 17 µl DMSO was added to each well and the cells were heat shocked by placing the plate at 42° C. for 15 minutes. The cells were then pelleted in a Beckman GS-6R centrifuge at 1000 rpm for 3 minutes. The liquid was removed and the cells were resuspended in 200 µl YPD (each well). The cells were allowed to recover for 4 hours at 30° C. on a rotary shaker to express the KanMX marker. Transformants were selected for by plating the cells on YPD-G-418 (300 µg/ml) plates followed by growth at 30° C. Transformants were then colony-purified by restreaking to a second YPD-G-418 plate.

6.2 Analysis of Transformants

Whole Cell PCR Analysis

The transformants were analyzed utilizing whole cell PCR. The sequences of the six primers used for the analysis of the YDR141C locus (four gene specific, and two marker specific) are shown in FIG. 3. A sample of cells from a colony-purified transformant was picked with a pipet tip (not a toothpick), and smeared into the bottom of a PCR tube. Generally the cells were less than 3 days old. The tubes were then microwaved on high for 1 minute, and placed on ice in a metal block. A PCR master mix was prepared. For each reaction, the mix contained: 2 µl 2.5 mM dNTPs, 2 µl 10× Klentaq™ PCR reaction buffer (400 mM Tricine-KOH (pH 9.2), 150 mM KOAc, 35 mM $Mg(OAc)_2$, 750 µg/ml bovine serum albumin), 0.5 µl Klentaq™ (Clontech), and 13.5 µl $H_2O$. 18 µl of the PCR master mix was added to each tube containing the microwaved cells. Oligonucleotide primer pairs were then added using 1 µl of a 10 µM solution of each of the two primers of the pair. The following primer pairs were used: A/B, A/KanB, C/D, KanC/D, and A/D. The reactions were mixed by pipetting up and down. When the thermocycler had reached 94° C., the tubes in the metal block were taken off the ice and placed in the thermocycler. This is known as "hot start" PCR. The PCR reactions were generally performed using an MJ Research PTC-100 thennocycler using the following program:

(1) initial denaturation at 94° C. for 10 minutes,
(2) 94° C. for 30 seconds,
(3) 58° C. for 30 seconds,
(4) 68° C. for 1 minutes 30 seconds,
(5) cycle from step #2 for 35 times For the A/D primer pairs, the extension time (step #4) was increased to 3 minutes to compensate for the larger product that is produced by these flanking primers. Following the PCR, 2 µl of 10× loading buffer was added to each tube. 10 µl was removed and run on a 0.8% agarose TAE gel (with 0.4 µg/ml ethidium bromide), and visualized with UV. The sizes of the various PCR products were then compared with that which was expected. If all five analytical PCR reactions produced the expected results, it was deemed that the correct gene deletion ("knock-out") had been constructed.

Tetrad Analysis

Tetrad analysis was performed on the heterozygous mutant diploids following sporulation. Freshly grown cells were transferred to sporulation medium (1% KOAc (w/v), 20 µg/ml uracil, 20 µg/ml histidine, 40 µg/ml leucine) and incubated at room temperature for a minimum of 7 days. The asci of the tetrads were partially digested with zymolyase-20T (from *Arthrobacter luteus;* ICN). 100 µl of the sporulation culture was incubated with 1 µl zymolyase (10 mg/ml, 20 units/mg) for 10 minutes at room temperature. 15 µl was then dribbled onto a YPD plate and allowed to dry.

The tetrads were dissected and arrayed onto the YPD plate (Sherman & Wakem, 1991) utilizing a Narishige micromanipulator mounted onto the stage of an Olympus BH-TU microscope. Four spores of each tetrad were separated and placed in a vertical line on the surface of a YPD plate. The spores were allowed to germinate and grow at 30° C. for 2 days and then replica-plated to the following plates using sterile velveteens:

(1) YPD,
(2) YPD-G-418,
(3) YM-Ura His Leu Met Lys,
(4) YM-Ura His Leu Lys,
(5) YM-Ura His Leu Met,
(6) YM-MATa lawn (ABY57),
(7) YM-MATα lawn (ABY58).

The plates were incubated at 30° C. and the tetrads were scored for growth. The heterozygous loci (MAT, MET15, and LYS2) showed the expected segregation. The details of the tetrad analysis involving the YDR141C mutation are described in the section "Phenotypic Analysis of the YDR141(C Mutant Strain" (below).

Phenotypic Analysis of the YDR141C Mutant Strain

Tetrad analysis of the heterozygous ydr141cΔ::KanMX null mutation (R4331) demonstrated that the gene product was essential for germination and/or vegetative growth (FIG. 8). This was consistent with the inability to construct the YDR141C mutation in the haploid strain. Of the six tetrads analyzed, all segregated two live and two dead spores, indicating that there was a single heterozygous lethal mutation in the diploid strain. All of the twelve living spores were sensitive to G-418, indicating that they had inherited the wild-type allele of the YDR141C gene and that all of the dead spores had inherited the ydr141cΔ::KanMX null allele.

Sequence Comparisons

The YDR141C ORF contains 5,097 bp (FIG. 4), and is predicted to encode a protein of 1,698 amino acids (FIG. 5).

For the sequence analysis for Ydr141cp, the blastp version 2.0.4 (gapped) algorithm (Altschul et chcl., 1997) at the NCBI web site was used. The search of the amino acid sequence of Yfr003c was performed against the nonredundant database (defined as "nr" at the NCBI web site) and/or the Swiss protein database. Default parameters were used. The default setting of filtering the query sequence for regions of low complexity was also used. A slightly different algorithm, tblastn, was also used to search the same databases, as well as the EST database, using the amino acid sequence of Ydr141cp. The tblastn algorithm performs a dynamic comparison of the amino acid sequence of Ydr141cp against a nucleotide database that has been translated in all six possible reading frames. Although this algorithm is useful because it can identify homologs for nucleotide sequences that have not been translated, the results of this type of search must be carefully checked because many of the possible translations do not represent amino acid sequences of a protein found in nature. The Ydr141cp protein has a weak homolog in C. elegans (FIG. 6).

7. EXAMPLE 2: CONSTRUCTION OF THE YDR091c MUTANT STRAIN AND ANALYSIS OF TRANSFORMANTS 7.1 Construction of the YDR091c Mutuant Strain
PCR Conditions The Chr 4 Round 1a construct PCR and Round 2a construct PCR reactions are described in Example 1. The sequences of the four primers used for the construct PCR of YDR091C are shown in FIG. 9.
Transformation of Yeast The yeast transformation protocol for set 4 was the same as that used in Example 1. Both haploid (R174) and diploid (R176) strains were transformed. The cultures were harvested at the following densities: R174 O.D.$_{600}$=1.58, and R176 O.D.$_{600}$=1.43. Following the transformations, the cells were allowed to recover in YPD at 30° C. for four hours prior to being plated on YPD-G-418 (300 μg/ml) plates. The transformants were colony-purified by restreaking to a second YPD-G-418 plate.

7.2 Analysis of Transformants
Whole Cell PCR Analysis

Analysis of the set 4 mutations (including YDR091C) was performed by whole cell PCR exactly as described in Example 1. The sequences of the six primers used for the analysis of the YDR091C locus (four gene specific, and two marker specific) are shown in FIG. 9. All five analytical PCR primer pairs (A/B, A/KanB, C/D, KanC/D, and A/D) had to give the expected results in order for a mutant to be deemed correct.
Tetrad Analysis Tetrad analysis was performed on the set 4 heterozygous diploids following at least seven days of sporulation at room temperature. The tetrads were digested with Zymolyase and dissected on YPD plates, followed by growth at 30° C. The germinated tetrads were then scored for G-418 resistance, Met auxotrophy, Lys auxotrophy, and mating type by replica-plating to the same seven plates as in Example 1, followed by growth at 30° C. The heterozygous loci (MAT, MET15, and LYS2) showed the expected segregation. The details of the tetrad analysis involving the YDR091C mutation are described in the section "Phenotypic Analysis of the YDR091C Mutant Strain" (below).
Phenotypic Analysis of the YDR091C Mutant Strain Tetrad analysis of the heterozygous ydr091cΔ::KanMX null mutation (R4234) demonstrated that this hypothetical open reading frame not only was in fact a gene, but also that this gene was essential for germination and/or vegetative growth. This was consistent with the inability to construct the YDR091C mutation in the haploid strain. A total of six tetrads were analyzed by dissection. All segregated two live and two dead spores, indicating that there was a single heterozygous lethal mutation in the diploid strain (FIG. 15). All of the twelve living spores were sensitive to G-418, indicating that they had inherited the wild-type allele of the YDR091C gene and that all of the dead spores had inherited the ydr091cΔ::KanMX null allele.
Sequence Comparisons The YDR091C ORF contains 1,827 bp (FIG. 10), and is predicted to encode a protein of 608 amino acids (FIG. 11). The sequence analysis of the YDR091C encoded protein was performed using the blastp (version 2.0.4, gapped) and the tblastn algorithms at the NCBI web site. The default settings were used. Blastp was used to search the nr (non redundant) and/or the Swiss protein databases; tblastn was used to search the EST database. The predicted YDR091C encoded protein has strong (Type 1) homologs in Pyrococcus, Methanococcus, Methanobacterium, Archaeoglobus, and Homo sapiens, as well as many weak (Type 2) homologs in, inter alia, Arabidopsis, Synechocystis, Lactobacillus, Staphylococcus, and B. subtilis (FIG. 12). The polypeptide encoded by YDR091 C has 68% sequence identity (82% sequence homology) to the H. sapiens RNase L inhibitor (FIG. 13) and 65% sequence identity (81% sequence homology) to the H. sapiens 2'–5' oligoadenylate binding protein (FIG. 14).

8. EXAMPLE 3: CONSTRUCTION OF THE YOL022C MUTANT STRAIN AND ANALYSIS OF TRANSFORMANTS 8.1 Construction of the YOL022C Mutant Strain
PCR for Chr 15 Round 1a Construct The PCR conditions for set 15 were essentially the same as 4, with only minor adjustments. Again, all of the primers were organized in a 96-well format. The sequences of the construct primers for the YOL022C locus are shown in FIG. 16. The UPTAG and DOWNTAG primers were resuspended in TE to a concentration of 8.8 μM (UPTAG) and 8.1 μM (DOWNTAG). A PCR master mix was prepared by combining: 4379 μl H$_2$O, 525 μl 10× Taq buffer, 52.5 μl 20 mM dNTPs, 4 μl pFA6A-KanMX4 plasmid (approx. 2.5 μg), and 52.5 μl Taq Polymerase (5 units/μl). For each of the 96 reactions, 47.7 μl of the PCR master mix was transferred to the PCR plate with 2.3 μl primer mixes (1.1 μl UPTAG and 1.2 μl DOWNTAG, approx. 10 pmole each). The PCR reactions were performed using a Perkin Elmer 9600 PCR machine. The PCR conditions were as follows:

(1) initial denaturation at 94° C. for 3 minutes, (2) 94° C. for 30 seconds, (3) 54° C. for 30 seconds, (4) 72° C. for 1 minute, (5) cycle from step #2 for 20 times, (6) final elongation at 72° C. for 3 minutes.

The PCR reactions were visualized by gel electrophoresis as before.
PCR for Chr 15 Round 2a Construct The conditions for the second round of construct PCR were essentially as described above in Example 1. The second round primers were resuspended in TE to a concentration of 15 μM for UPSTREAM45 and 18 μM for DOWNSTREAM45. 2 μl of each round 1a PCR product was transferred to the corresponding well of a 96-well PCR plate. 2.7 µl of primer UPSTREAM45 and 2.2 µl of primer DOWNSTREAM45 (approx. 40 pmole each) were added. A PCR master mix was prepared by combining: 8516 µl H2O, 1050 µl 10× Taq buffer, 105 µl 20 mM dNTPs, and 105 µl Taq polymerase. 93.1 µl of the master mix was transferred to each well of the PCR plate with the primers. The PCR conditions were as follows:

(1) initial denaturation at 94° C. for 3 minutes,
(2) 94° C. for 30 seconds,
(3) 54° C. for 30 seconds,
(4) 72° C. for 1 minute,
(5) cycle from step #2 for 20 times,
(6) final elongation at 72° C. for 3 minutes.

A 6 µl sample of each reaction was visualized by agarose gel electrophoresis as before. The remainder of each round 2 PCR reaction was purified by precipitation as before. Shortly before yeast transformations, the construct PCR products were resuspended in 30 µl TE.

Transformation of Yeast

The yeast transformation protocol for set 15 was the same as that used to transform set 4. Again, both haploid (R174) and diploid (R176) strains were transformed. The cultures were harvested at the following densities: R174 O.D.600= 1.58, and R176 O.D.600=1.43. As before, following the transformations the cells were allowed to recover in YPD at 30° C. for 4 hours prior to being plated on YPD-G-418 (300 µg/ml) plates. The transformants were colony-purified by restreaking to a second YPD-G-418 plate.

8.2 Analysis of Transformants

Whole Cell PCR Analysis

Analysis of the set 15 mutations (including YOL022C) was performed by whole cell PCR exactly as described in Example 1. This is a standard technique for the analysis of mutant strains, during their construction and otherwise (i.e. for quality control, etc.). The sequences of the six primers used for the analysis of the YOL022C locus (four gene specific, and two marker specific) are shown in FIG. 16. As always, all five analytical PCR primer pairs (A/B, A/KanB, C/D, KanC/D, and A/D) had to give the expected results in order for a mutant to be deemed correct.

Tetrad Analysis

Tetrad analysis was performed essentially as described in Example 1. The analysis was performed on the set 15 heterozygous diploids following at least seven days of sporulation at room temperature. The tetrads were digested with Zymolyase and dissected on YPD plates, followed by growth at 30° C. The germinated tetrads were scored for G-418 resistance, Met auxotrophy, Lys auxotrophy, and mating type by replica-plating on the same seven plates as described in Example 1, followed by growth at 30° C. The heterozygous loci (MAT, MET15, and LYS2) showed the expected segregation. The details of the tetrad analysis involving the YOL022C mutation are described in the section "Phenotypic Analysis of the YOL022C Mutant Strain" (below).

Phenotypic Analysis of the YOL022C Mutant Strain

Tetrad analysis of the heterozygous yol022cΔ::KanMX null mutation (R3862) demonstrated that this hypothetical open reading frame not only was in fact a gene, but also that this gene was essential for germination and/or vegetative growth. This was consistent with the inability to construct the YOL022C mutation in the haploid strain. A total of six tetrads were analyzed by dissection. All segregated two live and two dead spores, indicating that there was a single heterozygous lethal mutation in the diploid strain (FIG. 20). All of the twelve living spores were sensitive to G-418, indicating that they had inherited the wild-type allele of the YOL022C gene and that all of the dead spores had inherited the yo1022cΔ::KanMX null allele.

Sequence Comparisons

The YOL022C ORF contains 1,227 bp (FIG. 17), and is predicted to encode a protein of 408 amino acids (FIG. 18). The sequence analysis of the YOL022C encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The predicted YOL022C encoded protein has a strong homolog (Type 1 homolog) in its own genome, and a weak homolog in *S. pombe* (FIG. 19).

9. EXAMPLE 4: CONSTRUCTION OF THE YOL026c MUTANT STRAIN AND ANALYSIS OF TRANSFORMANTS

9.1 Construction of the YOL026c Mutuant Strain

PCR Conditions

The Chr 15 Round 1a construct PCR and Round 2a construct PCR reactions are described in Example 3. The sequences of the four primers used for the construct PCR of YOL026C are shown in FIG. 21.

Transformation of Yeast

The yeast transformation protocol for set 15 was the same as that used to transform set 4 (Example 1). Both haploid (R174) and diploid (R176) strains were transformed. The cultures were harvested at the following densities: R174 O.D.$_{600}$=1.58, and R176 O.D.$_{600}$=1.43. Following the transformations the cells were allowed to recover in YPD at 30° C. for four hours prior to being plated on YPD-G-418 (300 µg/ml) plates. The transformants were colony-purified by restreaking to a second YPD-G-418 plate.

9.2 Analysis of Transformants

Whole Cell PCR Analysis

Analysis of the set 15 mutations (including YOL026C) was performed by whole cell PCR exactly described in Example 1. The sequences of the six primers used for the analysis of the YOL026C locus (four gene specific, and two marker specific) are shown in FIG. 21. All five analytical PCR primer pairs (A/B, A/KanB, C/D, KanC/D, and A/D) had to give the expected results in order for a mutant to be deemed correct.

Tetrad Analysis

Tetrad analysis was performed on the set 15 heterozygous diploids following at least seven days of sporulation at room temperature. The tetrads were digested with Zymolyase and dissected on YPD plates, followed by growth at 30° C. The germinated tetrads were then scored for G-418 resistance, Met auxotrophy, Lys auxotrophy, and mating type by replica-plating to the same seven plates as in Example 1, followed by growth at 30° C. The heterozygous loci (MAT. MET15, and LYS2) showed the expected segregation. The details of the tetrad analysis involving the YOL026C mutation are described in the section "Phenotypic Analysis of the YOL026C Mutant Strain" (below).

Phenotypic Analysis of the YOL026C Mutant Strain

Tetrad analysis of the heterozygous yo1026cΔ:KanMX null mutation (R3870) demonstrated that this hypothetical open reading frame not only was in fact a gene, but also that this gene was essential for germination and/or vegetative growth. This was consistent with the inability to construct the YOL026C mutation in the haploid strain. A total of six tetrads were analyzed by dissection. All segregated two live and two dead spores, indicating that there was a single heterozygous lethal mutation in the diploid strain (FIG. 25). All of the twelve living spores were sensitive to G-418, indicating that they had inherited the wild-type allele of the YOL026C gene and that all of the dead spores had inherited the yo1026cΔ::KanMX null allele. Thus, the lethality was linked to the mutant yo1026c allele.

Sequence Comparisons

The YOL026C ORF contains 342 bp (FIG. 22), and is predicted to encode a protein of 113 amino acids (FIG. 23). The sequence analysis of the YOL026C encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The polypeptide encoded by YOL026C has been identified as a previously-known membrane protein with no significant homologies to any other known proteins (FIG. 24).

10. EXAMPLE 5: CONSTRUCTION OF THE YOL034w MUTANT STRAIN AND ANALYSIS OF TRANSFORMANTS 10.1 Construction of the YOL034w Mutuant Strain
PCR Conditions The Chr 15 Round 1a construct PCR and Round 2a construct PCR reactions are described in Example 3. The sequences of the four primers used for the constrict PCR of YOL034W are shown in FIG. 26.

Transformation of Yeast

The yeast transformation protocol for set 15 was the same as that used to transform set 4 (Example 1). Both haploid (R174) and diploid (R176) strains were transformed. The cultures were harvested at the following densities: R174 O.D.$_{.600}$=1.58, and R176 O.D.$_{.600}$=1.43. Following the transformations the cells were allowed to recover in YPD at 30° C. for four hours prior to being plated on YPD-G-418 (300 μg/ml) plates. The transformants were colony-purified by restreaking to a second YPD-G-418 plate.

10.2 Analysis of Transformants
Whole Cell PCR Analysis

Analysis of the set 15 mutations (including YOL034W) was performed by whole cell PCR exactly described in Example 1. The sequences of the six primers used for the analysis of the YOL034W locus (four gene specific, and two marker specific) are shown in FIG. 26. All five analytical PCR primer pairs (A/B, A/KanB, C/D, KanC/D, and A/D) had to give the expected results in order for a mutant to be deemed correct.

Tetrad Analysis

Tetrad analysis was performed on the set 15 heterozygous diploids following at least seven days of sporulation at room temperature. The tetrads were digested with Zymolyase and dissected on YPD plates, followed by growth at 30° C. The germinated tetrads were then scored for G-418 resistance, Met auxotrophy, Lys auxotrophy, and mating type by replica-plating to the same seven plates as in Example 1, followed by growth at 30° C. The heterozygous loci (MAT, MET15, and LYS2) showed the expected segregation. The details of the tetrad analysis involving the YOL034W mutation are described in the section "Phenotypic Analysis of the YOL034W Mutant Strain" (below).

Phenotypic Analysis of the YOL034W Mutant Strain

Tetrad analysis of the heterozygous yo1034wΔ:KanMX null mutation (R3885) demonstrated that this hypothetical open reading frame not only was in fact a gene, but also that this gene was essential for germination and/or vegetative growth. This was consistent with the inability to construct the YOL034W mutation in the haploid strain. A total of six tetrads were analyzed by dissection. All segregated two live and two dead spores, indicating that there was a single heterozygous lethal mutation in the diploid strain (FIG. 31). All of the twelve living spores were sensitive to G-418, indicating that they had inherited the wild-type allele of the YOL034W gene and that all of the dead spores had inherited the yo1034wΔ::KanMX null allele. Thus, the lethality was linked to the mutant yo1034w allele.

Sequence Comparisons

The YOL034WORF contains 3,282 bp (FIG. 27), and is predicted to encode a protein of 1,093 amino acids (FIG. 28). The sequence analysis of the YOL034W encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The predicted YOL034W encoded protein has strong homologs in *S. pombe, C. elegans,* and *H. sapiens,* and weak homologs in, inter alia, its own genome, Methanococcus, Mycoplasma, and Entamoeba (FIG. 29). The polypeptide encoded by YOL034W exhibits 23% sequence identity (43% sequence homology) to an *H. sapiens* brain protein of unknown function (FIG. 30).

11. EXAMPLE 6: CONSTRUCTION OF THE YOL077c MUTANT STRAIN AND ANALYSIS OF TRANSFORMANTS 11.1 Construction of the YOL077c Mutuant Strain
PCR Conditions The Chr 15 Round 1 a construct PCR and Round 2a construct PCR reactions are described in Example 3. The sequences of the four primers used for the construct PCR of YOL077C are shown in FIG. 32.

Transformation of Yeast

The yeast transformation protocol for set 15 was the same as that used to transform set 4 (Example 1). Both haploid (R174) and diploid (R176) strains were transformed. The cultures were harvested at the following densities: R174 O.D.$_{.600}$=1.58, and R176 O.D.$_{.600}$=1.43. Following the transformations the cells were allowed to recover in YPD at 30° C. for four hours prior to being plated on YPD-G-418 (300 μg/ml) plates. The transformants were colony-purified by restreaking to a second YPD-G-418 plate.

11.2 Analysis of Transformants
Whole Cell PCR Analysis

Analysis of the set 11 mutations (including YOL077C) was performed by whole cell PCR exactly described in Example 1. The sequences of the six primers used for the analysis of the YOL077C locus (four gene specific, and two marker specific) are shown in FIG. 32. All five analytical PCR primer pairs (A/B, A/KanB, C/D, KanC/D, and A/D) had to give the expected results in order for a mutant to be deemed correct.

Tetrad Analysis

Tetrad analysis was performed on the set 15 heterozygous diploids following at least seven days of sporulation at room temperature. The tetrads were digested with Zymolyase and dissected on YPD plates, followed by growth at 30° C. The germinated tetrads were then scored for G-418 resistance, Met auxotrophy, Lys auxotrophy, and mating type by replica-plating to the same seven plates as in Example 1, followed by growth at 30° C. The heterozygous loci (MAT, MET15, and LYS2) showed the expected segregation. The details of the tetrad analysis involving the YOL077C mutation are described in the section "Phenotypic Analysis of the YOL077C Mutant Strain" (below).

Phenotypic Analysis of the YOL077C Mutant Strain

Tetrad analysis of the heterozygous yo1077cΔ::KanMX null mutation (R3965) demonstrated that this hypothetical open reading frame not only was in fact a gene, but also that this gene was essential for germination and/or vegetative growth. This was consistent with the inability to construct the YOL077C mutation in the haploid strain. A total of six tetrads were analyzed by dissection. All segregated two live and two dead spores, indicating that there was a single heterozygous lethal mutation in the diploid strain (FIG. 38). All of the twelve living spores were sensitive to G-418, indicating that they had inherited the wild-type allele of the YOL077C gene and that all of the dead spores had inherited the yo1077cΔ::KanMX null allele. Thus, the lethality was linked to the mutant yo1077c allele.

Sequence Comparisons

The YOL077C ORF contains 876 bp (FIG. 33), and is predicted to encode a protein of 291 amino acids (FIG. 34). The sequence analysis of the YOL077C encoded protein was performed using the blastp (version 2.0.4, gapped) and the tblastn algorithms at the NCBI web site. The default settings were used. Blastp was used to search the nr and/or the Swiss protein databases; tblastn was used to search the EST database. The polypeptide encoded by YOL077C has a strong homolog in *C. elegans* (FIG. 35). The polypeptide exhibits 44% sequence identity (66% sequence homology) to the *C. elegans* protein, which has an unknown function (FIG. 36). Amino acid sequence alignments of portion of Yo1077cp and ESTs from the *C. albicans* genome show that the polypeptide has one Type 1 homolog and two Type 2 homologs in the *C. albicans* genome (FIG. 37).

12. EXAMPLE 7: SCREENING ASSAY USING HYBRIDIZATION CHIPS TO IDENTIFY POTENTIAL ANTIFUNGAL AGENTS

A conditional allele of an essential yeast gene is produced as discussed above. The allele may be conditional either for function or expression. For instance, the conditional allele may be a temperature-sensitive allele of the essential gene or the essential gene may be operably linked to an inducible promoter for regulated expression.

The conditional allele is introduced into a yeast strain containing a functional deletion of the essential gene. The yeast strain containing the conditional allele is first grown under the permissive condition, allowing expression of the functional product of the essential gene, to permit the growth of the yeast strain for the assay. Then, the yeast strain is shifted to the nonpermissive condition, in which the product of the essential gene is either not made or is non-functional. The mRNA from the cells is extracted, reverse transcribed and labeled according to standard methods (see Sambrook et al., supra). The resultant cDNA is hybridized to an array of probes, e.g., a hybridization chip, the array is washed free of unhybridized labeled cDNA, the hybridization signal at each unit of the array quantified using a confocal microscope scanner, and the resultant matrix response data stored in digital form.

Hybridization chips may be made by any method known in the art, e.g., as described in U.S. Pat. No. 5,569,588. Unlabeled oligonucleotide hybridization probes complementary to the mRNA transcript of each yeast gene are arrayed on a silicon substrate etched by standard techniques. The probes are of length and sequence to ensure specificity for the corresponding yeast gene, typically about 24–240 nucleotides in length.

The genome expression profile of the yeast strain under the nonpermissive condition is compared to the expression profile of either the same yeast strain grown tinder permissive conditions or a wildtype yeast strain and identifies those genes which are either induced or repressed by expression of the essential gene. The genes are that are regulated by the expression of the essential gene are then used to screen for antifungal agents.

Wildtype yeast cells or yeast cells grown under permissive conditions are incubated with compounds that are potential antifungal agents. These compounds may be drawn from libraries of natural compounds, combinatorial libraries, or other synthetic compounds. The mRNA from the each of the treated yeast cells is extracted and labeled cDNA is prepared. The cDNA is hybridized to hybridization chips to obtain genome expression profiles for each compound tested. If a genome expression profile of the yeast cell treated with a compound is similar to that of the yeast strain grown under the non-permissive conditions, then the compound is tested for its ability to inhibit wildtype yeast vegetative growth and germination. See U.S. Pat. Nos. 5,569,588 and 5,777,888.

Potential herbicides, insecticides and anti-proliferation agents may be screened in a similar fashion by using plant, insect or mammalian cells, respectively, rather than yeast cells.

13. EXAMPLE 8: SCREENING ASSAY USING THE GENOME REPORTER MATRIX TO IDENTIFY ANTIFUNGAL COMPOUNDS

The essential gene of interest is transfected and overexpressed in yeast cells of the Genome Reporter Matrix (GRM). See U.S. Pat. No. 5,569,588. The transcription of all of the genes of the GRM is measured in response to the overexpression and compared to the transcription of these genes in cells that do not overexpress the essential gene. Thus, one can identify a subset of genes that are either induced or repressed by overexpression of the essential gene.

The yeast strains containing the subset of genes regulated by overexpression of the essential gene are then used to screen potential antifungal compounds. The yeast strains are incubated with potential antifungal compounds. If a tagged gene in a particular yeast strain is induced by overexpression of the essential gene, then potential antifungal compounds are screened for the ability to downregulate the tagged gene. Conversely, if a tagged gene is repressed by overexpression of the essential gene, then potential antifungal compounds are screened for the ability to upregulate the tagged gene. Potential antifungal compounds are screened for the ability to appropriately upregulate and downregulate a number of the genes that whose expression is altered by overexpression of the essential gene. When potential antifungal compounds are identified, these candidate compounds are tested for their ability to inhibit wildtype yeast vegetative growth and germination.

In a similar fashion, potential herbicides may be tested by using a GRM derived from plant cells, potential insecticides may be tested by using a GRM derived from insect cells, and potential anti-proliferation compounds may be tested by using a GRM derived from mammalian cells. Mammalian, insect and plant GRMs are described in U.S. Pat. No. 5,569,588.

14. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method to identify a potential antifungal compound, comprising the steps of
   a) contacting a protein comprising an amino acid sequence encoded by an essential gene selected from the group consisting of YDR141C, YDR091C, YOL022C, YOL026C, YOL034W, and YOL077C with a compound under conditions effective to promote specific binding between the protein and the compound; and
   b) determining whether the protein bound to the compound;
wherein the compound is a potential antifungal compound if the compound binds to the protein.

2. The method according to claim 1 wherein the protein comprises the mature polypeptide encoded by the essential gene.

3. The method according to claim 1 wherein the protein comprises a functional fragment of the amino acid sequence encoded by the essential gene.

4. The method according to claim 1 wherein the protein is a fusion protein comprising an epitope tag or reporter sequence.

5. The method according to claim 1 wherein the protein is attached to a solid support surface and the compound is in mobile phase.

6. The method according to claim 1 wherein the compound is attached to a solid Support surface and the protein is in mobile phase.

7. The method according to claim 1 wherein the compound is a library selected from the group consisting of a combinatorial small organic library, a phage display library and a combinatorial peptide library.

8. The method according to claim 1 wherein said determining is performed by ELISA, RIA or BiaCORE analysis.

9. The method of claim 1 wherein the protein is recombinantly expressed by a cell and is contacted by the compound in situ.

10. The method according to claim 1 wherein said determining is performed by high throughput screening.

11. The method according to claim 1 further comprising the step of determining whether the potential antifungal compound can inhibit yeast germination or vegetative growth.

12. A method to identify genes that an essential gene selected from the group consisting of YDR141C, YDR091C, YOL022C, YOL026C, YOL034W, and YOL077C regulates, comprising the steps of
   a) overexpressing the essential gene in one or more cells; and
   b) identifying genes that are either induced or repressed by overexpression of the essential gene.

13. The method according to claim 12 wherein the cells are of a Genome Reporter Matrix.

14. A method to identify potential antifungal compounds, comprising the steps of
   a) overexpressing an essential gene of yeast selected from the group consisting of YDR141C, YDR091C, YOL022C, YOL026C, YOL034W, and YOL077C in one or more cells;
   b) isolating a subset of genes that are either induced or repressed by overexpression of the essential gene; and
   c) determining the effects of compounds on the down-regulation or up-regulation of any of said subset of genes induced or repressed by overexpression of the essential gene;
   wherein a compound is a potential antifungal compound if it downregulates a gene that is induced by overexpression of the essential gene or if it upregulates a gene that is repressed by overexpression of the essential gene.

15. The method according to claim 14 wherein the cells are of a Genome Reporter Matrix.

\* \* \* \* \*